US010781203B2

(12) United States Patent
Buchkovich et al.

(10) Patent No.: US 10,781,203 B2
(45) Date of Patent: Sep. 22, 2020

(54) NONTOXIC COMPOUNDS FOR THE TREATMENT AND PREVENTION OF HERPESVIRUS INFECTIONS

(71) Applicant: The Penn State Research Foundation, University Park, PA (US)

(72) Inventors: Nicholas J. Buchkovich, Palmyra, PA (US); Linda M. Cruz, Elizabethtown, PA (US); Dhimant H. Desai, Mechanicsburg, PA (US); Shantu Amin, Union City, NJ (US); Aron Lukacher, Hummelstown, PA (US); Saumya Maru, Hershey, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 16/318,725

(22) PCT Filed: Jul. 20, 2017

(86) PCT No.: PCT/US2017/043108
§ 371 (c)(1),
(2) Date: Jan. 18, 2019

(87) PCT Pub. No.: WO2018/017853
PCT Pub. Date: Jan. 25, 2018

(65) Prior Publication Data
US 2019/0241553 A1 Aug. 8, 2019

Related U.S. Application Data

(60) Provisional application No. 62/364,608, filed on Jul. 20, 2016.

(51) Int. Cl.
| C07D 417/14 | (2006.01) |
| A61K 31/517 | (2006.01) |
| C12N 15/113 | (2010.01) |
| A61P 31/22 | (2006.01) |

(52) U.S. Cl.
CPC .......... *C07D 417/14* (2013.01); *A61K 31/517* (2013.01); *A61P 31/22* (2018.01); *C12N 15/1133* (2013.01); *C12N 2310/141* (2013.01)

(58) Field of Classification Search
CPC .................................................. C07D 417/14
USPC .................................................... 514/266.24
See application file for complete search history.

(56) References Cited

U.S. PATENT DOCUMENTS

| 5,262,564 A | 11/1993 | Kun et al. |
| 6,011,020 A | 1/2000 | Gold et al. |
| 2015/0166517 A1 | 6/2015 | Atwood et al. |
| 2015/0250788 A1 | 9/2015 | Gillet et al. |
| 2015/0291568 A1 | 10/2015 | Gillet et al. |

FOREIGN PATENT DOCUMENTS

| CN | 106880630 A | 6/2017 |
| EP | 2722047 | 4/2014 |
| EP | 3085374 | 10/2016 |
| WO | WO2005117876 | 12/2005 |
| WO | WO2012087938 | 6/2012 |

OTHER PUBLICATIONS

Niknam, K. et al, "Silica-bonded N-propylsulfamic acid as a recyclable catalyst for the synthesis of 2,3-dihydroquinazolin-4(1H)0ones", Chinese Chemical Letters, Amsterdam, NL, vol. 22, No. 1, pp. 69-72, XP027559177, (Jan. 2011).
Cruz, L. et al, "Potent inhibition of human cytomegalovirus by modulation of cellular SNARE syntaxin 5", Journal of Virology, 91(1), pp. e01637-16, XP055417671, (Oct. 2016).
Noel, R. et al, "Methyldihydroquinazolinone derivaties of Retro-2 with enhanced efficacy against Shiga toxin", Journal of Medicinal Chemistry, 56(8), pp. 3404-3413, XP055095031, (Apr. 2013).
Britt, W., "Human cytomegalovirus: propagation, quantification, and storage", Curr. Protoc. Microbiol., Chapter 14: Unit 14E.3, (Aug. 2010).
Carney, D. et al, "Structural optimization of a retrograde trafficking inhibitor that protects cells from infections by human polyoma- and papillomaviruses", Bioorganic & Medicinal Chemistry, 22(17), pp. 4836-4847, XP055369816, Sep. 2014).
Das, S. et al, "Identification of human cytomegalovirus genes important for biogenesis of the cytoplasmic virion assembly complex", Journal of Virology, vol. 88(16), pp. 9086-9099, (Aug. 2014).
Buchkovich, N. et al, "The endoplasmic reticulum chaperone BiP/GRP78 is important in the structure and function of the human Cytomegalovirus assembly compartment", Journal of Virology, vol. 83(22), pp. 11421-11428, (Nov. 2009).
Buchkovich, N. et al, "Role of the endoplasmic reticulum chaperone BiP, SUN domain proteins, and Dynein in altering nuclear morphology during human cytomegalovirus infection", Journal of Virology, vol. 84(14), pp. 7005-7017, (Jul. 2010).
Indran, S. et al, "Bicaudal D1-dependent trafficking of human cytomegalovirus tegument protein pp150 in virus-infected cells", Journal of Virology, vol. 84(7), pp. 3162-3177, (Apr. 2010).
Harel, N. et al, "Phosphorylation of the human cytomegalovirus 86-Kilodalton immediate-early protein IE2", Journal of Virology, vol. 72(7), pp. 5481-5492, (Jul. 1998).
Krzyzaniak, M. et al, "HCMV-encoded-glycoprotein M (UL100) interacts with Rab11 effector protein FIP4", Traffic, vol. 10, pp. 1439-1457, (Jul. 2009).

(Continued)

*Primary Examiner* — Taofiq A Solola
(74) *Attorney, Agent, or Firm* — Meunier Carlin & Curfman LLC

(57) ABSTRACT

Compositions for preventing or treating virus infections inhibit the biogenesis of cytoplasmic viral assembly compartment (cVAC). The preferred compounds are dihydroquinazolinones.

7 Claims, 16 Drawing Sheets
(9 of 16 Drawing Sheet(s) Filed in Color)
Specification includes a Sequence Listing.

(56) References Cited

OTHER PUBLICATIONS

Hook, L. et al, "Cytomegalovirus miRNAs target secretory pathway genes to facilitate formation of the viron assembly compartment and reduce cytokine secretion", Cell Host & Microb., vol. 15, pp. 363-373, (Mar. 2014).

Spector, D. et al, "UL84-independent replication of human cytomegalovirus strain TB40/E", Virology, vol. 407, pp. 171-177, (2010).

Spector, D. et al, "UL84-independent replication of human cytomegalovirus strains conferred by a single codon change in UL122", Virology, vol. 476, pp. 345-354, (2015).

Warming, S. et al, "Simple and highly efficient BAC recombineering using galK selection", Nucleic Acids Research, vol. 33(4), p. e36, (2005).

Xu, D. et al, "Subunit structure of a mammalian ER/Golgi SNARE complex*", Journal of Biological Chemistry, vol. 275(50), pp. 39631-39639, (2000).

Zhang, T. et al, "Ykt6 forms a SNARE complex with syntaxin 5, GS28, and Bet1 and participates in a late stage in endoplasmic reticulum-Golgi", Journal of Biological Chemistry, vol. 276(29), pp. 27480-27487, (2001).

Fasshauer, D. et al, "Conserved structural features of the synaptic fusion complex: SNARE proteins reclassified as Q-and R-SNAREs", Proc. Natl. Acad. Sci., USA, vol. 95, pp. 15781-15786, (Dec. 1998).

Xu, Y. et al, "GS15 forms a SNARE complex complete with syntaxin 5, GS28, and Ykt6 and is implicated in traffic in the early cisternae of the Golgi apparatus", Molecular Biology, vol. 13, pp. 3493-3507, (Oct. 2002).

Tai, G. et al, "Participation of the syntaxin 5/Ykt6/GS28/GS15 SNARE complex in transport from the early/recycling endosome to the trans-Golgi network", Molecular Biology, vol. 15, pp. 4011-4022, (Sep. 2004).

Volchuk, A. et al, "Countercurrent distribution of the two distinct SNARE complexes mediating transport within the Golgi stack", Molecular Biology, vol. 15, pp. 1506-1518, (Apr. 2004).

Stechmann, B. et al, "Inhibition of retrograde transport protects mice from lethal Ricin challenge", Cell, vol. 141, pp. 231-242, (Apr. 2010).

Das, S. et al, "Three-dimensional structure of the human cytomegalovirus cytoplasmic virion assembly complex includes a reoriented secretory apparatus", Journal of Virology, vol. 81(21), pp. 11861-11869, (Nov. 2007).

Cepeda, V. et al, "A role for the SNARE protein syntaxin 3 in human cytomegalovirus morphogenesis", Cellular Microbiology, vol. 13(6), pp. 846-858, (Mar. 2011).

Gupta, N. et al, "(S)-N-methyldihydroquinazolinones are the active enantiomers of retro-2 derived compounds against toxins", Medical Chemistry Letters, vol. 5, pp. 94-97, (2014).

Parlati, F. et al, "Distinct SNARE complexes mediating membrane fusion in Golgi transport based on combinatorial specificity", PNAS, vol. 99(8), pp. 5424-5429, (Apr. 2002).

Weinberger, A. et al, "Control of Golgi morphology and function by Sed5 t-SNARE phosphorylation", Molecular Biology, vol. 16, pp. 4918-4930, (Oct. 2005).

Rabouille, C. et al, "Syntaxin 5 is a common component of the NSF-and p97-mediated reassembly pathways of Golgi cisternae from mitiotic Golgi fragments in vitro", Cell, vol. 92, pp. 603-610, (Mar. 1998).

Miyazaki, K. et al, "Contribution of the long form of syntaxin 5 to the organization of the endoplasmic reticulum", Journal of Cell Science, pp. 5658-5666, (Sep. 2012).

Nelson, C. et al, "A retrograde trafficking inhibitor of Ricin and Shiga-like toxins inhibits infection of cells by human and monkey polyamaviruses", mBio, vol. 4(6), e00729-13, (Nov./Dec. 2013).

Lipovsky, A. et al, "Genome-wide siRNA screen identifies the retromer as a cellular entry factor for human papillomavirus", PNAS, vol. 110(18), pp. 7452-7457, (Apr. 2013).

Rendon, W. et al, "Golgi fragmentation is Rab and SNARE dependent in cellular models of Parkinson's disease", Histochem. Cell Biol., vol. 139(5), pp. 671-684, (May 2013).

Dai, W. et al, "Antiviral effects on Retro-2cycl and retro-2.1 against enterovirus 71 in vitro and in vivo", Antiviral Research, pp. 311-321, XP-002774910, (2017).

Liu, S. et al, "Synaptic vescile-like lipidome of human cytomegalovirus virions reveals a role for SNARE machinery in virion egress", PNAS, vol. 108(31), pp. 12869-12874, (Aug. 2011).

Enatiomers of DBAL-CM (10a) and (10b)

Enantiomers of DABL-CN
Waters Model 510 pump
Waters Model 2487 UV detector
25 μl injection
Phenomenex 150 x 4.6mm stainless steel column packed with Cellulose -1 was used for analysis.
The mobile phase: mixture of hexane/ethanol (60/40) with 0.1% diethylamine.
Flow rate was 1.0 mL/min

SEQUENCE LISTING

```
<160> NUMBER OF SEQ ID NOS: 31

<210> SEQ ID NO 1
<211> LENGTH: 78
<212> TYPE: DNA
<213> ORGANISM: Artificial Sequence
<220> FEATURE:
<223> OTHER INFORMATION: Description of Artificial Sequence:  Synthetic
      oligonucleoetide

<400> SEQUENCE: 1
gatcctggag gcttgctgaa ggctgtatgc tcaggaccca tggcctgtta ctagcactca        60
catggaacaa atggccca                                                     78

<210> SEQ ID NO 2
<211> LENGTH: 98
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gatcctggag gcttgctgaa ggctgtatgc tgagacacca tgcagaacat tgagttttgg        60
ccactgactg actcaatgtt gcatggtgtc tcaggacc                                98

<210> SEQ ID NO 3
<211> LENGTH: 98
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 3
catgggtcct gagacaccat gcaacattga gtcagtcagt ggccaaaact caatgttctg    60
catggtgtct cagcatacag ccttcagcaa gcctccag                            98

<210> SEQ ID NO 4
<211> LENGTH: 98
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gatcctggag gcttgctgaa ggctgtatgc tgaaatcgct gatttgtgta gtcgttttgg    60
ccactgactg acgactacac atcagcgatt tcaggacc                            98

<210> SEQ ID NO 5
<211> LENGTH: 98
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
catgggtcct gaaatcgctg atgtgtagtc gtcagtcagt ggccaaaacg actacacaaa    60
tcagcgattt cagcatacag ccttcagcaa gcctccag                            98

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gcatgaattc atggtgagca agggcgag                                       28

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gcattctaga ttacttgtac agctcgtc                                       28

<210> SEQ ID NO 8
<211> LENGTH: 74
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 8
aacgtccacc cacccccggg acaaaaaagc ccgccgcctc cttgcccttt cctgttgaca    60
attaatcatc ggca                                                     74

<210> SEQ ID NO 9
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tgtcccattc ccgactcgcg aatcgtacgc gagacctgaa agtttatgag tcagcactgt    60
cctgctcctt                                                          70

<210> SEQ ID NO 10
<211> LENGTH: 71
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
aacgtccacc cacccccggg acaaaaaagc ccgccgcctc cttgcccttt cgggatcccg    60
ccaccatggt g                                                        71

<210> SEQ ID NO 11
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tgtcccattc ccgactcgcg aatcgtacgc gagacctgaa agtttatgag ttacttgtac    60
agctcgtcca                                                          70

<210> SEQ ID NO 12
<211> LENGTH: 75
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gccgtgcaga acatcctcca aaagatcgag aagattaaga acacggagga acctgttgac    60
aattaatcat cggca                                                    75

<210> SEQ ID NO 13
<211> LENGTH: 76
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 13
acacgtcact atccgatggt ttcattaaaa agtacgtctg cgtgtgtgtt tcttaatcag      60
cactgtcctg ctcctt                                                     76

<210> SEQ ID NO 14
<211> LENGTH: 75
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gccgtgcaga acatcctcca aaagatcgag aagattaaga acacggagga accaccggtc     60
gccaccatgg tgagc                                                     75

<210> SEQ ID NO 15
<211> LENGTH: 80
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
acacgtcact atccgatggt ttcattaaaa agtacgtctg cgtgtgtgtt tcttaattac     60
ttgtacagct cgtccatgcc                                                80

<210> SEQ ID NO 16
<211> LENGTH: 74
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cgtttgccgt tgggcgtacg ctacgtttgt atttctggct ataatatgtg cctgttgaca     60
attaatcatc ggca                                                      74

<210> SEQ ID NO 17
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
atacacccta cagtcacacc cttcccaata ggaacatcga cacatgaccg tcagcactgt     60
cctgctcctt                                                           70

<210> SEQ ID NO 18
<211> LENGTH: 68
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 18
cgtttgccgt tgggcgtacg ctacgtttgt atttctggct ataatatgtg gagtaattca      60
tacaaaag                                                              68

<210> SEQ ID NO 19
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19 atacaccta cagtcacacc cttcccaata ggaacatcga cacatgaccg ccatagagcc       60
caccgcatcc                                                            70

<210> SEQ ID NO 20
<211> LENGTH: 74
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
agggtggcga ggtgtgagga tgaaacatat gcagatacgc agtgttgtta cctgttgaca      60
attaatcatc ggca                                                       74

<210> SEQ ID NO 21
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gactttcata ctgaagtacc gttgtacgca ttacacgggt ttcgttcgga tcagcactgt      60
cctgctcctt                                                            70

<210> SEQ ID NO 22
<211> LENGTH: 68
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
agggtggcga ggtgtgagga tgaaacatat gcagatacgc agtgttgtta aagtgccacc      60
tgacgtcg                                                              68

<210> SEQ ID NO 23
<211> LENGTH: 68
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 23
gactttcata ctgaagtacc gttgtacgca ttacacgggt ttcgttcgga gtgagcgagg    60
aagctcgg                                                            68

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
atgtcctgcc gggatcggac                                               20

<210> SEQ ID NO 25
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
catcaaagag ggacttgcgc tttgcc                                        26

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ttcagcaagc aaatcagcag                                               20

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gaatgatgat gcacagggtt t                                             21

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cagctgttag ccgagcaagt                                               20

<210> SEQ ID NO 29
<211> LENGTH: 19
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 29
catcagcaag ctcgtccag                                                    19

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ttcttctgga acacaggaaa gat                                               23

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tctgggcatc ctggtctatc                                                   20
```

NONTOXIC COMPOUNDS FOR THE TREATMENT AND PREVENTION OF HERPESVIRUS INFECTIONS

CROSS REFERENCE TO RELATED APPLICATIONS

This is a national stage filing in accordance with 35 U.S.C. § 371 of PCT/US2017/043108, filed Jul. 20, 2017, which claims the benefit of the priority of U.S. Provisional Patent Application No. 62/364,608, filed Jul. 20, 2016, the contents of each are incorporated herein by reference.

FIELD OF THE INVENTION

The invention generally relates to compositions and methods of use in protecting and treating viral infections, in particular herpes viruses.

BACKGROUND

Human cytomegalovirus (HCMV), also referred to as human herpesvirus 5, is a ubiquitous virus that causes severe disease and mortality in the immunocompromised. Additionally, infection of a developing fetus can result in lifetime complications that include learning disabilities and deafness. One hallmark of HCMV infection is the profound reorganization of cellular organelles to form a cytoplasmic viral assembly compartment (cVAC). The cVAC consists of loosely associated organelle specific vesicles organized in concentric layers (Das S, et al. *J Virol.* 2007; 81(21):11861-9). Viral proteins important for tegument acquisition and envelopment localize to the cVAC. It has been proposed that as nucleocapsids exit the nucleus, they traverse the layers of the cVAC where tegument acquisition and envelopment occur (Das S, et al. *J Virol.* 2007; 81(21):11861-9). This cVAC is essential for efficient virus replication and production of infectious virions is severely inhibited in the absence of a morphologically intact assembly compartment.

SUMMARY

Embodiments of the invention are directed to compounds for the prevention and treatment of virus infections. In certain embodiments, compounds of the invention are set forth in Formula I:

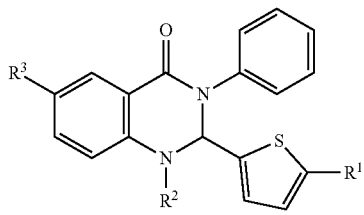

I or a pharmaceutically acceptable salt thereof, wherein:

$R^1$ comprises H, O, 2-methylthiazol, an aromatic heterocyclic group; or an aromatic heterocyclic group substituted by: a $C_1$-$C_{10}$ alkyl group; a halogen atom; a phenyl group; a phenyl group substituted by one or more of: a $C_1$-$C_{10}$ alkoxy group, and a group —CN, —$NO_2$, —COX and —COOX, X being a $C_1$-$C_4$ alkyl radical; a group —SY, Y being a $C_1$-$C_4$ alkyl group or a phenyl group; —CN; a group —$CH_2$—$N_3$; a group —$CH_2$—$N_3$; an aromatic heterocyclic group selected from the group consisting of furan, thiophene, pyrrole, pyrroline, pyrrolidine, dioxolane, oxazole, thiazole, imidazole, imidazoline, imidazolidine, pyrazole, isoxazole, isothiazole, pyran, pyridine, piperidine, dioxane, morpholine, pyridazine, pyrimidine and pyrazine, each of which is optionally substituted by at least one $C_1$-$C_3$ alkyl radical and/or a group —$CH_2$—$N_3$ thereof; a phenyl group or a phenyl group substituted by a $C_1$-$C_3$ alkoxy group or $NMe_2$; and, $R^2$ is H, OH, $CH_3$, halogen, $C_{1-10}$ alkyl, the $C_{1-10}$ alkyl is unsubstituted or optionally substituted with a functional group selected from the group consisting of H, —OH, —OR', —$NH_2$, —NHR', —$NR'_2$, —SH, —SR', —O—C(O)R', —C(O)R', —$CF_3$, —$OCF_3$, where R' is selected from radicals consisting of H, heteroaryl having 1 to 4 N, O, halogen and/or S atoms, $C_{1-10}$ alkyl, $C_{2-10}$ alkenyl, $C_{2-10}$ alkynyl, $C_{4-10}$ heterocycle and $C_{4-10}$ heteroaryl; and, $R^3$ is hydrogen atom, a halogen atom or a $C_1$-$C_3$ alkoxy group, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, and substituted or unsubstituted heteroaryl, H, —OH, —OR', —$NH_2$, —NHR', —$NR'_2$, —SH, —SR', —O—C(O)R', —C(O)R', $(CH_2)_bNH_2$, $C_{(m+1)}H_{(2m+1)}$, $C_{(m+1)}H_{(2m+1)}NH_2$, $C_{(m+1)}H_{(2m+1)}CONH_2$, $C_{(m+1)}H_{(2m+1)}$, $CR'NH_2$, $C_{(m+1)}H_{(2m+1)}$—$C_{4-20}$ aryl-$C_{(m+1)}H_{(2m+1)}$—$NH_2$, $C_mH_{2m+2}$, $C_{4-20}$ aryl, $C_{1-20}$ alkyl, $C_{1-20}$ alkylamino, $C_{2-20}$ alkenyl, $C_{2-20}$ alkynyl, $C_{4-20}$ heterocycle, $C_{4-20}$ heteroaryl, $C_{4-20}$ alkyl heterocycle, $C_{7-20}$ alkyl heteroaryl, $C_{1-20}$ alkyoxyl, where m is an integer from 0 to 10, and b is an integer from 0 to 10, wherein, the $C_{4-20}$ aryl, $C_{1-20}$ alkyl, $C_{2-20}$ alkenyl, $C_{2-20}$ alkynyl, $C_{4-20}$ heterocycle, $C_{4-20}$ heteroaryl, $C_{4-20}$ alkyl heterocycle, $C_{7-20}$ alkyl heteroaryl, $C_{1-20}$ alkyoxyl is unsubstituted or optionally substituted with a functional group comprising H, —OH, —OR', —$NH_2$, —NHR', —$NR'_2$, —SH, —SR', —O—C(O)R', —C(O)R', —$CF_3$, —$OCF_3$, the $C_{4-20}$ aryl, $C_{1-20}$ alkyl, $C_{2-20}$ alkenyl, $C_{2-20}$ alkynyl, $C_{4-20}$ heterocycle, $C_{4-20}$ heteroaryl, $C_{4-20}$ alkyl heterocycle, $C_{7-20}$ alkyl heteroaryl, $C_{1-20}$ alkyoxyl, and the $C_{1-6}$ alkyl is optionally interrupted by one or more O, S, or N atoms, or one or more groups comprising cycloalkyl, $C_{(m+1)}H_{(2m+1)}$, $C_{(m+1)}H_{(2m+1)}NH_2$, CH—C(O)—O—, —O—C(O)—, —C(O)—, —C(O)—NH—, —NH—C(O)—, —NH—C(O)—O— and —O—C(O)—NH—, R' is H, OH, halogen, —$CH_3$, $NO_2$, —$NH_2$, CN, —COOH, heteroaryl having 1 to 4 N, O and/or S atoms, $C_{4-20}$ aryl, $C_{1-10}$ alkyl, $C_{2-10}$ alkenyl, $C_{2-10}$ alkynyl, $C_{4-10}$ heterocycle or $C_{4-10}$ heteroaryl.

Other aspects are described infra.

BRIEF DESCRIPTION OF THE DRAWINGS

The patent or application contains at least one drawing executed in color. Copies of this patent or patent application publication with color drawings will be provided by the Office upon request and payment of the necessary fee.

FIG. 1A is a schematic showing Qa SNARES involved in Golgi-related trafficking. FIG. 1B. shows Western blot analysis of Qa SNAREs from lysates harvested from uninfected cells (Mock) or cells HCMV-infected (MOI=3) for 24, 48, 72 or 96 hours. FIG. 1C is a qRT-PCR of STX5 and STX18 from RNA samples harvested from cells at the times indicated in FIG. 1A. FIG. 1D is an immunofluorescence analysis showing STX5 (green) localization in uninfected (Mock) or HCMV-infected cells at 96 hours post infection (hpi) relative to pp28 (red). Nuclei labeled with DAPI (blue). Scale bars: 10 μm. FIG. 1E is a schematic showing STX5 containing SNARE complexes. FIG. 1F is a Western blot analysis from lysates as described in FIG. 1A showing protein expression of STX5-interacting SNARE proteins. FIG. 1G shows the immunofluorescence detection of STX5-interacting Qb SNAREs (GS28 & GS27, green) in uninfected (Mock) cells and at 96 hpi relative to pp28 (red). Nuclei labeled with DAPI (blue).

FIG. 2A is a schematic showing the design of inducible miRNA expressing locus inserted between UL34a and TRS1. FIG. 2B shows the quantification of viral titers from miLUC or miSTX5 infections treated with or without doxycycline (10 μg/ml) at 9 dpi (MOI=0.05). FIG. 2C shows bright field images of CPE associated with infections in FIG. 2B. FIG. 2D shows a Western blot analysis of STX5 protein 96 hours after infection with miSTX5 (MOI=3) in presence or absence of doxycycline.

FIG. 3A is a growth curve analysis of HCMV (MOI=3) in untreated (WT), vehicle treated (DMSO) or Retro94-treated cells. Samples were harvested at 24, 48, 72, 96, 120 and 144 hpi. FIG. 3B shows the immunofluorescence detection of STX5 in uninfected (Mock) and HCMV-infected cells (96 hpi) in the presence of DMSO control or Retro94. Nuclei labeled with DAPI (blue). Scale bars: 10 μm. FIG. 3C is a growth curve analysis of HCMV (MOI=0.05) in DMSO control (DMSO) or Retro94-treated cells. Samples were harvested at 3, 6, 9, 12 and 15 dpi. Asterisks indicate change of media with fresh Retro94. FIG. 3D shows bright field images of CPE associated with infections in FIG. 3C. FIG. 3E shows the viability of cells treated with DMSO or Retro94 for 4, 9 and 15 days. Bright field images of cell monolayers at 4 days post treatment are shown below graph. Brefeldin A was included as a positive control for cell death. Values in FIGS. 3A and 3C are from one representative experiment.

FIG. 4A shows a Western blot analysis of uninfected cells (Mock) or HCMV-infected cells (MOI=3) treated with DMSO or Retro94 (10 μM) at 24, 48, 72 and 96 hpi. FIG. 4B shows the localization of viral proteins in HCMV-infected cells at 96 hpi in presence of DMSO or Retro 94 (10 μM). Viral proteins detected by tagging with GFP (pp150), mCherry (pp28) or by immunofluorescence (gB). FIG. 4C shows the immunofluorescence detection of the viral protein pp28 in miSTX5 cells (MOI=3) at 96 hpi with or without doxycycline (10 μg/ml). FIGS. 4D-4E show the immunofluorescence detection of (FIG. 4C) STX5, (FIG. 4D) cellular organelle markers (GM130, p230, EEA1) and (FIG. 4E) STX5-interacting Qb SNAREs GS27 and GS28 (green) in uninfected (Mock) and HCMV-infected cells (MOI=3) treated with DMSO or Retro94 at 96 hpi. pp28-mCherry shown in red for reference. FIGS. 4B-4F show nuclei labeled with DAPI (blue). Scale bars: 10 μm.

FIG. 6A is a graph showing the viral titers at 96 hpi (MOI=3) in cells treated with DMSO (None) or Retro94 added at 2, 24, 48 or 72 hpi. FIG. 6B show images representing morphology of cVAC as detected by pp28-mCherry in cells treated as described in FIG. 6A. Scale bars: 10 μm. Nuclei stained with NucBlue Live Cell Stain (blue). FIG. 6C is a graph showing the viral titers at 96 hpi (MOI=3) in cells treated with increasing concentrations of Retro94 or F-Retro94 at 2 hpi. Values in FIGS. 6A and 6C are from one representative experiment.

FIG. 7A is a graph showing viral titers at 15 dpi of fibroblasts infected with various strains of HCMV (MOI=0.05) and treated with DMSO or Retro94 at 2 hpi. Media was changed and fresh Retro94 was added at 6 dpi. Bright field images representing CPE of above infections shown at right. FIG. 7B show HCMV-infected ARPE-19 cells (TB40, MOI=3) at 21 dpi treated with DMSO or Retro94 (10 μm). Infected cells detected by monitoring mCherry (red) expressed by TB40 virus. Scale bars: 1 mm. The table below images show number of foci detected, average area and standard error of the mean. $P<0.00001$. FIG. 7C is a graph showing the viral titers at 6 dpi of MCMV-infected fibroblasts treated with DMSO or Retro94 at 2 hpi. Values in FIGS. 7A and 7C are from one representative experiment.

FIG. 8A is qRT-PCR of STX7 and STX16 from RNA samples harvested from uninfected or HCMV-infected cells at the times indicated. FIG. 8B is an immunofluorescence analysis showing GS15 (green) localization in uninfected cells (Mock) or at 96 hpi relative to pp28 (red). Nuclei labeled with DAPI (blue). Scale bars: 10 μm.

FIG. 10A shows a virus titer analysis of HSV (MOI=3) in DMSO control (No drug) (shaded or black bar) or cells treated with Retro94 (non-shaded or white bar). Samples were harvested at 24 hpi. Representative data shown are from independent replicates. FIG. 10B provides a table showing low nanomolar EC50 values of Retro94F against other herpesviruses.

FIG. 11A provides a table showing EC50 values of Retro94F against a range of viruses from diverse families. FIG. 11B shows growth curve analysis of Zika virus (MOI=5) in vehicle treated (DMSO) or Retro94F-treated cells. Samples were harvested at 24, 48 and 72 hpi. Data shown is from one independent replicates.

FIG. 12A shows viral titers at 6 dpi of MCMV-infected fibroblasts treated with DMSO or Retro94. FIG. 12B shows subconfluent monolayers of Balb/c A31 cells were infected with MuPyV (MOI 0.1) for 1 h at 4° C., then incubated at 37° C. in the absence or presence of the indicated concentration of Retro94F or DABL-NM for 6 days. X100.

FIGS. 13A and 13B, Mice were treated with 250 mg Retro-2.1 or vehicle control one hour prior to infection with $2\times10^4$ PFU MuPyV, then daily until day 4 p.i. FIG. 13A shows Serum creatinine levels from mice at day 4 and day 30 p.i. FIG. 13B shows blood urea nitrogen (BUN) levels from mice at day 4 and day 30 p.i.

FIGS. 14A and 14B show the results of the percent of immune cell populations in the spleen (FIG. 14A) and kidney (FIG. 14B) analyzed at day 8 post infection between vehicle- or Retro94F-treated mice. FIG. 14C shows the percent of MuPyV-specific CD8 T cells in the kidneys at day 8 (acute infection) or day 30 (persistent infection). FIGS. 14D-14E show the phenotype of MuPyV-specific CD8 T cells, analyzed at day 8 or day 30 post infection. KLRG1hi CD127lo (FIG. 14D) cells are short-lived effector cells, while KLRG1lo CD127hi (FIG. 14E) cells are memory-precursor effector cells.

FIG. 15A illustrates the chromatographic separation of DABL-CM enantiomers. FIG. 15B illustrates the configuration of the stereo center in position 2 of the DABL-CM enantiomers. FIG. 15C illustrates the chromatographic separation of DABL-NM enantiomers. FIG. 15D illustrates the chromatographic separation of DABL-CN enantiomers. FIG. 15E illustrates the chromatographic separation of DABL-N enantiomers.

DETAILED DESCRIPTION

Figures 1A, 1B, 1C, 1D, 1E, 1F, 1G:
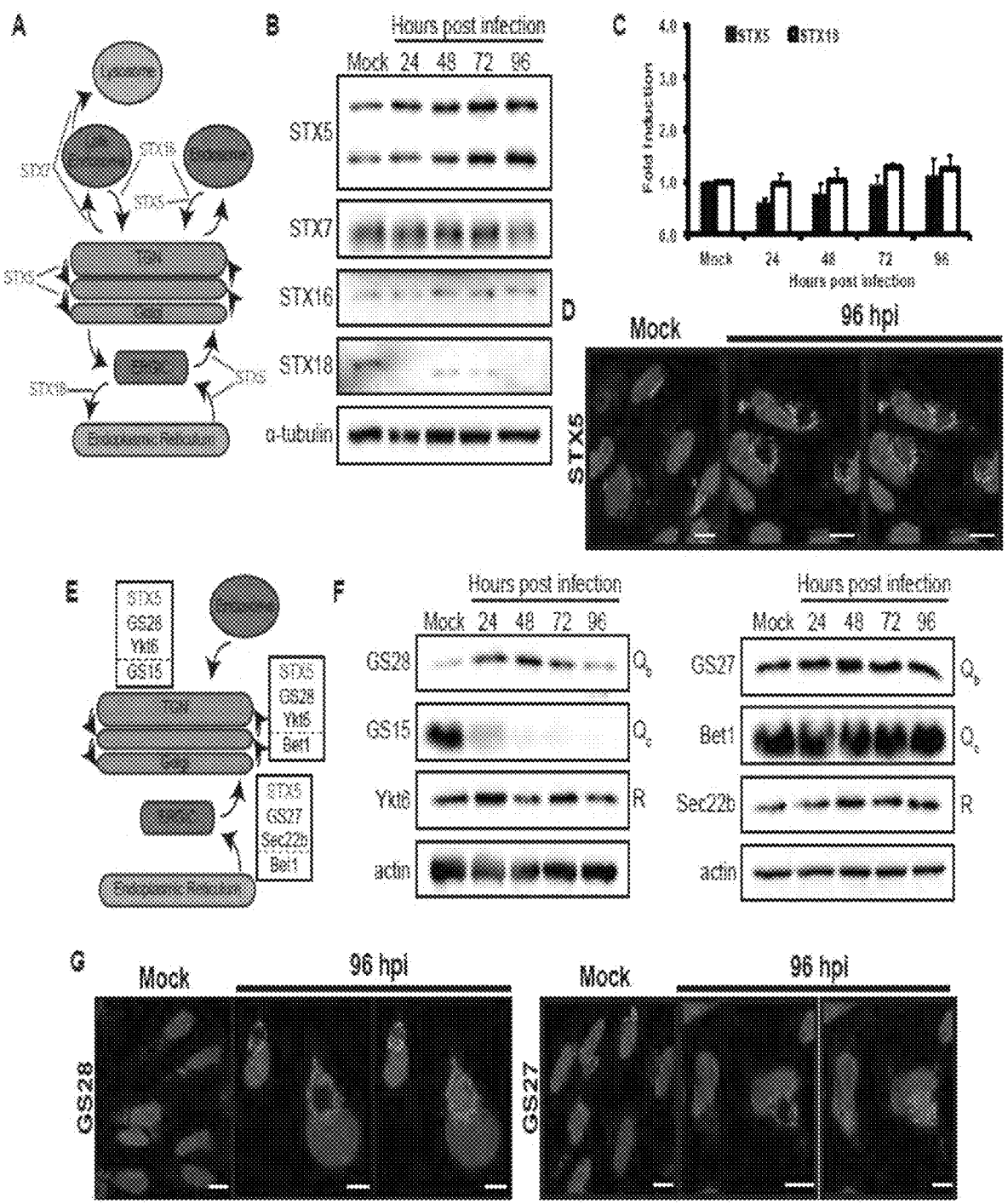
FIGS. 1A-1G show HCMV regulation of Golgi SNAREs during infection.

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events. Furthermore, not all illustrated acts or events are required to implement a methodology in accordance with the present invention.

Definitions

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

As used herein, the terms "comprising," "comprise" or "comprised," and variations thereof, in reference to defined or described elements of an item, composition, apparatus, method, process, system, etc. are meant to be inclusive or open ended, permitting additional elements, thereby indicating that the defined or described item, composition, apparatus, method, process, system, etc. includes those specified elements—or, as appropriate, equivalents thereof—and that other elements can be included and still fall within the scope/definition of the defined item, composition, apparatus, method, process, system, etc.

As used in this specification and the appended claims, the term "or" is generally employed in its sense including "and/or" unless the content clearly dictates otherwise.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value or range. Alternatively, particularly with respect to biological systems or processes, the term can mean within an order of magnitude within 5-fold, and also within 2-fold, of a value. Where particular values are described in the application and claims, unless otherwise stated the term "about" meaning within an acceptable error range for the particular value should be assumed.

The terms, "compound" and "compounds" as used herein refers to a compound encompassed by the generic formulae disclosed herein, any subgenus of those generic formulae, and any forms of the compounds within the generic and subgeneric formulae. Unless specified otherwise, the term further includes the racemates and stereoisomers, of the compound or compounds.

The term "lower" as used herein refers to a group having between one and six carbons.

The term "alkyl" as used herein refers to a saturated straight, branched, or cyclic, primary, secondary, or tertiary hydrocarbon having from one to about fifty carbon atoms, typically $C_1$ to $C_{10}$, and specifically includes methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The term includes both substituted and unsubstituted alkyl groups. Alkyl groups can be optionally substituted with one or more moieties including, but not limited to: halogens, halides, alkylhalides, lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed, hydroxyl, amino, alkylamino, arylamino, aryloxy, nitro, cyano, sulfonic acid, sulfate, phosphonic acid, phosphate, or phosphonate, or as known to those skilled in the art, for example, as taught in T. W. Greene and P. G. M. Wuts, "Protective Groups in Organic Synthesis," $3^{rd}$ ed., John Wiley & Sons, 1999, hereby incorporated by reference. An alkyl group may contain one or more O, S, S(O), or $S(O)_2$ moieties. Examples of "alkyl" as used herein include, but are not limited to, methyl, ethyl, propyl, decyl, undecyl, octadecyl, nonadecyl, eicosyl, heneicosyl, decosyl, tricosyl, tetracosyl, and pentacosyl, n-butyl, t-butyl, n-pentyl, isobutyl, and isopropyl, and the like. In some embodiments the alkyl comprises 1, 2, 3, 4, 5, 6, 7, 8, 9, 10, 11, or 12 carbon atoms.

As used herein, "cycloalkyl" (used interchangeably with "aliphatic cyclic" herein) refers to an alicyclic hydrocarbon group optionally possessing one or more degrees of unsaturation, having from about three to about fifty carbon atoms, optionally substituted with substituents, for example: halogens, halides, alkylhalides, selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. "Cycloalkyl" includes by way of example cyclopropyl, cyclobutyl, cyclopentyl, cyclohexyl, cycloheptyl, or cyclooctyl, and the like.

The terms "heterocycle" and "heterocyclic" as used herein are used interchangeably to refer to a three to about twelve-membered heterocyclic ring optionally aromatic or possessing one or more degrees of unsaturation, containing one or more heteroatomic substitutions, for example: —S—, —SO—, —SO$_2$—, —O—, or —N— and substituents including, but not limited to, halogens, halides, alkylhalides lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring optionally may be fused to one or more of another "heterocyclic," cycloalkyl or aryl ring(s). The term also includes fused ring heteroclyclic compounds, such as 5- and 6-membered fused heterocyclic compounds.

The term "alkenyl" as used herein refers to an unsaturated straight, branched, or cyclic, primary, secondary, or tertiary hydrocarbon of typically $C_1$ to $C_{10}$, that has one or more double bonds therein where the double bond can be unconjugated or conjugated to another unsaturated group (e.g., a polyunsaturated alkenyl) and can be unsubstituted or substituted, with multiple degrees of substitution being allowed. For example, halides, alkylhalides, lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkenyl" group may contain one or more O, S, S(O), or S(O)$_2$ moieties. For example, and without limitation, the alkenyl can be vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl, decenyl, undecenyl, dodecenyl, heptadecenyl, octadecenyl, nonadecenyl, eicosenyl, heneicosenyl, docosenyl, tricosenyl, tetracisenyl, pentacosenyl, phytyl, the branched chain isomers thereof, and polyunsaturated alkenes including octadec-9,12,-dienyl, octadec-9,12,15-trienyl, and eicos-5,8,11,14-tetraenyl. Alkenyl groups can be optionally substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate.

The term "alkynyl" refers to an unsaturated straight, branched, or cyclic, primary, secondary, or tertiary hydrocarbon having from about two to about fifty carbons, typically $C_1$ to $C_{10}$, and at least one carbon-carbon triple bond, optionally substituted with substituents comprising, hydroxyl, alkylamino, arylamino, alkoxy, aryloxy, nitro, cyano, sulfonic acid, sulfate, phosphonic acid, phosphate, phosphonate, lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkynyl" group may contain one or more O, S, S(O), or S(O) 2 moieties.

The terms "alkylamino" or "arylamino" as used herein refer to an amino group that has one or two alkyl or aryl substituents, respectively.

The term "aryl" as used herein refers to phenyl, biphenyl, or naphthyl. The term includes both substituted and unsubstituted moieties and includes for example, an optionally substituted benzene ring or an optionally substituted benzene ring system fused to one or more optionally substituted benzene rings, with multiple degrees of substitution being allowed. The aryl group can also be substituted with one or more moieties comprising: hydroxyl, amino, alkylamino, arylamino, alkoxy, aryloxy, nitro, cyano, sulfonic acid, sulfate, phosphonic acid, phosphate, or phosphonate. Substituents include, but are not limited to, lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, amino sulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Examples of aryl include, but are not limited to, phenyl, 2-napthyl, 1-naphthyl, 1-anthracenyl, and the like.

The term "alkaryl" as used herein refers to an alkyl group with an aryl substituent.

The term "acyl" as used herein refers to a carboxylic acid ester in which the non-carbonyl moiety of the ester group is selected from straight, branched, or cyclic alkyl or lower alkyl, alkoxyalkyl including methoxymethyl, aralkyl including benzyl, aryloxyalkyl such as phenoxymethyl, aryl including phenyl optionally substituted with halogen (F, Cl, Br, I), $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxytrityl, substituted benzyl, trialkylsilyl (e.g. dimethyl-t-butylsilyl) or diphenylmethylsilyl. Aryl groups in the esters optimally comprise a phenyl group.

As used herein, the term "alkoxy" refers to an optionally substituted straight or branched chain alkyl —O— group wherein alkyl is as previously defined. For example, C1-10 alkoxy means a straight or branched alkoxy containing at least 1, and at most 10, carbon atoms. Examples of "alkoxy" as used herein include, but are not limited to, methoxy, ethoxy, propoxy, prop-2-oxy, butoxy, but-2-oxy, 2-methylprop-1-oxy, 2-methylprop-2-oxy, pentoxy and hexyloxy. A C1-4 alkoxy group is preferred, for example methoxy, ethoxy, propoxy, prop-2-oxy, butoxy, but-2-oxy or 2-methylprop-2-oxy. As used herein, the term "aryloxy" refers to an optionally substituted aryl-O-group wherein aryl is as previously defined. Exemplary aryloxy groups include, but are not limited to, phenoxy (phenyl-O—).

As used herein, the term "heteroaryl" refers to an optionally substituted aryl ring system wherein, in at least one of the rings, one or more of the carbon atom ring members is independently replaced by a heteroatom group selected from the group consisting of S, O, N, and NH, or NR wherein aryl is as previously defined and R is an optional substitutent as defined herein. Heteroaryl groups having a total of from about 5 to about 14 carbon atom ring members and heteroatom ring members (and all combinations and subcombinations of ranges and specific numbers of carbon and heteroatom ring members) are preferred. Heteroaryl groups having a total of from about 5 to about 10 carbon atom ring members and heteroatom ring members (and all combinations and subcombinations of ranges and specific numbers of carbon and heteroatom ring members) are more preferred. Exemplary heteroaryl groups include, but are not limited to, pyrryl, furyl, pyridyl, pyridine-N-oxide, 1,2,4-thiadiazolyl, pyrimidyl, thienyl, isothiazolyl, imidazolyl, tetrazolyl, pyrazinyl, pyrimidyl, quinolyl, isoquinolyl, thiophenyl, benzothienyl, isobenzofuryl, pyrazolyl, indolyl, purinyl, carbazolyl, benzimidazolyl, and isoxazolyl. Heteroaryl may be attached to the rest of the molecule via a carbon or a heteroatom.

As used herein, the term "heteroarylalkyl" refers to an optionally substituted ring system comprising an alkyl radical bearing a heteroaryl substituent, each as defined above, having at least 6 carbon atoms, for example, from about 6 to about 25 carbon atoms (and all combinations and subcombinations of ranges and specific numbers of carbon atoms therein).

As used herein, the term "heteroaryl" refers to an optionally substituted aryl ring system wherein, in at least one of the rings, one or more of the carbon atom ring members is independently replaced by a heteroatom group selected from the group consisting of S, O, N, and NH, or NR wherein aryl is as previously defined and R is an optional substituent as defined herein. In some embodiments heteroaryl groups have a total of from about 5 to about 14 carbon atom ring members and heteroatom ring members (and all combinations and subcombinations of ranges and specific numbers of carbon and heteroatom ring members). Heteroaryl groups having a total of from about 5 to about 10 carbon atom ring members and heteroatom ring members (and all combinations and subcombinations of ranges and specific numbers of carbon and heteroatom ring members) are also preferred. Exemplary heteroaryl groups include, but are not limited to, pyrryl, furyl, pyridyl, pyridine-N-oxide, 1,2,4-thiadiazolyl, pyrimidyl, thienyl, isothiazolyl, imidazolyl, tetrazolyl, pyrazinyl, pyrimidyl, quinolyl, isoquinolyl, thiophenyl, benzothienyl, isobenzofuryl, pyrazolyl, indolyl, purinyl, carbazolyl, benzimidazolyl, and isoxazolyl. Heteroaryl may be attached to the rest of the. molecule via a carbon or a heteroatom.

As used herein, the term "heteroarylalkyl" refers to an optionally substituted ring system comprising an alkyl radical bearing a heteroaryl substituent, each as defined above, having from about 6 to about 50 carbon atoms (and all combinations and subcombinations of ranges and specific numbers of carbon atoms therein), with from about 6 to about 25 carbon atoms being preferred. Non-limiting examples include 2-(1H-pyrrol-3-yl)ethyl, 3-pyridylmethyl, 5-(2H-tetrazolyl)methyl, and 3-(pyrimidin-2-yl)-2-methylcyclopentanyl.

As used herein, the term "heterocycloalkyl," "heterocyclic ring" and "heterocyclyl" each refer to an optionally substituted ring system composed of a cycloalkyl radical wherein, in at least one of the rings, one or more of the carbon atom ring members is independently replaced by a heteroatom group selected. From the group consisting of O, S, N, and NH, or NR wherein cycloalkyl is as previously defined and R is an optional substituent as defined herein. Heterocycloalkyl ring systems having a total of from about 3 to about 14 carbon atom ring members and heteroatom ring members (and all combinations and subcombinations of ranges and specific numbers of carbon and heteroatom ring members). In other embodiments, the heterocyclic groups may be fused to one or more aromatic rings. In yet another embodiment, the heterocyclic groups may be fused heterocyclic compounds. In yet other embodiments, heterocycloalkyl moieties are attached via a ring carbon atom to the rest of the molecule. Exemplary heterocycloalkyl groups include, but are not limited to, azepanyl, tetrahydrofuranyl, hexahydropyrimidinyl, tetrahydrothienyl, piperidinyl, pyrrolidinyl, isoxazolidinyl, isothiazolidinyl, pyrazolidinyl, oxazolidinyl, imidazolidinyl, diazolidinyl, piperazinyl, 2-oxo-morpholinyl, morpholinyl, 2-oxo-piperidinyl, piperadinyl, decahydroquinolyl, octahydrochromenyl, octahydrocyclopentapyranyl, 1,2,3,4,-tetrahydroquinolyl, 1,2,3,4-tetrahydroquinazolinyl, octahydro-[2]pyridinyl, decahydrocyclooctafuranyl, 1,2,3,4-tetrahydroisoquinolyl, 2-oxoimidazolidinyl, and imidazolidinyl. In some embodiments, two moieties attached to a heteroatom may be taken together to form a heterocycloalkyl ring. In certain of these embodiments, 1 or 2 of the heterocycloalkyl ring carbon atoms may be replaced by other moieties which contain either one (—O—, —S—, —N(R)—) or two (—N(R)—C(=O)—, or —C(=O)N(R)—) ring replacement atoms. When a moiety containing one ring replacement atom replaces a ring carbon atom, the resultant ring, after replacement of a ring atom by the moiety, will contain the same number of ring atoms as the ring before ring atom replacement. When a moiety containing two ring replacement atoms replaces a ring carbon atom, the resultant ring after replacement will contain one more ring atom than the ring prior to replacement by the moiety. For example, when a piperidine ring has one of its ring carbon atoms replaced by —N(R)C(=O)—, the resultant ring is a 7-membered ring containing 2 ring nitrogen atoms and the carbon of a carbonyl group in addition to 4 other carbon ring atoms ($CH_2$ groups) from the original piperidine ring. In general, the ring system may be saturated or may be partially unsaturated, i.e., the ring system may contain one or more non-aromatic C—C or C—N double bonds.

"Cycloaliphatic" means a saturated or unsaturated, non-aromatic hydrocarbon moiety having from 1 to 3 rings, each ring having from 3 to 8 carbon atoms. "Cycloalkyl" means a cycloaliphatic moiety in which each ring is saturated. "Cyclo-alkenyl" means a cycloaliphatic moiety in which at least one ring has at least one carbon-carbon double bond. "Cycloalkynyl" means a cycloaliphatic moiety in which at least one ring has at least one carbon-carbon triple bond. By way of illustration, cycloaliphatic moieties include, but are not limited to, cyclopropyl, cyclobutyl, cyclopentyl, cyclopentenyl, cyclohexyl, cyclohexenyl, cycloheptyl, cyclooctyl, and adamantyl. Preferred cycloaliphatic moieties are cycloalkyl ones, especially cyclopropyl, cyclobutyl, cyclopentyl, and cyclohexyl. "Cycloalkylene" means a divalent counterpart of a cycloalkyl group.

"Heterocycloaliphatic" means a cycloaliphatic moiety wherein, in at least one ring thereof, up to three carbons have been replaced with a heteroatom independently selected from N, O, or S, where the N and S optionally may be oxidized and the N optionally may be quaternized. Similarly, "heterocycloalkyl," "heterocycloalkenyl," and "heterocycloalkynyl" means a cycloalkyl, cycloalkenyl, or cycloalkynyl moiety, respectively, in which at least one ring thereof has been so modified. Exemplary heterocycloaliphatic moieties include aziridinyl, azetidinyl, 1,3-dioxanyl, oxetanyl, tetrahydrofuryl, pyrrolidinyl, piperidinyl, piperazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolanyl, tetrahydro-1,1-dioxothienyl, 1,4-dioxanyl, thietanyl, and the like. "Heterocycloalkylene" means a divalent counterpart of a heterocycloalkyl group.

Arylalkyl," (heterocycloaliphatic)alkyl," "arylalkenyl," "arylalkynyl," "biarylalkyl," and the like mean an alkyl, alkenyl, or alkynyl moiety, as the case may be, substituted with an aryl, heterocycloaliphatic, biaryl, etc., moiety, as the case may be, with the open (unsatisfied) valence at the alkyl, alkenyl, or alkynyl moiety, for example as in benzyl, phenethyl, N-imidazoylethyl, N-morpholinoethyl, and the like. Conversely, "alkylaryl," "alkenylcycloalkyl," and the like mean an aryl, cycloalkyl, etc., moiety, as the case may be, substituted with an alkyl, alkenyl, etc., moiety, as the case may be, for example as in methylphenyl (tolyl) or allylcyclohexyl. "Hydroxyalkyl," "haloalkyl," "alkylaryl," "cyanoaryl," and the like mean an alkyl, aryl, etc., moiety, as the case may be, substituted with one or more of the identified substituent (hydroxyl, halo, etc., as the case may be).

The term "substituted" as used herein refers to substitution with the named substituent or substituents, multiple degrees of substitution being allowed unless otherwise stated.

The term "optionally substituted" means that the group in question may be unsubstituted or it may be substituted one or several times, such as 1 to 3 times or 1 to 5 times. For example, an alkyl group that is "optionally substituted" with 1 to 5 chloro atoms, may be unsubstituted, or it may contain 1, 2, 3, 4, or 5 chlorine atoms. Typically, substituted chemical moieties include one or more substituents that replace hydrogen. Exemplary substituents include, for example, halo (e.g., F, Cl, Br, I), amino ($NH_2$), alkyl, alkylamino, cycloalkyl, alkylcycloalkyl, alkenyl, alkynyl, haloalkyl including trifluoroalkyl, aralkyl, aryl, heteroaryl, heteroaryllalkyl, spiroalkyl, heterocyclyl, heterocycloalkyl, hydroxyl (—OH), alkoxyl, aryloxyl, aralkoxyl, nitro (—$NO_2$), cyano (—CN), amino (—$NH_2$), N-substituted amino (—NHR"), N,N-disubstituted amino (—N(R")R"), carboxyl (—COOH), —C(=O)R", —OR", —C(=O)OR", —C(=O)$NHSO_2R$", —NHC(=O)R", aminocarbonyl (—C(=O)$NH_2$), N-substituted aminocarbonyl (C(=O)NHR"), N,N-disubstituted aminocarbonyl (—C(=O)N(R")R"), thiolato (SR"), sulfonic acid and its esters (—$SO_3R$"), phosphonic acid and its mono-ester (—P(=O)(OR")(OH) and di-esters (—P(=O)(OR")(OR"), —S(=O)$_2R$", —S(=O)$_2NH_2$, —S(=O)$_2NHR$", —S(=O)$_2NR$"R", —$SO_2NHC$(=O)R", NHS(=O)$_2R$", —NR"S(=O)$_2R$", —$CF_3$, —$CF_2CF_3$, —NHC(=O)NHR", —NHC(=O)NR"R", —NR"C(=O)NHR", —NR"C(=O)NR"R", —NR"C(=O)R" and the like. In relation to the aforementioned substituents, each moiety "R" can be, independently, any of H, alkyl, cycloalkyl, alkenyl, aryl, aralkyl, heteroaryl, or heterocycloalkyl, or when (R"(R")) is attached to a nitrogen atom, R" and R" can be taken together with the nitrogen atom to which they are attached to form a 4- to 8-membered nitrogen heterocycle, wherein the heterocycloalkyl ring is optionally interrupted by one or more additional —O—, —S—, —SO, —$SO_2$—, —NH—, —N(alkyl)-, or —N(aryl)groups, for example. In certain embodiments, chemical moieties are substituted by at least one optional substituent, such as those provided hereinabove. In the present invention, when chemical moieties are substituted with optional substituents, the optional substituents are not further substituted unless otherwise stated. For example, when an R group is an alkyl moiety, it is optionally substituted, based on the definition of "alkyl" as set forth herein. In some embodiments, when R is alkyl substituted with optional aryl, the optional aryl substituent is not further substituted.

By way of illustration, substituents include, but are not limited to, alkyl (e.g. methyl, ethyl), alkylamino, alkenyl (especially allyl), alkynyl, aryl, heteroaryl, cycloaliphatic, heterocycloaliphatic, halo (especially fluoro), haloalkyl (especially trifluoromethyl), hydroxyl, hydroxyalkyl (especially hydroxyethyl), cyano, nitro, alkoxy, —O(hydroxyalkyl), —O(haloalkyl) (especially —$OCF_3$), —O(cycloalkyl), —O(heterocycloalkyl), —O(aryl), alkylthio, arylthio, =O, =NH, =N(alkyl), =NOH, =NO (alkyl), —C(=O)(alkyl), —C(=O)H, —$CO_2H$, —C(=O)NHOH, —C(=O)O(alkyl), —C(=O)O(hydroxyalkyl), —C(=O)$NH_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)$NH_2$, —OC(=O)NH(alkyl), —OC(=O)N(alkyl)$_2$, azido, —$NH_2$, —NH(alkyl), —N(alkyl)$_2$, —NH(aryl), —NH(hydroxyalkyl), —NHC(=O)(alkyl), —NHC(=O)H, —NHC(=O)$NH_2$, —NHC(=O)NH(alkyl), —NHC(=O)N(alkyl)$_2$, —NHC(=NH)$NH_2$, —$OSO_2$(alkyl), —SH, —S(alkyl), —S(aryl), —S(cycloalkyl), —S(=O)alkyl, —$SO_2$(alkyl), —$SO_{12}NH_2$, —$SO_2NH$(alkyl), —$SO_2N$(alkyl)$_2$, and the like.

Where the moiety being substituted is an aliphatic moiety, substituents include, but not limited to: aryl, heteroaryl, cycloaliphatic, heterocycloaliphatic, halo, hydroxyl, cyano, nitro, alkoxy, —O(hydroxyalkyl), —O(haloalkyl), —O(cycloalkyl), —O(heterocycloalkyl), —O(aryl), alkylthio, arylthio, =O, =NH, =N(alkyl), =NOH, =NO(alkyl), —$CO_2H$, —C(=O)NHOH, —C(=O)O(alkyl), —C(=O)O(hydroxyalkyl), —C(=O)$NH_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)$NH_2$, —OC(=O)NH(alkyl), —OC(=O)N(alkyl)$_2$, azido, —$NH_2$, —NH(alkyl), —N(alkyl)$_2$, —NH(aryl), —NH(hydroxyalkyl), —NHC(=O)(alkyl), —NHC(=O)H, —NHC(=O)$NH_2$, —NHC(=O)NH(alkyl), —NHC(=O)N(alkyl)$_2$, —NHC(=NH)$NH_2$, —$OSO_2$(alkyl), —SH, —S(alkyl), —S(aryl), —S(cycloalkyl), —S(=O)alkyl, —$SO_2$(alkyl), —$SO_2NH_2$, —$SO_2NH$(alkyl), and —$SO_2N$(alkyl)$_2$. More preferred substituents are halo, hydroxyl, cyano, nitro, alkoxy, —O(aryl), =O, =NOH, =NO(alkyl), —OC(=O)(alkyl), —OC(=O)O(alkyl), —OC(=O)$NH_2$, —OC(=O)NH(alkyl), —OC(=O)N(alkyl)$_2$, azido, —$NH_2$, —NH(alkyl), —N(alkyl)$_2$, —NH(aryl), —NHC(=O)(alkyl), —NHC(=O)H, —NHC(=O)$NH_2$, —NHC(=O)NH(alkyl), —NHC(=O)N(alkyl)$_2$, and —NHC(=NH)$NH_2$. Especially preferred are phenyl, cyano, halo, hydroxyl, nitro, $C_1$-$C_4$alkyoxy, O($C_2$-$C_4$ alkylene)OH, and O($C_2$-$C_4$ alkylene)halo.

Where the moiety being substituted is a cycloaliphatic, heterocycloaliphatic, aryl, or heteroaryl moiety, substituents include, but not limited to: alkyl, alkenyl, alkynyl, halo, haloalkyl, hydroxyl, hydroxyalkyl, cyano, nitro, alkoxy, —O(hydroxyalkyl), —O(haloalkyl), —O(aryl), —O(cycloalkyl), —O(heterocycloalkyl), alkylthio, arylthio, —C(=O)(alkyl), —C(=O)H, —$CO_2H$, —C(=O)NHOH, —C(=O)O(alkyl), —C(=O)O(hydroxyalkyl), —C(=O)$NH_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)$NH_2$, —OC(=O)NH(alkyl), —OC(=O)N(alkyl)$_2$, azido, —$NH_2$, —NH(alkyl), —N(alkyl)$_2$, —NH(aryl), —NH(hydroxyalkyl), —NHC(=O)(alkyl), —NHC(=O)H, —NHC(=O)$NH_2$, —NHC(=O)NH(alkyl), —NHC(=O)N(alkyl)$_2$, —NHC(=NH)$NH_2$, —$OSO_2$(alkyl), —SH, —S(alkyl), —S(aryl), —S(cycloalkyl), —S(=O)alkyl, —$SO_2$(alkyl), —$SO_2NH_2$, —$SO_2NH$(alkyl), and —$SO_2N$(alkyl)$_2$. In some embodiments, substituents are alkyl, alkenyl, halo, haloalkyl, hydroxyl, hydroxyalkyl, cyano, nitro, alkoxy, —O(hydroxyalkyl), —C(=O)(alkyl), —C(=O)H, —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH(alkyl), —OC(=O)N(alkyl)$_2$, —NH$_2$, —NH(alkyl), —N(alkyl)$_2$, —NH(aryl), —NHC(=O)(alkyl), —NHC(=O)H, —NHC(=O)NH$_2$, —NHC(=O)NH(alkyl), —NHC(=O)N(alkyl)$_2$, and —NHC(=NH)NH$_2$. In some embodiments, substituents are C$_1$-C$_4$ alkyl, cyano, nitro, halo, and C$_1$-C$_4$alkoxy.

When any variable occurs more than one time in any constituent or formula for a compound, its definition at each occurrence is independent of its definition at every other occurrence. Thus, for example, if the R$_5$ group is shown to be substituted with 0-2 substituents, then said group may optionally be substituted with up to two substituents and each substituent is selected independently from the definition of optionally substituted defined above. Also, combinations of substituents and/or variables are permissible only if such combinations result in stable compounds.

When a bond to a substituent is shown to cross a bond connecting two atoms in a ring, then such substituent may be bonded to any atom on the ring having an attached hydrogen atom. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, a "pharmaceutically acceptable" component/carrier etc is one that is suitable for use with humans and/or animals without undue adverse side effects (such as toxicity, irritation, and allergic response) commensurate with a reasonable benefit/risk ratio.

As used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used in the manner of this invention. By "therapeutically effective amount" is meant an amount of a compound of the present invention effective to yield the desired therapeutic response. For example, an amount effective to delay the growth of or to cause a cancer, either a sarcoma or lymphoma, or to shrink the cancer or prevent metastasis. The specific safe and effective amount or therapeutically effective amount will vary with such factors as the particular condition being treated, the physical condition of the patient, the type of mammal or animal being treated, the duration of the treatment, the nature of concurrent therapy (if any), and the specific formulations employed and the structure of the compounds or its derivatives.

The term "prodrug" refers to any derivative of a compound of the embodiments that is capable of directly or indirectly providing a compound of the embodiments or an active metabolite or residue thereof when administered to a subject. Particularly favored derivatives and prodrugs are those that increase the bioavailability of the compounds of the embodiments when such compounds are administered to a subject (e.g., by allowing an orally administered compound to be more readily absorbed into the blood) or which enhance delivery of the parent compound to a biological compartment (e.g., the brain or lymphatic system) relative to the parent species. A general overview of prodrugs is provided in T. Higuchi and V. Stella, *Pro-drugs as Novel Delivery Systems*, Vol. 14 of the A.C.S. Symposium Series, and in Edward B. Roche, ed., Bioreversible.

The term "pharmaceutically acceptable salt" refers to pharmaceutically acceptable salts derived from a variety of organic and inorganic counter ions well known in the art and include, by way of example only, sodium, potassium, calcium, magnesium, ammonium, and tetraalkylammonium, and when the molecule contains a basic functionality, salts of organic or inorganic acids, such as hydrochloride, hydrobromide, tartrate, mesylate, acetate, maleate, and oxalate. Suitable salts include those described in P. Heinrich Stahl, Camille G. Wermuth (Eds.), *Handbook of Pharmaceutical Salts Properties*, Selection, and Use; 2002.

"Diagnostic" or "diagnosed" means identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

"Treatment" is an intervention performed with the intention of preventing the development or altering the pathology or symptoms of a disorder. Accordingly, "treatment" refers to both therapeutic treatment and prophylactic or preventative measures. "Treatment" may also be specified as palliative care. Those in need of treatment include those already with the disorder as well as those in which the disorder is to be prevented. In tumor (e.g., cancer) treatment, a therapeutic agent may directly decrease the pathology of tumor cells, or render the tumor cells more susceptible to treatment by other therapeutic agents, e.g., radiation and/or chemotherapy. Accordingly, "treating" or "treatment" of a state, disorder or condition includes: (1) preventing or delaying the appearance of clinical symptoms of the state, disorder or condition developing in a human or other mammal that may be afflicted with or predisposed to the state, disorder or condition but does not yet experience or display clinical or subclinical symptoms of the state, disorder or condition; (2) inhibiting the state, disorder or condition, i.e., arresting, reducing or delaying the development of the disease or a relapse thereof (in case of maintenance treatment) or at least one clinical or subclinical symptom thereof; or (3) relieving the disease, i.e., causing regression of the state, disorder or condition or at least one of its clinical or subclinical symptoms. The benefit to an individual to be treated is either statistically significant or at least perceptible to the patient or to the physician.

The terms "patient", "subject" or "individual" are used interchangeably herein, and refers to a mammalian subject to be treated, with human patients being preferred. In some cases, the methods of the invention find use in experimental animals, in veterinary application, and in the development of animal models for disease, including, but not limited to, rodents including mice, rats, and hamsters; and primates.

Compositions and Methods of Treatment

Despite identification of a number of viral and cellular proteins associated with the cVAC, little is known about the mechanisms governing the gross reorganization of cellular organelles during cVAC formation. A recent siRNA screen of candidate viral proteins identified three HCMV proteins important for cVAC biogenesis: UL48, UL103 and UL94 (Das S, et al. *J Virol.* 2014; 88(16):9086-99). These viral proteins likely act in concert with cellular proteins to direct the events that lead to the formation and maintenance of the cVAC. The contribution of cellular factors to cVAC biogenesis is incompletely defined and only a few cellular proteins have been identified to date, including Rab11, Bicaudal D1, FIP4, BiP and dynein (Buchkovich N J, et al. *J Virol.* 2009; 83(22):11421-8; Buchkovich N J, et al. *J Virol.* 2010; 84(14):7005-17; Indran S V, et al. *J Virol.* 2010; 84(7):3162-77; Krzyzaniak M A, et al. *Traffic.* 2009; 10(10):1439-57). It merits noting that these factors play important roles in trafficking. Investigating a role for additional cellular trafficking proteins will be essential for elucidating the mechanism of cVAC formation.

In addition to the above mentioned viral and cellular proteins, cVAC biogenesis also requires the expression of viral miRNAs (Hook L M, et al. *Cell Host Microbe.* 2014; 15(3):363-73). Interestingly, these miRNAs target multiple factors of the cellular secretory pathway, including both Rab and SNARE (soluble NSF attachment protein receptor) proteins, Rab11A and Rab5C, SNAP23 (synaptosomal-associated protein 23) and VAMP3 (vesicle-associated membrane protein 3). SNARE proteins mediate membrane fusion and are important at most intracellular trafficking steps. As such, it is conceivable that HCMV regulates the cellular SNARE repertoire to bias membrane flow towards generation of the cVAC. In addition to the SNARE proteins identified in the miRNA study, other SNARES are modulated during HCMV infection. Two SNARE proteins associated with exocytosis, syntaxin 3 (STX3) and SNAP23, are required for production and/or release of infectious particles (Liu S T, et al., *Proc Natl Acad Sci USA.* 2011; 108(31): 12869-74. Cepeda V, et al. *Cell Microbiol.* 2011; 13(6):846-58); however, the requirement of SNAP23 for virus release needs to be reconciled with its reported downregulation by HCMV miRNAs (Hook L M, et al. *Cell Host Microbe,* 2014; 15(3):363-73). The essential roles in trafficking of the SNARE proteins make them targets for modulation by HCMV as the virus optimizes conditions for producing infectious virions.

Accordingly, embodiments of the invention are directed to compounds for use in the prevention and/or treatment against viral infections.

In certain embodiments, compounds of the invention are set forth in Formula I:

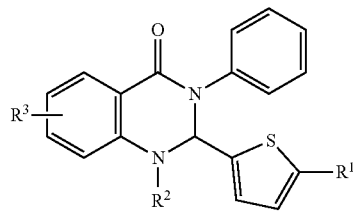

I or a pharmaceutically acceptable salt thereof,
wherein:
$R^1$ comprises H, O, 2-methylthiazol, an aromatic heterocyclic group; or an aromatic heterocyclic group substituted by: a $C_1$-$C_{10}$ alkyl group; a halogen atom; a phenyl group; a phenyl group substituted by one or more of: a $C_1$-$C_{10}$ alkoxy group, and a group —CN, —$NO_2$, —COX and —COOX, X being a $C_1$-$C_4$ alkyl radical; a group —SY, Y being a $C_1$-$C_4$ alkyl group or a phenyl group; —CN; a group —$CH_2$—$N_3$; a group —$CH_2$—$N_3$; an aromatic heterocyclic group selected from the group consisting of furan, thiophene, pyrrole, pyrroline, pyrrolidine, dioxolane, oxazole, thiazole, imidazole, imidazoline, imidazolidine, pyrazole, isoxazole, isothiazole, pyran, pyridine, piperidine, dioxane, morpholine, pyridazine, pyrimidine and pyrazine, each of which is optionally substituted by at least one $C_1$-$C_3$ alkyl radical and/or a group —$CH_2$—$N_3$ thereof; a phenyl group or a phenyl group substituted by a $C_1$-$C_3$ alkoxy group or $NMe_2$; and, $R^2$ is H, OH, $CH_3$, halogen, $C_{1-10}$ alkyl, the $C_{1-10}$ alkyl is unsubstituted or optionally substituted with a functional group selected from the group consisting of H, —OH, —OR', —$NH_2$, —NHR', —$NR'_2$, —SH, —SR', —O—C(O)R', —C(O)R', —$CF_3$, —$OCF_3$, where R' is selected from radicals consisting of H, heteroaryl having 1 to 4 N, O, halogen and/or S atoms, $C_{1-10}$ alkyl, $C_{2-10}$ alkenyl, $C_{2-10}$ alkynyl, $C_{4-10}$ heterocycle and $C_{4-10}$ heteroaryl; and, $R^3$ is hydrogen atom, a halogen atom or a $C_1$-$C_3$ alkoxy group, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, and substituted or unsubstituted heteroaryl, H, —OH, —OR', —$NH_2$, —NHR', —$NR'_2$, —SH, —SR', —O—C(O)R', —C(O)R', $(CH_2)_bNH_2$, $C_{(m+1)}H_{(2m+1)}$, $C_{(m+1)}H_{(2m+1)}NH_2$, $C_{(m+1)}H_{(2m+1)}CONH_2$, $C_{(m+1)}H_{(2m+1)}$, CR'$NH_2$, $C_{(m+1)}H_{(2m+1)}$—$C_{4-20}$ aryl-$C_{(m+1)}H_{(2m+1)}$—$NH_2$, $C_mH_{2m+2}$, $C_{4-20}$ aryl, $C_{1-20}$ alkyl, $C_{1-20}$ alkylamino, alkenyl, $C_{2-20}$ alkynyl, $C_{4-20}$ heterocycle, $C_{4-20}$ heteroaryl, $C_{4-20}$ alkyl heterocycle, $C_{7-20}$ alkyl heteroaryl, $C_{1-20}$ alkyoxyl, where m is an integer from 0 to 10, and b is an integer from 0 to 10, wherein, the $C_{4-20}$ aryl, $C_{1-20}$ alkyl, $C_{2-20}$ alkenyl, $C_{2-20}$ alkynyl, $C_{4-20}$ heterocycle, $C_{4-20}$ heteroaryl, $C_{4-20}$ alkyl heterocycle, $C_{7-20}$ alkyl heteroaryl, $C_{1-20}$ alkyoxyl is unsubstituted or optionally substituted with a functional group comprising H, —OH, —OR', —$NH_2$, —NHR', —$NR'_2$, —SH, —SR', —O—C(O)R', —C(O)R', —$CF_3$, —$OCF_3$, the $C_{4-20}$ aryl, $C_{1-20}$ alkyl, $C_{2-20}$ alkenyl, $C_{2-20}$ alkynyl, $C_{4-20}$ heterocycle, $C_{4-20}$ heteroaryl, $C_{4-20}$ alkyl heterocycle, $C_{7-20}$ alkyl heteroaryl, $C_{1-20}$ alkyoxyl, and the $C_{1-6}$ alkyl is optionally interrupted by one or more O, S, or N atoms, or one or more groups comprising cycloalkyl, $C_{(m+1)}H_{(2m+1)}$, $C_{(m+1)}H_{(2m+1)}NH_2$, CH—C(O)—O—, —O—C(O)—, —C(O)—, —C(O)—NH—, —NH—C(O)—, —NH—C(O)—O— and —O—C(O)—NH—, R' is H, OH, halogen, —$CH_3$, $NO_2$, —$NH_2$, CN, —COOH, heteroaryl having 1 to 4 N, O and/or S atoms, $C_{4-20}$ aryl, $C_{1-10}$ alkyl, $C_{2-10}$ alkenyl, $C_{2-10}$ alkynyl, $C_{4-10}$ heterocycle or $C_{4-10}$ heteroaryl.

In certain embodiments, the compounds comprise:

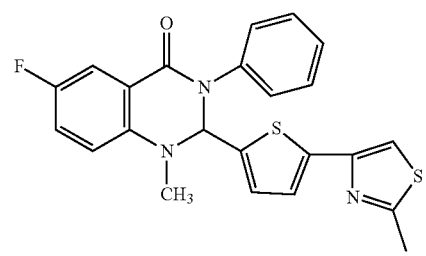

-continued

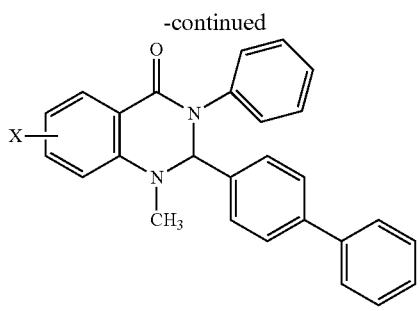

X = Halide, alkyl, aryl

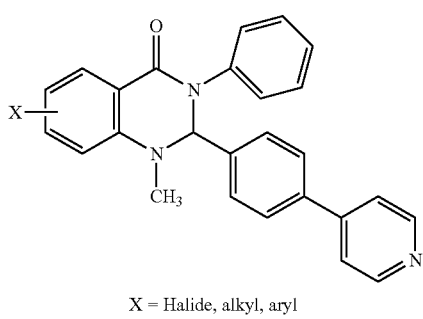

X = Halide, alkyl, aryl

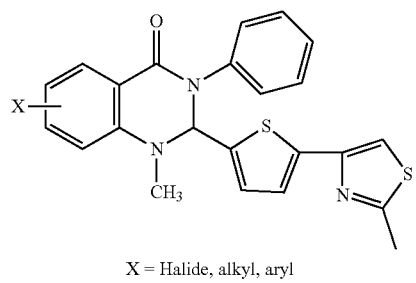

X = Halide, alkyl, aryl

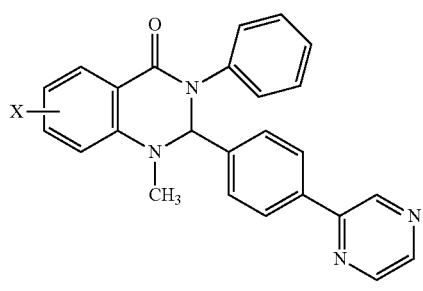

X = Halide, alkyl, aryl

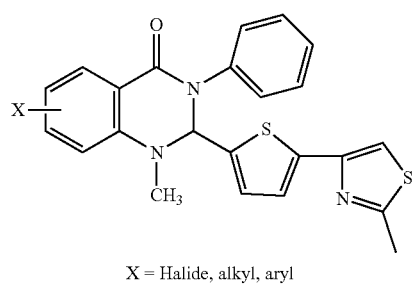

X = Halide, alkyl, aryl

-continued

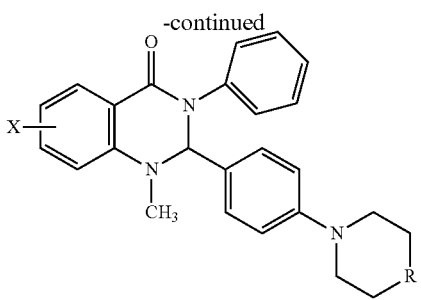

R = N, O, S
X = Halide, alkyl, aryl or a pharmaceutically acceptable salt thereof,
In one embodiment, the compound is:

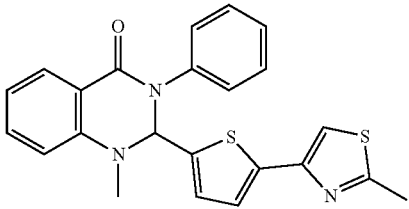 [SMILES: Cc1nc(-c2ccc(C3N(C)c4ccccc4C(=O)N3c3ccccc3)s2)cs1]

1-methyl-2-(5-(2-methylthiazol-4-yl)thiophen-2-yl)-3-phenyl-2,3-dihydroquinazolin-4(1H)-one), analogs, variants, derivatives or pharmaceutically acceptable salts thereof.

In another embodiment, the compound is:

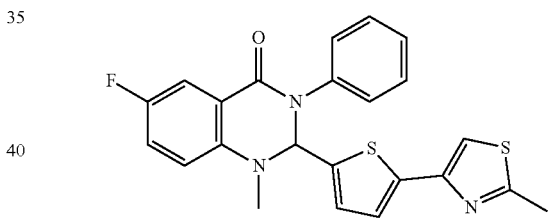

6-Fluoro-1-methyl-2-(5-(2-methylthiazol-4-yl)thiophen-2-yl)-3-phenyl-2,3-dihydroquinazolin-4(1H)-one), analogs, variants, derivatives or pharmaceutically acceptable salts thereof.

In certain embodiments, the compound is set forth in Formula II:

II

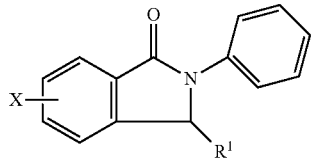

or a pharmaceutically acceptable salt thereof,
wherein:
X is halide, alkyl, aryl,
$R^1$ comprises H, O, 2-methylthiazol, an aromatic heterocyclic group; or an aromatic heterocyclic group substituted by: a $C_1$-$C_{10}$ alkyl group; a halogen atom; a phenyl group; a phenyl group substituted by one or more of: a $C_1$-$C_{10}$ alkoxy group, and a group —CN, —NO₂, —COX and —COOX, X being a C₁-C₄ alkyl radical; a group —SY, Y being a C₁-C₄ alkyl group or a phenyl group; —CN; a group —CH₂—N₃; a group —CH₂—N₃; an aromatic heterocyclic group selected from the group consisting of furan, thiophene, pyrrole, pyrroline, pyrrolidine, dioxolane, oxazole, thiazole, imidazole, imidazoline, imidazolidine, pyrazole, isoxazole, isothiazole, pyran, pyridine, piperidine, dioxane, morpholine, pyridazine, pyrimidine and pyrazine, each of which is optionally substituted by at least one C₁-C₃ alkyl radical and/or a group —CH₂—N₃ thereof; a phenyl group or a phenyl group substituted by a C₁-C₃ alkoxy group or NMe₂.

In certain embodiments, the compounds comprise:

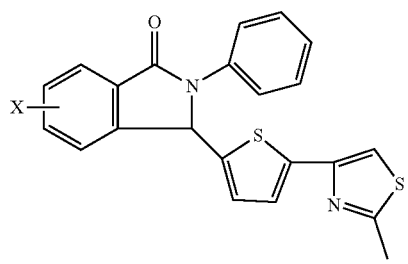

Where X = Halide, alkyl, aryl

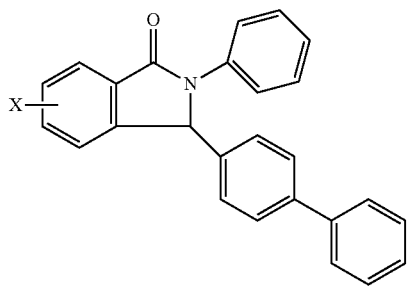

Where X = Halide, alkyl, aryl

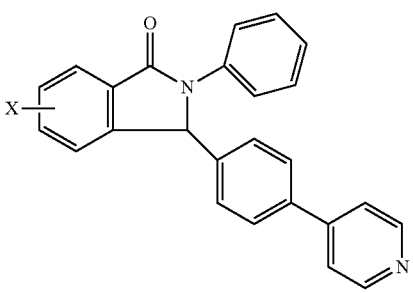

Where X = Halide, alkyl, aryl

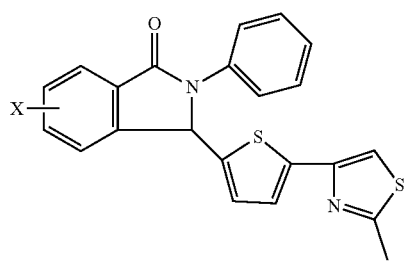

Where X = Halide, alkyl, aryl

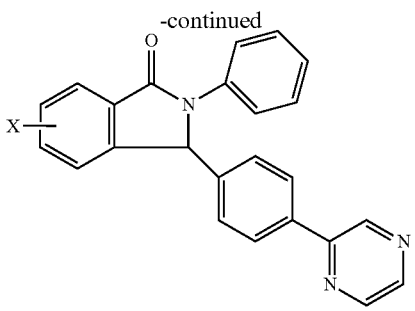

Where X = Halide, alkyl, aryl

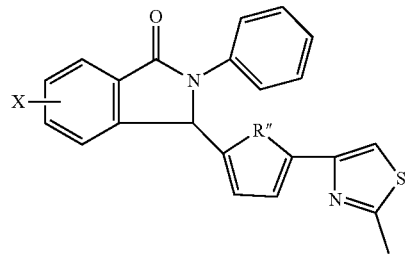

Where X = Halide, alkyl, aryl
Where R' = S, N, O, Se

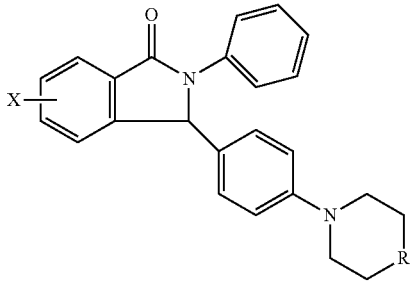

Where R = N, O, S
Where X = Halide, alkyl, aryl or a pharmaceutically acceptable salt thereof.

In certain embodiments, the compounds are set forth in Formula III:

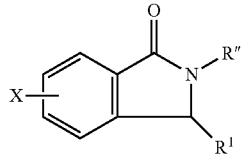

III or a pharmaceutically acceptable salt thereof,
wherein:
X is halide, alkyl, aryl,
R¹ comprises H, O, 2-methylthiazol, an aromatic heterocyclic group; or an aromatic heterocyclic group substituted by: a C₁-C₁₀ alkyl group; a halogen atom; a phenyl group; a phenyl group substituted by one or more of: a C₁-C₁₀ alkoxy group, and a group —CN, —NO₂, —COX and —COOX, X being a C₁-C₄ alkyl radical; a group —SY, Y being a C₁-C₄ alkyl group or a phenyl group; —CN; a group —CH₂—N₃; a group —CH₂—N₃; an aromatic heterocyclic group selected from the group consisting of furan, thiophene, pyrrole, pyrroline, pyrrolidine, dioxolane, oxazole, thiazole, imidazole, imidazoline, imidazolidine, pyrazole, isoxazole, isothiazole, pyran, pyridine, piperidine, dioxane, morpholine, pyridazine, pyrimidine and pyrazine, each of which is optionally substituted by at least one $C_1$-$C_3$ alkyl radical and/or a group —$CH_2$—$N_3$ thereof; a phenyl group or a phenyl group substituted by a $C_1$-$C_3$ alkoxy group or $NMe_2$;

R" is H, OH, $CH_3$, halogen, phenyl, $C_{1-10}$ alkyl, the $C_{1-10}$ alkyl is unsubstituted or optionally substituted with a functional group selected from the group consisting of H, —OH, —OR', —$NH_2$, —NHR', —$NR'_2$, —SH, —SR', —O—C(O) R', —C(O)R', —$CF_3$, —$OCF_3$, where R' is selected from radicals consisting of H, heteroaryl having 1 to 4 N, O, halogen and/or S atoms, $C_{1-10}$ alkyl, $C_{2-10}$ alkenyl, $C_{2-10}$ alkynyl, $C_{4-10}$ heterocycle and $C_{4-10}$ heteroaryl; a $C_1$-$C_4$ alkyl group, or a $C_1$-$C_3$ alkoxy group, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, and substituted or unsubstituted heteroaryl, H, —OH, —OR', —$NH_2$, —NHR', —$NR'_2$, —SH, —SR', —O—C(O)R', —C(O)R', $(CH_2)_b$ $NH_2$, $C_{(m+1)}H_{(2m+1)}$, $C_{(m+1)}H_{(2m+1)}NH_2$, $C_{(m+1)}H_{(2m+1)}$ $CONH_2$, $C_{(m+1)}H_{(2m+1)}$, $CR'NH_2$, $C_{(m+1)}H_{(2m+1)}$—$C_{4-20}$ aryl-$C_{(m+1)}H_{(2m+1)}$—$NH_2$, $C_mH_{2m+2}$, $C_{4-20}$ aryl, $C_{1-20}$ alkyl, $C_{1-20}$ alkylamino, $C_{2-20}$ alkenyl, $C_{2-20}$ alkynyl, $C_{4-20}$ heterocycle, $C_{4-20}$ heteroaryl, $C_{4-20}$ alkyl heterocycle, $C_{7-20}$ alkyl heteroaryl, $C_{1-20}$ alkyoxyl, where m is an integer from 0 to 10, and b is an integer from 0 to 10, wherein, the $C_{4-20}$ aryl, $C_{1-20}$ alkyl, $C_{2-20}$ alkenyl, $C_{2-20}$ alkynyl, $C_{4-20}$ heterocycle, $C_{4-20}$ heteroaryl, $C_{4-20}$ alkyl heterocycle, $C_{7-20}$ alkyl heteroaryl, $C_{1-20}$ alkyoxyl is unsubstituted or optionally substituted with a functional group comprising H, —OH, —OR', —$NH_2$, —NHR', —$NR'_2$, —SH, —SR', —O—C(O)R', —C(O)R', —$CF_3$, —$OCF_3$, the $C_{4-20}$ aryl, $C_{1-20}$ alkyl, $C_{2-20}$ alkenyl, $C_{2-20}$ alkynyl, $C_{4-20}$ heterocycle, $C_{4-20}$ heteroaryl, $C_{4-20}$ alkyl heterocycle, $C_{7-20}$ alkyl heteroaryl, $C_{1-20}$ alkyoxyl, and the $C_{1-6}$ alkyl is optionally interrupted by one or more O, S, or N atoms, or one or more groups comprising cycloalkyl, $C_{(m+1)}H_{(2m+1)}$, $C_{(m+1)}H_{(2m+1)}NH_2$, CH—C(O)—O—, —O—C(O)—, —C(O)—, —C(O)—NH—, —NH—C(O)—, —NH—C(O)—O— and —O—C(O)—NH—, R' is H, OH, halogen, —$CH_3$, $NO_2$, —$NH_2$, CN, —COOH, heteroaryl having 1 to 4 N, O and/or S atoms, $C_{4-20}$ aryl, $C_{1-10}$ alkyl, $C_{2-10}$ alkenyl, $C_{2-10}$ alkynyl, $C_{4-10}$ heterocycle or $C_{4-10}$ heteroaryl.

In certain embodiments, the compounds comprise:

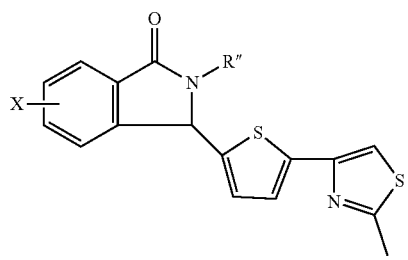

R" = alkyl, aryl, halide
X = Halide, alkyl, aryl

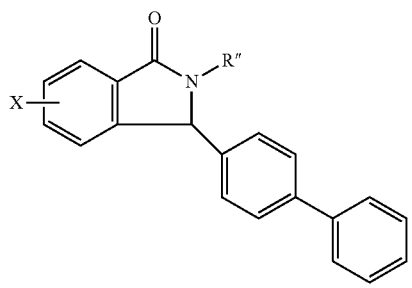

R" = alkyl, aryl, halide
X = Halide, alkyl, aryl

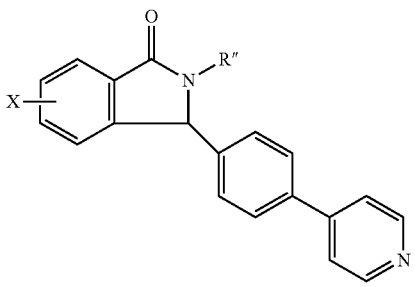

R" = alkyl, aryl, halide
X = Halide, alkyl, aryl

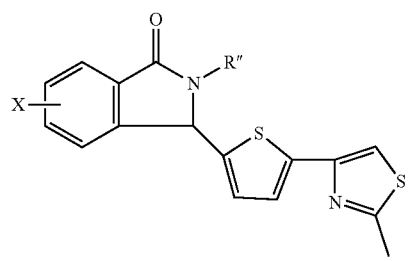

R" = alkyl, aryl, halide
X = Halide, alkyl, aryl

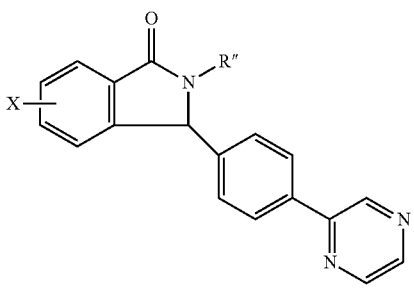

R" = alkyl, aryl, halide
X = Halide, alkyl, aryl

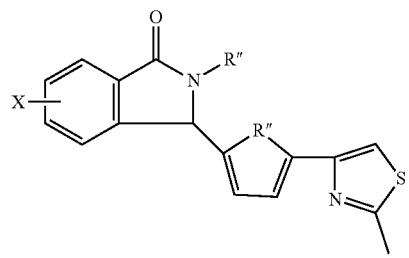

R" = S, N, O, Se
X = Halide, alkyl, aryl

-continued

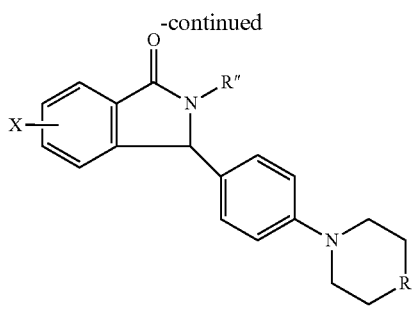

R = N, O, S
R" = alkyl, aryl, halide
X = Halide, alkyl, aryl

In certain embodiments, compounds of the invention are set forth in Formula IV:

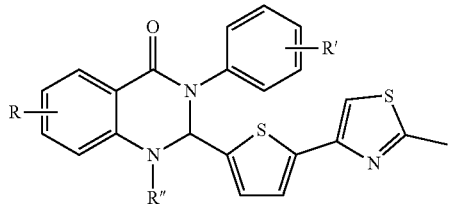

IV derivatives, stereoisomers, racemic or nonrecemic mixture of the stereoisomers, or a pharmaceutically acceptable salt thereof;

wherein R, R'=—CN, —C=CH$_2$, —C≡CH, —NO$_2$, —COOH, -esters, -Amino acids, -peptides, and their corresponding salts;

-Urea, -thiourea, -selenourea, and corresponding conjugates;

-guanidine, -thioguanidine, and corresponding salts and conjugates;

-hetrocycle (5 membered ring, 6 membered ring with N, O, S); and

R"=H, —OH, -acetate, -alkyl, -aryl, -heterocycle (5 membered, 6 membered with N, O, S).

In certain embodiments, compounds of the invention are set forth as derivatives or analogs of Formula IV.

In certain embodiments, compounds of the invention comprise

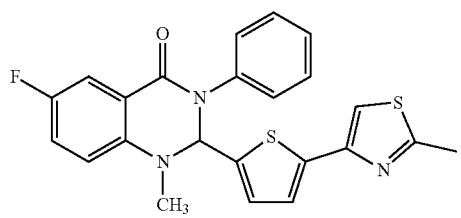 [SMILES: Cc1nc(-c2ccc(C3N(C)c4ccc(F)cc4C(=O)N3c3ccccc3)s2)cs1]

In certain embodiments, compounds of the invention comprise,

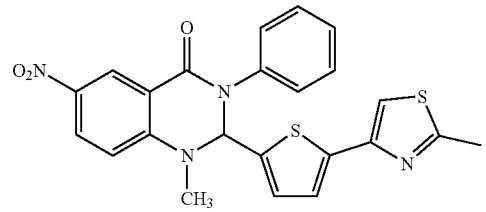 [SMILES: Cc1nc(-c2ccc(C3N(C)c4ccc([N+](=O)[O-])cc4C(=O)N3c3ccccc3)s2)cs1]

In certain embodiments, compounds of the invention comprise,

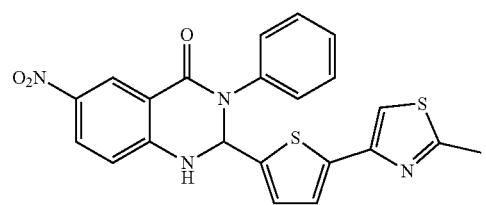 [SMILES: Cc1nc(-c2ccc(C3Nc4ccc([N+](=O)[O-])cc4C(=O)N3c3ccccc3)s2)cs1]

In certain embodiments, compounds of the invention comprise,

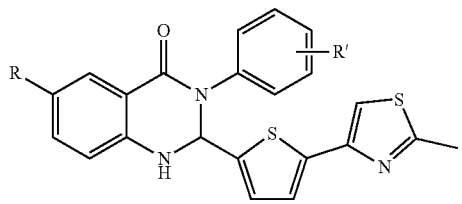

In certain embodiments, compounds of the invention comprise,

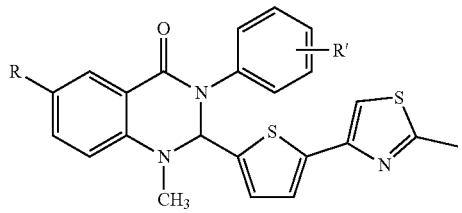

In certain embodiments, a method of method of preventing or treating a virus infection in vivo or in vitro, comprises administering to a subject in need thereof, or contacting a cell with a therapeutically effective amount of a compound set forth in Formula I:

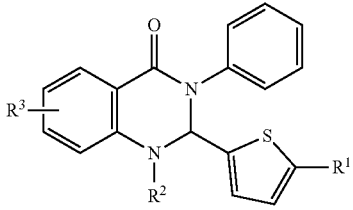

I or a pharmaceutically acceptable salt thereof, wherein: R' comprises H, O, 2-methylthiazol, an aromatic heterocyclic group; or an aromatic heterocyclic group substituted by: a $C_1$-$C_{10}$ alkyl group; a halogen atom; a phenyl group; a phenyl group substituted by one or more of: a $C_1$-$C_{10}$ alkoxy group, and a group —CN, —$NO_2$, —COX and —COOX, X being a $C_1$-$C_4$ alkyl radical; a group —SY, Y being a $C_1$-$C_4$ alkyl group or a phenyl group; —CN; a group —$CH_2$—$N_3$; a group —$CH_2$—$N_3$; an aromatic heterocyclic group selected from the group consisting of furan, thiophene, pyrrole, pyrroline, pyrrolidine, dioxolane, oxazole, thiazole, imidazole, imidazoline, imidazolidine, pyrazole, isoxazole, isothiazole, pyran, pyridine, piperidine, dioxane, morpholine, pyridazine, pyrimidine and pyrazine, each of which is optionally substituted by at least one $C_1$-$C_3$ alkyl radical and/or a group —$CH_2$—$N_3$ thereof; a phenyl group or a phenyl group substituted by a $C_1$-$C_3$ alkoxy group or $NMe_2$; and $R^2$ is H, OH, $CH_3$, halogen, $C_{1-10}$ alkyl, the $C_{1-10}$ alkyl is unsubstituted or optionally substituted with a functional group selected from the group consisting of H, —OH, —OR', —$NH_2$, —NHR', —$NR'_2$, —SH, —SR', —O—C(O)R', —C(O)R', —$CF_3$, —$OCF_3$, where R' is selected from radicals consisting of H, heteroaryl having 1 to 4 N, O, halogen and/or S atoms, $C_{1-10}$ alkyl, $C_{2-10}$ alkenyl, $C_{2-10}$ alkynyl, $C_{4-10}$ heterocycle and $C_{4-10}$ heteroaryl; and, $R^3$ is hydrogen atom, a halogen atom, a $C_1$-$C_4$ alkyl group, or a $C_1$-$C_3$ alkoxy group, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, and substituted or unsubstituted heteroaryl, H, —OH, —OR', —$NH_2$, —NHR', —$NR'_2$, —SH, —SR', —O—C(O)R', —C(O)R', $(CH_2)_bNH_2$, $C_{(m+1)}H_{(2m+1)}$, $C_{(m+1)}H_{(2m+1)}NH_2$, $C_{(m+1)}H_{(2m+1)}CONH_2$, $C_{(m+1)}H_{(2m+1)}$, $CR'NH_2$, $C_{(m+1)}H_{(2m+1)}$—$C_{4-20}$ aryl-$C_{(m+1)}H_{(2m+1)}$—$NH_2$, $C_mH_{2m+2}$, $C_{4-20}$ aryl, $C_{1-20}$ alkyl, $C_{1-20}$ alkylamino, $C_{2-20}$ alkenyl, $C_{2-20}$ alkynyl, $C_{4-20}$ heterocycle, $C_{4-20}$ heteroaryl, $C_{4-20}$ alkyl heterocycle, $C_{7-20}$ alkyl heteroaryl, $C_{1-20}$ alkyoxyl, where m is an integer from 0 to 10, and b is an integer from 0 to 10, wherein, the $C_{4-20}$ aryl, $C_{1-20}$ alkyl, $C_{2-20}$ alkenyl, $C_{2-20}$ alkynyl, $C_{4-20}$ heterocycle, $C_{4-20}$ heteroaryl, $C_{4-20}$ alkyl heterocycle, $C_{7-20}$ alkyl heteroaryl, $C_{1-20}$ alkyoxyl is unsubstituted or optionally substituted with a functional group comprising H, —OH, —OR', —$NH_2$, —NHR', —$NR'_2$, —SH, —SR', —O—C(O)R', —C(O)R', —$CF_3$, —$OCF_3$, the $C_{4-20}$ aryl, $C_{1-20}$ alkyl, $C_{2-20}$ alkenyl, $C_{2-20}$ alkynyl, $C_{4-20}$ heterocycle, $C_{4-20}$ heteroaryl, $C_{4-20}$ alkyl heterocycle, $C_{7-20}$ alkyl heteroaryl, $C_{1-20}$ alkyoxyl, and the $C_{1-6}$ alkyl is optionally interrupted by one or more O, S, or N atoms, or one or more groups comprising cycloalkyl, $C_{(m+1)}H_{(2m+1)}$, $C_{(m+1)}H_{(2m+1)}NH_2$, CH—C(O)—O—, —O—C(O)—, —C(O)—, —C(O)—NH—, —NH—C(O)—, —NH—C(O)—O— and —O—C(O)—NH—, R' is H, OH, halogen, —$CH_3$, $NO_2$, —$NH_2$, CN, —COOH, heteroaryl having 1 to 4 N, O and/or S atoms, $C_{4-20}$ aryl, $C_{1-10}$ alkyl, $C_{2-10}$ alkenyl, $C_{2-10}$ alkynyl, $C_{4-10}$ heterocycle or $C_{4-10}$ heteroaryl.

In certain embodiments, a method of method of preventing or treating a virus infection in vivo or in vitro, comprises administering to a subject in need thereof, or contacting a cell with a therapeutically effective amount of at least one compound set forth in Formula II, III, IV, or combinations thereof.

In another embodiment, a method of preventing or treating a virus infection in vivo or in vitro, comprising: administering to a subject in need thereof, or contacting a cell with a therapeutically effective amount of a composition comprising:

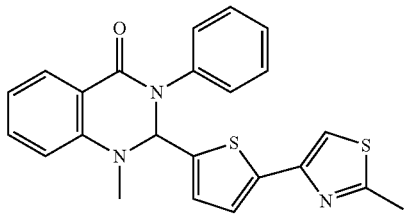 [SMILES: Cc1nc(-c2ccc(C3N(C)c4ccccc4C(=O)N3c3ccccc3)s2)cs1]

1-methyl-2-(5-(2-methylthiazol-4-yl)thiophen-2-yl)-3-phenyl-2,3-dihydroquinazolin-4(1H)-one),

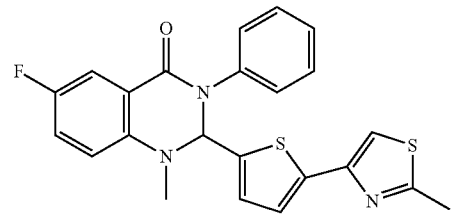 [SMILES: Cc1nc(-c2ccc(C3N(C)c4ccc(F)cc4C(=O)N3c3ccccc3)s2)cs1]

6-Fluoro-1-methyl-2-(5-(2-methylthiazol-4-yl)thiophen-2-yl)-3-phenyl-2,3-dihydroquinazolin-4(1H)-one), analogs, variants, derivatives or pharmaceutically acceptable salts thereof.

In embodiments, a virus infection comprises virus comprises herpesviruses, papilloma viruses, polyoma viruses or combinations thereof. In one embodiment the virus is a herpesvirus, for example, cytomegalovirus (CMV).

A method of modulating soluble NSF attachment protein receptor (SNARE) levels or activity in vitro or in vivo, comprising, contacting a cell in vitro or administering to a subject in need thereof, a therapeutically effective amount of a compound set forth in Formula I:

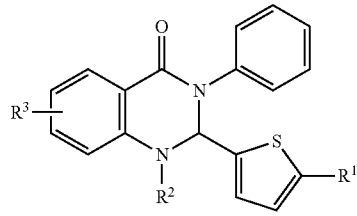

or a pharmaceutically acceptable salt thereof, wherein:

$R^1$ comprises H, O, 2-methylthiazol, an aromatic heterocyclic group; or an aromatic heterocyclic group substituted by: a $C_1$-$C_{10}$ alkyl group; a halogen atom; a phenyl group; a phenyl group substituted by one or more of: a $C_1$-$C_{10}$ alkoxy group, and a group —CN, —$NO_2$, —COX and —COOX, X being a $C_1$-$C_4$ alkyl radical; a group —SY, Y being a $C_1$-$C_4$ alkyl group or a phenyl group; —CN; a group —$CH_2$—$N_3$; a group —$CH_2$—$N_3$; an aromatic heterocyclic group selected from the group consisting of furan, thiophene, pyrrole, pyrroline, pyrrolidine, dioxolane, oxazole, thiazole, imidazole, imidazoline, imidazolidine, pyrazole, isoxazole, isothiazole, pyran, pyridine, piperidine, dioxane, morpholine, pyridazine, pyrimidine and pyrazine, each of which is optionally substituted by at least one $C_1$-$C_3$ alkyl radical and/or a group —$CH_2$—$N_3$ thereof; a phenyl group or a phenyl group substituted by a $C_1$-$C_3$ alkoxy group or $NMe_2$; and $R^2$ is H, OH, $CH_3$, halogen, $C_{1-10}$ alkyl, the $C_{1-10}$ alkyl is unsubstituted or optionally substituted with a functional group selected from the group consisting of H, —OH, —OR', —$NH_2$, —NHR', —NR'$_2$, —SH, —SR', —O—C(O)R', —C(O)R', —$CF_3$, —$OCF_3$, where R' is selected from radicals consisting of H, heteroaryl having 1 to 4 N, O, halogen and/or 5 atoms, $C_{1-10}$ alkyl, $C_{2-10}$ alkenyl, $C_{2-10}$ alkynyl, $C_{4-10}$ heterocycle and $C_{4-10}$ heteroaryl; and, $R^3$ is hydrogen atom, a halogen atom, a $C_1$-$C_4$ alkyl group, a $C_1$-$C_3$ alkoxy group, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, and substituted or unsubstituted heteroaryl, H, —OH, —OR', —$NH_2$, —NHR', —NR'$_2$, —SH, —SR', —O—C(O)R', —C(O)R', $(CH_2)_bNH_2$, $C_{(m+1)}H_{(2m+1)}$, $C_{(m+1)}H_{(2m+1)}NH_2$, $C_{(m+1)}H_{(2m+1)}CONH_2$, $C_{(m+1)}H_{(2m+1)}$, CR'$NH_2$, $C_{(m+1)}H_{(2m+1)}$—$C_{4-20}$ aryl-$C_{(m+1)}H_{(2m+1)}$—$NH_2$, $C_mH_{2m+2}$, $C_{4-20}$ aryl, $C_{1-20}$ alkyl, $C_{1-20}$ alkylamino, $C_{2-20}$ alkenyl, $C_{2-20}$ alkynyl, $C_{4-20}$ heterocycle, $C_{4-20}$ heteroaryl, $C_{4-20}$ alkyl heterocycle, $C_{7-20}$ alkyl heteroaryl, $C_{1-20}$ alkyoxyl, where m is an integer from 0 to 10, and b is an integer from 0 to 10, wherein, the $C_{4-20}$ aryl, $C_{1-20}$ alkyl, $C_{2-20}$ alkenyl, $C_{2-20}$ alkynyl, $C_{4-20}$ heterocycle, $C_{4-20}$ heteroaryl, $C_{4-20}$ alkyl heterocycle, $C_{7-20}$ alkyl heteroaryl, $C_{1-20}$ alkyoxyl is unsubstituted or optionally substituted with a functional group comprising H, —OH, —OR', —$NH_2$, —NHR', —NR'$_2$, —SH, —SR', —O—C(O)R', —C(O)R', —$CF_3$, or —$OCF_3$, the $C_{4-20}$ aryl, $C_{1-20}$ alkyl, $C_{2-20}$ alkenyl, $C_{2-20}$ alkynyl, $C_{4-20}$ heterocycle, $C_{4-20}$ heteroaryl, $C_{4-20}$ alkyl heterocycle, $C_{7-20}$ alkyl heteroaryl, $C_{1-20}$ alkyoxyl, and the $C_{1-6}$ alkyl is optionally interrupted by one or more O, S, or N atoms, or one or more groups comprising cycloalkyl, $C_{(m+1)}H_{(2m+1)}$, $C_{(m+1)}H_{(2m+1)}NH_2$, CH—C(O)—O—, —O—C(O)—, —C(O)—, —C(O)—NH—, —NH—C(O)—, —NH—C(O)—O— and —O—C(O)—NH—, R' is H, OH, halogen, —$CH_3$, $NO_2$, —$NH_2$, CN, —COOH, heteroaryl having 1 to 4 N, O and/or S atoms, $C_{4-20}$ aryl, $C_{1-10}$ alkyl, $C_{2-10}$ alkenyl, $C_{2-10}$ alkynyl, $C_{4-10}$ heterocycle or $C_{4-10}$ heteroaryl.

In other embodiments, a method of modulating soluble NSF attachment protein receptor (SNARE) levels or activity in vitro or in vivo, comprising, contacting a cell in vitro or administering to a subject in need thereof, a therapeutically effective amount of at least one compound set forth in Formula II, III, IV, or combinations thereof.

A method of inhibiting Syntaxin 5 (STX5) levels, localization, functions or activity thereof, in vitro or in vivo, comprising, contacting a cell in vitro or administering to a subject in need thereof, a therapeutically effective amount of a compound set forth in Formula I:

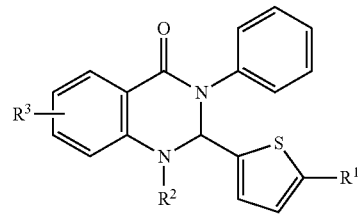

or a pharmaceutically acceptable salt thereof, wherein:

$R^1$ comprises H, O, 2-methylthiazol, an aromatic heterocyclic group; or an aromatic heterocyclic group substituted by: a $C_1$-$C_{10}$ alkyl group; a halogen atom; a phenyl group; a phenyl group substituted by one or more of: a $C_1$-$C_{10}$ alkoxy group, a group —CN, —$NO_2$, —COX and —COOX, X being a $C_1$-$C_4$ alkyl radical; a group —SY, Y being a $C_1$-$C_4$ alkyl group or a phenyl group; —CN; a group —$CH_2$—$N_3$; a group —$CH_2$—$N_3$; an aromatic heterocyclic group selected from the group consisting of furan, thiophene, pyrrole, pyrroline, pyrrolidine, dioxolane, oxazole, thiazole, imidazole, imidazoline, imidazolidine, pyrazole, isoxazole, isothiazole, pyran, pyridine, piperidine, dioxane, morpholine, pyridazine, pyrimidine and pyrazine, each of which is optionally substituted by at least one $C_1$-$C_3$ alkyl radical and/or a group —$CH_2$—$N_3$ thereof; a phenyl group or a phenyl group substituted by a $C_1$-$C_3$ alkoxy group or $NMe_2$; and $R^2$ is H, OH, $CH_3$, halogen, $C_{1-10}$ alkyl, the $C_{1-10}$ alkyl is unsubstituted or optionally substituted with a functional group selected from the group consisting of H, —OH, —OR', —$NH_2$, —NHR', —NR'$_2$, —SH, —SR', —O—C(O)R', —C(O)R', —$CF_3$, —$OCF_3$, where R' is selected from radicals consisting of H, heteroaryl having 1 to 4 N, O, halogen and/or S atoms, $C_{1-10}$ alkyl, $C_{2-10}$ alkenyl, $C_{2-10}$ alkynyl, $C_{4-10}$ heterocycle and $C_{4-10}$ heteroaryl; and, $R^3$ is hydrogen atom, a halogen atom, a $C_1$-$C_3$ alkoxy group, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, and substituted or unsubstituted heteroaryl, H, —OH, —OR', —$NH_2$, —NHR', —NR'$_2$, —SH, —SR', —O—C(O)R', —C(O)R', $(CH_2)_bNH_2$, $C_{(m+1)}H_{(2m+1)}$, $C_{(m+1)}H_{(2m+1)}NH_2$, $C_{(m+1)}H_{(2m+1)}CONH_2$, $C_{(m+1)}H_{(2m+1)}$, CR'$NH_2$, $C_{(m+1)}H_{(2m+1)}$—$C_{4-20}$ aryl-$C_{(m+1)}H_{(2m+1)}$—$NH_2$, $C_mH_{2m+2}$, $C_{4-20}$ aryl, $C_{1-20}$ alkyl, $C_{1-20}$ alkylamino, $C_{2-20}$ alkenyl, $C_{2-20}$ alkynyl, $C_{4-20}$ heterocycle, $C_{4-20}$ heteroaryl, $C_{4-20}$ alkyl heterocycle, $C_{7-20}$ alkyl heteroaryl, $C_{1-20}$ alkyoxyl, where m is an integer from 0 to 10, and b is an integer from 0 to 10, wherein, the $C_{4-20}$ aryl, $C_{1-20}$ alkyl, $C_{2-20}$ alkenyl, $C_{2-20}$ alkynyl, $C_{4-20}$ heterocycle, $C_{4-20}$ heteroaryl, $C_{4-20}$ alkyl heterocycle, $C_{7-20}$ alkyl heteroaryl, $C_{1-20}$ alkyoxyl is unsubstituted or optionally substituted with a functional group comprising H, —OH, —OR', —$NH_2$, —NHR', —NR'$_2$, —SH, —SR', —O—C(O)R', —C(O)R', —$CF_3$, —$OCF_3$, or an amino acid side chain or peptide fragment, the $C_{4-20}$ aryl, $C_{1-20}$ alkyl, $C_{2-20}$ alkenyl, $C_{2-20}$ alkynyl, $C_{4-20}$ heterocycle, $C_{4-20}$ heteroaryl, $C_{4-20}$ alkyl heterocycle, $C_{7-20}$ alkyl heteroaryl, $C_{1-20}$ alkyoxyl, and the $C_{1-6}$ alkyl is optionally interrupted by one or more O, S, or N atoms, or one or more groups comprising cycloalkyl, $C_{(m+1)}H_{(2m+1)}$, $C_{(m+1)}H_{(2m+1)}NH_2$, CH—C(O)—O—, —O—C(O)—, —C(O)—, —C(O)—NH—, —NH—C(O)—, —NH—C(O)—O— and —O—C(O)—NH—, R' is H, OH, halogen, —CH$_3$, NO$_2$, —NH$_2$, CN, —COOH, heteroaryl having 1 to 4 N, O and/or S atoms, C$_{4-20}$ aryl, C$_{1-10}$ alkyl, C$_{2-10}$ alkenyl, C$_{2-10}$ alkynyl, C$_{4-10}$ heterocycle or C$_{4-10}$ heteroaryl.

The activity, function, localization etc. of STX5 can be measured by any number of techniques known in the art. See, for example, the examples section which describe some of these techniques.

A method of inhibiting Syntaxin 5 (STX5) levels, localization, functions or activity thereof, in vitro or in vivo, comprising, contacting a cell in vitro or administering to a subject in need thereof, a therapeutically effective amount of at least one compound set forth in Formula II, III, IV, or combinations thereof.

In another preferred embodiment, a method of inhibiting cytoplasmic viral assembly compartment (cVAC) in vitro or in vivo, comprising, contacting a cell in vitro or administering to a subject in need thereof, a therapeutically effective amount of a compound set forth in Formula I:

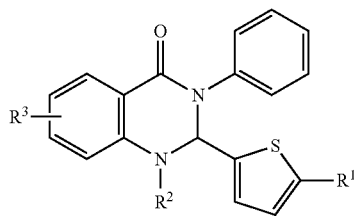

I or a pharmaceutically acceptable salt thereof,
wherein:

R$^1$ comprises H, O, 2-methylthiazol, an aromatic heterocyclic group; or an aromatic heterocyclic group substituted by: a C$_1$-C$_{10}$ alkyl group; a halogen atom; a phenyl group; a phenyl group substituted by one or more of: a C$_1$-C$_{10}$ alkoxy group, a group —CN, —NO$_2$, —COX and —COOX, X being a C$_1$-C$_4$ alkyl radical; a group —SY, Y being a C$_1$-C$_4$ alkyl group or a phenyl group; —CN; a group —CH$_2$—N$_3$; a group —CH$_2$—N$_3$; an aromatic heterocyclic group selected from the group consisting of furan, thiophene, pyrrole, pyrroline, pyrrolidine, dioxolane, oxazole, thiazole, imidazole, imidazoline, imidazolidine, pyrazole, isoxazole, isothiazole, pyran, pyridine, piperidine, dioxane, morpholine, pyridazine, pyrimidine and pyrazine, each of which is optionally substituted by at least one C$_1$-C$_3$ alkyl radical and/or a group —CH$_2$—N$_3$ thereof; a phenyl group or a phenyl group substituted by a C$_1$-C$_3$ alkoxy group or NMe$_2$; and, R$^2$ is H, OH, CH$_3$, halogen, C$_{1-10}$ alkyl, the C$_{1-10}$ alkyl is unsubstituted or optionally substituted with a functional group selected from the group consisting of H, —OH, —OR', —NH$_2$, —NHR', —NR'$_2$, —SH, —SR', —O—C(O)R', —C(O)R', —CF$_3$, —OCF$_3$, where R' is selected from radicals consisting of H, heteroaryl having 1 to 4 N, O, halogen and/or S atoms, C$_{1-10}$ alkyl, C$_{2-10}$ alkenyl, C$_{2-10}$ alkynyl, C$_{4-10}$ heterocycle and C$_{4-10}$ heteroaryl; and, R$^3$ is hydrogen atom, a halogen atom, a C$_1$-C$_3$ alkoxy group, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, and substituted or unsubstituted heteroaryl, H, —OH, —OR', —NH$_2$, —NHR', —NR'$_2$, —SH, —SR', —O—C(O)R', —C(O)R', (CH$_2$)$_b$NH$_2$, C$_{(m+1)}$H$_{(2m+1)}$, C$_{(m+1)}$H$_{(2m+1)}$NH$_2$, C$_{(m+1)}$H$_{(2m+1)}$CONH$_2$, C$_{(m+1)}$H$_{(2m+1)}$, CR'NH$_2$, C$_{(m+1)}$H$_{(2m+1)}$—C$_{4-20}$ aryl-C$_{(m+1)}$H$_{(2m+1)}$—NH$_2$, C$_m$H$_{2m+2}$, C$_{4-20}$ aryl, C$_{1-20}$ alkyl, C$_{1-20}$ alkylamino, C$_{2-20}$ alkenyl, C$_{2-20}$ alkynyl, C$_{4-20}$ heterocycle, C$_{4-20}$ heteroaryl, C$_{4-20}$ alkyl heterocycle, C$_{7-20}$ alkyl heteroaryl, C$_{1-20}$ alkyoxyl, where m is an integer from 0 to 10, and b is an integer from 0 to 10,
wherein, the C$_{4-20}$ aryl, C$_{1-20}$ alkyl, C$_{2-20}$ alkenyl, C$_{2-20}$ alkynyl, C$_{4-20}$ heterocycle, C$_{4-20}$ heteroaryl, C$_{4-20}$ alkyl heterocycle, C$_{7-20}$ alkyl heteroaryl, C$_{1-20}$ alkyoxyl is unsubstituted or optionally substituted with a functional group comprising H, —OH, —OR', —NH$_2$, —NHR', —NR'$_2$, —SH, —SR', —O—C(O)R', —C(O)R', —CF$_3$, —OCF$_3$, or an amino acid side chain or peptide fragment, the C$_{4-20}$ aryl, C$_{1-20}$ alkyl, C$_{2-20}$ alkenyl, C$_{2-20}$ alkynyl, C$_{4-20}$ heterocycle, C$_{4-20}$ heteroaryl, C$_{4-20}$ alkyl heterocycle, C$_{7-20}$ alkyl heteroaryl, C$_{1-20}$ alkyoxyl, and the C$_{1-6}$ alkyl is optionally interrupted by one or more O, S, or N atoms, or one or more groups comprising cycloalkyl, C$_{(m+1)}$H$_{(2m+1)}$, C$_{(m+1)}$H$_{(2m+1)}$NH$_2$, CH—C(O)—O—, —O—C(O)—, —C(O)—, —C(O)—NH—, —NH—C(O)—, —NH—C(O)—O— and —O—C(O)—NH—, R' is H, OH, halogen, —CH$_3$, NO$_2$, —NH$_2$, CN, —COOH, heteroaryl having 1 to 4 N, O and/or S atoms, C$_{4-20}$ aryl, C$_{1-10}$ alkyl, C$_{2-10}$ alkenyl, C$_{2-10}$ alkynyl, C$_{4-10}$ heterocycle or C$_{4-10}$ heteroaryl.

In another preferred embodiment, a method of inhibiting cytoplasmic viral assembly compartment (cVAC) in vitro or in vivo, comprising, contacting a cell in vitro or administering to a subject in need thereof, a therapeutically effective amount of at least one compound set forth in Formula II, III, IV, or combinations thereof.

The inhibition of assembly of cVAC can be measured by any number of techniques known in the art. See, for example, the examples section which describe some of these techniques.

Pharmaceutical Compositions

The invention also includes pharmaceutical compositions comprising at least one compound having general formulae I, II, III, IV, or combinations thereof. In some embodiments, the compositions are suitable for internal use and include an effective amount of a pharmacologically active conjugate of the invention, alone or in combination, with one or more pharmaceutically acceptable carriers.

The patient having pathology, e.g. the patient treated by the methods of this invention can be a mammal, or more particularly, a human. In practice, the agents are administered in amounts which will be sufficient to exert their desired biological activity.

The pharmaceutical compositions of the invention may contain, for example, more than one type of compounds of formulae I, II, III, IV. In some examples, a pharmaceutical composition of the invention, containing one or more compounds of the invention, is administered in combination with another useful composition such as an anti-inflammatory agent, an immunostimulator, a chemotherapeutic agent, an antiviral agent, or the like. Furthermore, the compositions of the invention may be administered in combination with a cytotoxic, cytostatic, or chemotherapeutic agent such as an alkylating agent, anti-metabolite, mitotic inhibitor or cytotoxic antibiotic. In general, the currently available dosage forms of the known therapeutic agents for use in such combinations will be suitable.

Combination therapy (or "co-therapy") includes the administration of the compositions and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected).

Combination therapy may, but generally is not, intended to encompass the administration of two or more of these therapeutic agents as part of separate monotherapy regimens that incidentally and arbitrarily result in the combinations of the present invention. Combination therapy is intended to embrace administration of compounds of formula I in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents.

Sequential or substantially simultaneous administration of each therapeutic agent can be effected by any appropriate route including, but not limited to, topical routes, oral routes, intravenous routes, intramuscular routes, and direct absorption through mucous membrane tissues. The therapeutic agents can be administered by the same route or by different routes. For example, a first therapeutic agent of the combination selected may be administered by injection while the other therapeutic agents of the combination may be administered topically.

Alternatively, for example, all therapeutic agents may be administered topically or all therapeutic agents may be administered by injection. The sequence in which the therapeutic agents are administered is not narrowly critical unless noted otherwise. Combination therapy also can embrace the administration of the therapeutic agents as described above in further combination with other biologically active ingredients. Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

Therapeutic or pharmacological compositions of the present invention will generally comprise an effective amount of the active component(s), dissolved or dispersed in a pharmaceutically acceptable medium. Pharmaceutically acceptable media or carriers include any and all solvents, dispersion media, coatings, antibacterial and antifungal agents, isotonic and absorption delaying agents and the like. The use of such media and agents for pharmaceutical active substances is well known in the art. Supplementary active ingredients can also be incorporated into the therapeutic compositions of the present invention.

For any agent used in the methods of the invention, the therapeutically effective amount or dose can be estimated initially from activity assays in cell cultures and/or animals. For example, a dose can be formulated in animal models to achieve a circulating concentration range that includes the $IC_{50}$ as determined by activity assays (e.g., the concentration of the test compound, which achieves a half-maximal inhibition of the proliferation activity). Such information can be used to more accurately determine useful doses in humans.

Toxicity and therapeutic efficacy of the compounds described herein can be determined by standard pharmaceutical procedures in experimental animals, e.g., by determining the $IC_{50}$ and the $LD_{50}$ (lethal dose causing death in 50% of the tested animals) for a subject compound. The data obtained from these activity assays and animal studies can be used in formulating a range of dosage for use in human.

The dosage may vary depending upon the dosage form employed and the route of administration utilized. The exact formulation, route of administration and dosage can be chosen by the individual physician in view of the patient's condition. Dosage amount and interval may be adjusted individually to provide plasma levels of the active moiety which are sufficient to maintain therapeutic effects, termed the minimal effective concentration (MEC). The MEC will vary for each preparation, but can be estimated from in vitro and/or in vivo data, e.g., the concentration necessary to achieve 50-90% inhibition of a proliferation of certain cells may be ascertained using the assays described herein. Dosages necessary to achieve the MEC will depend on individual characteristics and route of administration. HPLC assays or bioassays can be used to determine plasma concentrations. Dosage intervals can also be determined using the MEC value. Preparations should be administered using a regimen, which maintains plasma levels above the MEC for 10-90% of the time, preferably between 30-90% and most preferably 50-90%. Depending on the severity and responsiveness of the condition to be treated, dosing can also be a single administration of a slow release composition described hereinabove, with course of treatment lasting from several days to several weeks or until cure is effected or diminution of the disease state is achieved. The amount of a composition to be administered will, of course, be dependent on the subject being treated, the severity of the affliction, the manner of administration, the judgment of the prescribing physician, etc.

The preparation of pharmaceutical or pharmacological compositions will be known to those of skill in the art in light of the present disclosure. Typically, such compositions may be prepared as injectables, either as liquid solutions or suspensions; solid forms suitable for solution in, or suspension in, liquid prior to injection; as tablets or other solids for oral administration; as time release capsules; or in any other form currently used, including eye drops, creams, lotions, salves, inhalants and the like. The use of sterile formulations, such as saline-based washes, by surgeons, physicians or health care workers to treat a particular area in the operating field may also be particularly useful. Compositions may also be delivered via microdevice, microparticle or other known methods.

Upon formulation, therapeutics will be administered in a manner compatible with the dosage formulation, and in such amount as is pharmacologically effective. The formulations are easily administered in a variety of dosage forms, such as the type of injectable solutions described above, but drug release capsules and the like can also be employed.

In this context, the quantity of active ingredient and volume of composition to be administered depends on the host animal to be treated. Precise amounts of active compound required for administration depend on the judgment of the practitioner and are peculiar to each individual.

The pharmaceutical compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating, or coating methods, and typically contain about 0.1% to 75%, preferably about 1% to 50%, of the active ingredient.

Liquid, particularly injectable compositions can, for example, be prepared by dissolving, dispersing, etc. The active compound is dissolved in or mixed with a pharmaceutically pure solvent such as, for example, water, saline, aqueous dextrose, glycerol, ethanol, and the like, to thereby form the injectable solution or suspension. Additionally, solid forms suitable for dissolving in liquid prior to injection can be formulated.

The compositions of the present invention can be administered in intravenous (both bolus and infusion), intraperitoneal, subcutaneous or intramuscular form, all using forms well known to those of ordinary skill in the pharmaceutical arts. Injectables can be prepared in conventional forms, either as liquid solutions or suspensions.

Parenteral injectable administration is generally used for subcutaneous, intramuscular or intravenous injections and infusions. Additionally, one approach for parenteral administration employs the implantation of a slow-release or sustained-released systems, which assures that a constant level of dosage is maintained. Furthermore, preferred compositions for the present invention can be administered in intranasal form via topical use of suitable intranasal vehicles, inhalants, or via transdermal routes, using those forms of transdermal skin patches well known to those of ordinary skill in that art. To be administered in the form of a transdermal delivery system, the dosage administration will, of course, be continuous rather than intermittent throughout the dosage regimen. Other preferred topical preparations include creams, suppositories, ointments, lotions, aerosol sprays and gels, wherein the concentration of active ingredient would typically range from 0.01% to 15%, w/w or w/v.

The active compound defined above, may be also formulated as suppositories, using for example, polyalkylene glycols, for example, propylene glycol, as the carrier. In some embodiments, suppositories are advantageously prepared from fatty emulsions or suspensions.

The compounds of the present invention can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564. For example, the molecules described herein can be provided as a complex with a lipophilic compound or non-immunogenic, high molecular weight compound constructed using methods known in the art. An example of nucleic-acid associated complexes is provided in U.S. Pat. No. 6,011,020.

The compounds of the present invention may also be coupled with soluble polymers as targetable drug carriers. Such polymers can include polyvinylpyrrolidone, pyran copolymer, polyhydroxypropyl-methacrylamide-phenol, polyhydroxyethylaspanamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

If desired, the pharmaceutical composition to be administered may also contain minor amounts of non-toxic auxiliary substances such as wetting or emulsifying agents, pH buffering agents, and other substances such as for example, sodium acetate, and triethanolamine oleate. The dosage regimen utilizing the molecules is selected in accordance with a variety of factors including type, species, age, weight, sex and medical condition of the patient; the severity of the condition to be treated; the route of administration; the renal and hepatic function of the patient; and the particular molecule or salt thereof employed. An ordinarily skilled physician or veterinarian can readily determine and prescribe the effective amount of the drug required to prevent, counter or arrest the progress of the condition. Compounds of the present invention may be administered in a single daily dose, or the total daily dosage may be administered in divided doses of two, three or four times daily.

All documents mentioned herein are incorporated herein by reference. All publications and patent documents cited in this application are incorporated by reference for all purposes to the same extent as if each individual publication or patent document were so individually denoted. By their citation of various references in this document, Applicants do not admit any particular reference is "prior art" to their invention.

The invention has been described in detail with reference to preferred embodiments thereof. However, it will be appreciated that those skilled in the art, upon consideration of this disclosure, may make modifications and improvements within the spirit and scope of the invention. The following non-limiting examples are illustrative of the invention.

EXAMPLES

Example 1: Potent Inhibition of HCMV by Displacing a Cellular SNARE

The role for a subset of key SNARE proteins involved in transport to, from, and within the Golgi in forming the HCMV cVAC was investigated. It was found that STX5 is upregulated during infection concomitant with cVAC formation, and an essential role for STX5 in the production of infectious virions was identified. The reduced production of virus correlated with a morphologically altered cVAC devoid of viral proteins. Furthermore, it was determined that a compound that displaces STX5 from its cVAC localization impaired HCMV replication. This inhibitor exhibited an $IC_{50}$ in the low nanomolar range and showed zero toxicity on cells after extended treatment. These findings identify STX5 as a critical SNARE for cVAC formation and identify a potential novel cellular target for the therapeutic intervention of HCMV infections. Not only do these results provide another step towards understanding the mechanism of cVAC formation during HCMV infection, but these findings also reaffirm the idea that identifying key proteins essential for virus replication, both viral and cellular, can provide novel targets for therapeutic intervention.

Materials and Methods

Tissue Culture.

Normal human dermal fibroblasts, HDFs (Cell Applications Inc. 106-05N), and normal human lung fibroblasts, MRC-5 cells (ATCC CCL-171) were maintained in Dulbecco's modified Eagle's medium (DMEM) (Lonza). Human retinal pigmented epithelial cells (ARPE-19), maintained in DMEM/Ham's F12 (1:1 mix) (Lonza), human embryonic lung fibroblasts (HEL) and mouse embryonic fibroblasts (NIH 3T3), maintained in DMEM (Lonza) were obtained (Spector D J, Yetming K. *Virology*. 2010; 407(2):171-7; Spector D J. *Virology*. 2015, 476:345-54). All media was supplemented with 10% fetal bovine serum, 100 U/ml penicillin and 100 g/ml streptomycin, and 2 mM GlutaMAX (Gibco). Cells were maintained at 37° C. with 5% $CO_2$. Trypan blue was used for studies assaying cell viability.

Cloning and BAC Mutagenesis.

pTRE3G-Bi and pEF1a-Tet3G (Clontech Cat. 631340) were used to create inducible miRNA expression vectors. A DNA oligonucleotide encoding the full-length miRNA construct with BamHI and NotI overhangs was inserted into pTRE3G-Bi MCS1 using BamHI and NotI enzymes 5'-GATCCTGGAGGCTTGCTGAAGGCTGTATGCTCA-GGACCCATGGCCTGTTACTA GCACTCACATG-GAACAAATGGCCCA (SEQ ID NO: 1). The miRNA construct was created with an internal NcoI sequence to insert specific miRNA sequences into the full-length construct. miRNA targeting STX5 and luciferase was designed using BLOCK-iT RNAi Designer (ThermoFisher Scientific) and complimentary DNA oligonucleotides encoding the gene-specific sequences were annealed and subsequently inserted using BamHI and NcoI enzymes.

miSTX5 sense:
(SEQ ID NO: 2)
5'-GATCCTGGAGGCTTGCTGAAGGCTGTATGCTGAGACACCATGCAGAA
CATTGAGTTTTGGCCACTGACTGACTCAATGTTGCATGGTGTCTCAGGAC
C;

antisense:
(SEQ ID NO: 3)
5'-CATGGGTCCTGAGACACCATGCAACATTGAGTCAGTCAGTGGCCAAA
ACTCAATGTTCTGCATGGTGTCTCAGCATACAGCCTTCAGCAAGCCTCCA
G.

miLUC sense:
(SEQ ID NO: 4)
5'GATCCTGGAGGCTTGCTGAAGGCTGTATGCTGAAATCGCTGATTTGTG
TAGTCGTTTTGGCCACTGACTGACGACTACACATCAGCGATTTCAGGAC
C;

antisense:
(SEQ ID NO: 5)
5'CATGGGTCCTGAAATCGCTGATGTGTAGTCGTCAGTCAGTGGCCAAAA
CGACTACACAAATCAGCGATTTCAGCATACAGCCTTCAGCAAGCCTCCA
G.

To insert EGFP into pTRE3G-Bi MCS2, EGFP was amplified using forward primer: 5' GCATGAATTCATGGT-GAGCAAGGGCGAG 3' (SEQ ID NO: 6) and reverse primer: 5 GCATTCTAGATTACTTGTACAGCTCGTC 3' (SEQ ID NO: 7) and inserted using EcoRI and XbaI enzymes.

The pp28-mCherry virus was made by PCR amplification of galK with the following primers:

forward
(SEQ ID NO: 8)
5'AACGTCCACCCACCCCCGGGACAAAAAAGCCCGCCGCCTCCTTGCCCT
TTCCTGTTGACAATTAATCATCGGCA
and reverse
(SEQ ID NO: 9)
5'TGTCCCATTCCCGACTCGCGAATCGTACGCGAGACCTGAAAGTTTATG
AGTCAGCACTGTCCTGCTCCTT.

mCherry was amplified and inserted into the galK BAC using the following primers:

forward
(SEQ ID NO: 10)
5'AACGTCCACCCACCCCCGGGACAAAAAAGCCCGCCGCCTCCTTGCCCT
TTCGGGATCCCGCCACCATGGTG
and, reverse
(SEQ ID NO: 11)
5'TGTCCCATTCCCGACTCGCGAATCGTACGCGAGACCTGAAAGTTTATG
AGTTACTTGTACAGCTCGTCCA.

The pp150-GFP virus was made by PCR amplification of galK with the following primers:

forward
(SEQ ID NO: 12)
5'
GCCGTGCAGAACATCCTCCAAAAGATCGAGAAGATTAAGAACACGGAGGA
ACCTGTTGACAATTAATCATCGGCA
and, reverse
(SEQ ID NO: 13)
5'
ACACGTCACTATCCGATGGTTTCATTAAAAAGTACGTCTGCGTGTGTGTT
TCTTAATCAGCACTGTCCTGCTCCTT.

EGFP was amplified and inserted into the galK BAC using the primers:

forward
(SEQ ID NO: 14)
5'GCCGTGCAGAACATCCTCCAAAAGATCGAGAAGATTAAGAACACGGAG
GAACCACCGGTCGCCACCATGGTGAGC
and, reverse:
(SEQ ID NO: 15)
5'
ACACGTCACTATCCGATGGTTTCATTAAAAAGTACGTCTGCGTGTGTGTT
TCTTAATTACTTGTACAGCTCGTCCATGCC.

To make tet-inducible miRNA expressing viruses, multiple recombineering steps were performed. First, the EF1a-Tet3G construct was inserted into the TRS1 area of the BAC genome. Since pEF1a-Tet3G and pTRE3G-Bi both contain SV40 termination sequences, the SV40 terminator on EF1a-Tet3G was replaced with the BGH termination sequence through a PCR sewing step to avoid additional sites for potential recombination to occur. To insert EF1a-Tet3G-BGH, the GalK sequence was inserted upstream of TRS1 using the following primers:

forward
(SEQ ID NO: 16)
5'
CGTTTGCCGTTGGGCGTACGCTACGTTTGTATTTCTGGCTATAATATGTG
CCTGTTGACAATTAATCATCGGCA
and, reverse
(SEQ ID NO: 17)
5'
ATACACCCTACAGTCACACCCTTCCCAATAGGAACATCGACACATGACCG
TCAGCACTGTCCTGCTCCTT.

EF1a-Tet3G-BGH was amplified and inserted into the galK BAC using the following primers:

forward (SEQ ID NO: 18)

5'
CGTTTGCCGTTGGGCGTACGCTACGTTTGTATTTCTGGCTATAATATGTG
GAGTAATTCATACAAAAG
and, reverse (SEQ ID NO: 19)

5'
ATACACCCTACAGTCACACCCTTCCCAATAGGAACATCGACACATGACCG
CCATAGAGCCCACCGCATCC.

To insert constructs under control of the bidirectional promoter, the GalK sequence was first inserted downstream of US34a area using the following primers:

forward (SEQ ID NO: 20)

5'
AGGGTGGCGAGGTGTGAGGATGAAACATATGCAGATACGCAGTGTTGTTA
CCTGTTGACAATTAATCATCGGCA
and, reverse (SEQ ID NO: 21)

5'
GACTTTCATACTGAAGTACCGTTGTACGCATTACACGGGTTTCGTTCGGA
TCAGCACTGTCCTGCTCCTT.

The GFP-tetpromoter-miRNA sequence was then inserted by amplifying the miRNA-containing plasmid with the following primers:

forward (SEQ ID NO: 22)

5'
AGGGTGGCGAGGTGTGAGGATGAAACATATGCAGATACGCAGTGTTGTTA
AAGTGCCACCTGACGTCG
and, reverse (SEQ ID NO: 23)

5'
GACTTTCATACTGAAGTACCGTTGTACGCATTACACGGGTTTCGTTCGGA
GTGAGCGAGGAAGCTCGG3'.

Recombinant viruses were made by BAC mutagenesis using *E. coli* strain SW105 and galK selection as described previously (Warming S, et al. *Nucleic Acids Res.* 2005; 33(4):e36). Briefly, overnight cultures grown in YENB with 12.5 μg/ml chloramphenicol at 32.5° C. were expanded and grown to mid-log phase. Following a heat shock at 42° C., 50 μl of cells were then electroporated, 2.5 kV/25 μFD, 200 Ohms (Bio-Rad Gene-Pulser) purified PCR DNA products. Following recovery period, bacteria was washed in M9 salts and plated on selection media. For galK selection, cells were plated on M63 minimal plates containing galactose and replated on MacConkey agar for confirmation of presence of GalK. For gene of interest selection, cells were grown on plates containing 2-deoxygalactose. BAC DNA was isolated and insertion sites were amplified and verified by Sanger sequencing (Eurofins or GENEWIZ).

Virus Preparation, Titration, Infections and Growth Curves.

Titered MCMV (Smith, ATCC VR-1399) and HCMV TB40-mCherry, Toledo, Towne, and Merlin were provided by David Spector (Spector D J, Yetming K. *Virology.* 2010; 407(2):171-7; Spector D J. *Virology.* 2015; 476: 345-54). AD169 and derivatives generated above were generated from BAC stocks. To generate virus stocks, BAC DNA was electroporated into MRC5 cells according to previously published protocols (Spector D J, Yetming K. *Virology.* 2010; 407(2):171-7). Virus-producing cells were saved at P0 in liquid nitrogen and used to infect cells in roller bottles to produce larger stocks of virus. Virus stocks were concentrated by high-speed centrifugation on a 20% sorbitol cushion at 20,000 rpm, for 1 hr at 20° C. in a Beckman SW32 rotor.

Infections were done at an MOI of 0.05 for multi-step growth curves and MOI 3 for single-step growth curves. Infections were done on NHDFs unless otherwise noted. Virus was incubated with cells for 2 hours before addition of fresh media. For growth curve analyses, virus was harvested at the indicated time-points for each experiment by scraping the cells into the medium, sonicating 10 times with 1 second pulses, vortexing for 15 seconds, and centrifuging at 13,000 rpm for 10 min. Supernatants were collected, aliquoted and flash-frozen in liquid nitrogen before storage at −80° C.

For MCMV growth curve analysis, samples were titrated on NIH 3T3 cells and titers were calculated using the 50% tissue culture infective dose method. Both HCMV virus stocks and samples for growth curves were titrated by serial dilutions on MRC5 cells and quantified by the immunological detection of immediate-early proteins as previously described (Britt W J. Human cytomegalovirus: propagation, quantification, and storage. *Curr Protoc Microbiol.* 2010; Chapter 14: Unit 14E.3). The numbers of stained nuclei were acquired on a Nikon Eclipse Ti Inverted microscope and fluorescent nuclei were quantified using the NIS Elements Software. Images of viral foci from infection of ARPE19 cells were also acquired on Eclipse Ti Inverted microscope. The number and size of foci were quantified using NIS Elements software.

Reagents and Antibodies.

Doxycycline (Enzo Life Sciences) was added to the media 2 hours post-infection at 10 μg/ml and the media was supplemented every 3 days.

Antibodies against GS15 (19), Bet1 (17), and Ykt6p (E-2) were purchased from Santa Cruz. Cytomegalovirus gB late antigen antibody (C58G) and beta-actin antibody (BA3R) were purchased from ThermoFisher Scientific. Anti-pp28 (5C3) was purchased from Abcam Inc. Antibodies against EEA1 (F.43.1), GM130, p230, syntaxin 8, GS28, and GS27 (25) were purchased from BD Transduction Laboratories. Antibodies against syntaxin 7 (Bethyl laboratories), syntaxin 18 (A01) (Abnova), syntaxin 16 (Proteintech) and Sec22b (Abgent), a tubulin (Sigma Aldrich) were purchased from the indicated suppliers. A rabbit polyclonal antibody that detects exons 2 & 3 of the HCMV major immediate early proteins was previously described (Harel N Y, Alwine J C. *J Virol.* 1998; 72(7):5481-92). Horseradish peroxidase-conjugated secondary antibodies for western blotting detection were purchased from Santa Cruz (goat anti rabbit) and Jackson laboratories (goat anti mouse). FITC and Rhodamine-conjugated secondary antibodies for immunofluorescent staining were purchased from Santa Cruz Biotechnology, Inc.

Retro-94 Synthesis and Use.

1-Methyl-2-(5-(2-methylthiazol-4-yl)thiophen-2-yl)-3phenyl-2,3-dihydroquinazolin-4(1H)-one (Retro94) was synthesized as reported in the literature with minor modification (Noel R, et al. *J Med Chem.* 2013; 56(8):3404-13). Briefly, to a solution of 2-aminobenzanilide (1 mmol) in methanol (3 ml) was added 5-(2-methyl-3-thiazol-4-yl)-2-thiophencarboxaldehyde (1 mmol), and the reaction mixture was stirred at room temperature for overnight. The precipitated yellow colored imino compound was filtered and washed with small quantity of methanol to give 62% yield.

The imino compound (0.75 mmol) was dissolved in anhydrous THF (10 ml) and reacted with NaH (60% in oil washed with hexane, 2.5 mmol) at 0° C. for 4-6 h and iodomethane (3 mmol) was added dropwise at 0° C. After the addition, the reaction mixture was allowed to warm to room temperature and stirred for overnight. The reaction mixture was carefully quenched with saturated $NaHCO_3$. The aqueous layer was extracted with $CH_2Cl_2$ (4×25 ml), washed with 1N HCl (2×10 mL), dried over $MgSO_4$, filtered, and evaporated to dryness. The crude product was purified over silica gel column by eluting with EtOAC: hexane (2:8) to give Retro94 in overall 71% yield. $^1$H NMR (500 mHz, $CDCl_3$) δ (ppm): 8.12 (dd, 1H, j=6.5 Hz, j'=1.5 Hz), 7.46-7.40 (m, 1H), 7.40-7.24 (m, 5H), 7.12 (s, 1H), 6.99 (dt, 1H, j=8.5 Hz, j'=1 Hz), 6.84 (d, 1H, j=3.0 Hz), 6.69 (d, 1H, j=7.0 Hz), 5.99 (s, 1H), 3.02 (s, 3H, $NCH_3$), 2.74 (s, 3H, $CH_3$); MS (ESI) $[M=H]^+$: 417.8.

$^1$H NMR spectra were recorded on a 500 MHz Bruker spectrometer (Billerica, Mass.) using tetramethylsilane (TMS) as the internal reference. The following abbreviations were used to designate chemical shift multiplicities: s=singlet, d=doublet, dd=double doublet, t=triplet, dt=doublet of triplet, m=multiplet. Mass Spec analysis was performed on 4000 Q trap hybrid triple quadrupole/linear ion trap instrument (Applied Biosystems/MDS Sciex) at the proteomic facility at Penn State Hershey Cancer Institute, Hershey, Pa. Thin-layer chromatography (TLC) was on aluminum-supported, precoated silica gel plates (EM Industries, Gibbstown, N.J.). 5-(2-methyl-3-thiazol-4-yl)-2-thiophencarboxaldehyde was purchased from MAYBRIDGE-Thermo Fisher (Cornwall, UK). All other starting materials were obtained from Aldrich Chemical Co. (Milwaukee, Wis.) and used without further purification. Retro94 was added to cells at 2 hpi at a concentration of 10 μM, unless otherwise indicated.

Western Blotting.

Total cell lysates were prepared from uninfected or HCMV-infected cells (MOI=3) at the indicated time points by harvesting lystates in radioimmunoprecipitation assay buffer (1% NP-40, 1% sodium deoxycholate, 0.1% sodium dodecyl sulfate [SDS], 0.15 M NaCl, 10 mM sodium phosphate [pH 7.2], 2 mM EDTA, 50 mM NaF, 1 mM phenylmethylsulfonyl fluoride, 1 mM aprotinin, 0.2 mM $Na_3VO_4$, 1 μg/ml leupeptin). After centrifugation, the supernatant was collected and stored at −80° C. The protein was quantified by a Bradford assay (Bio-Rad) and samples were analyzed by SDS-PAGE gel electrophoresis and immunoblotting on nitrocellulose or PVDF membrane blocked with 5% milk or 5% BSA in tris-buffered saline (0.1% tween). Antibody dilutions were in accordance with manufacturer's instructions.

Quantitative PCR.

Total RNA was harvested from uninfected or HCMV-infected cells (MOI=3) at the indicated time points using the SurePrep TrueTotal RNA Purification Kit (Fisher Bioreagents). 1 μg RNA was used to synthesize cDNA using the Superscript First-Strand cDNA kit (Invitrogen). qPCR was performed using the 2×SYBR Green Master Mix (Roche) on a StepOne Plus Real-Time PCR System (Applied Biosystems). The following primers were used: STX5 forward 5'-ATGTCCTGCCGGGATCGGAC (SEQ ID NO: 24) and reverse 5'-CATCAAAGAGGGACTTGCGCTTTGCC (SEQ ID NO: 25), STX7 forward 5'-TTCAG-CAAGCAAATCAGCAG (SEQ ID NO: 26) and reverse 5'-GAATGATGATGCACAGGGTTT (SEQ ID NO: 27), STX16 forward 5'-CAGCTGTTAGCCGAGCAAGT (SEQ ID NO: 28) and reverse 5'-CATCAGCAAGCTCGTCCAG (SEQ ID NO: 29), STX18 forward 5'-TTCTTCTG-GAACACAGGAAAGAT (SEQ ID NO: 30) and reverse 5'-TCTGGGCATCCTGGTCTATC (SEQ ID NO: 31).

Immunofluorescence Microscopy and Imaging.

Coverslips or chamber slides containing either uninfected or HCMV-infected cells were washed in phosphate-buffered saline (PBS) and fixed in 2% paraformaldehyde for 15 min at room temperature. Cells were blocked in PBS containing 10% human serum, 0.5% Tween-20, and 5% glycine. 0.1% Triton-X 100 was added for permeabilization. Primary and secondary antibodies as specified in the antibody section were diluted in blocking buffer. Nuclei were stained with DAPI prior to mounting with ProLong Diamond Antifade Mountant (ThermoScientific). For live-cell experiments using the pp28-mCherry virus, cells were grown on glass bottom microwell dishes (MatTek Corporation) and nuclei were stained with NucBlue Live Cell Stain ReadyProbes reagent (ThermoScientific). All images were acquired using a C2+ Confocal Microscope System (Nikon). Images were processed using NIS elements software. Images shown are volume renderings of Z-stacks.

Electron Microscopy.

Cells were seeded on 60 mm Permanox tissue culture dishes (Nalge Nunc International). Infections were done at an MOI of 3 for 96 hours. Cells were first washed with PBS 3× followed by fixation for 1 hour at 4° C. in fixation buffer (0.5% [vol/vol] glutaraldehyde, 0.04% [wt/vol] paraformaldehyde, 0.1 M sodium cacodylate). Cells were then processed for EM by the Microscopy Imaging Facility (Pennsylvania State University College of Medicine). Briefly, the fixed samples were washed three times with 0.1 M sodium cacodylate, followed by postfixation in 1% osmium −1.5% potassium ferrocyanide overnight at 4° C. Samples were then washed 3 times in 0.1 M sodium cacodylate, dehydrated with ethanol, and embedded in Epon 812 for staining and sectioning. Images were acquired using a JEOL JEM-1400 Digital Capture transmission electron microscope.

Novel Synthesis for Retro94 derivatives.

All reactions were carried out under an inert atmosphere with dry solvents under anhydrous conditions, unless otherwise stated. The starting materials obtained from commercial sources were used without further purification. All reactions were monitored by TLC on Silica Gel 60 F254 (Merck) using UV light detection. Silica gel (60-120 mesh size) for column chromatography was procured from Sili-Cycle (Quebec City, Canada). Microwave experiments were performed on CEM Discover focused microwave (250 MHz, 300 W). $^1$H (500 MHz) NMR spectra were recorded on a Bruker Avance-500 spectrometer. Chemical shifts were recorded in δ (ppm) relative to the TMS signal, coupling constants (J) are given in Hz and multiplicities of the signals are reported as follows: s, singlet; d, doublet; dd, double doublet; t, triplet; m, multiplet; br, broad singlet.

Scheme 1: Synthesis of DABL-N and DABL-NM

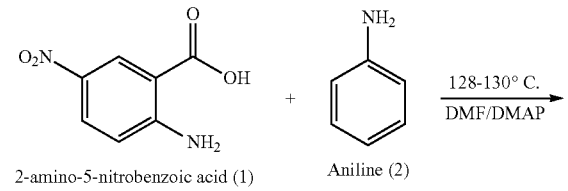

2-amino-5-nitrobenzoic acid (1)   Aniline (2)

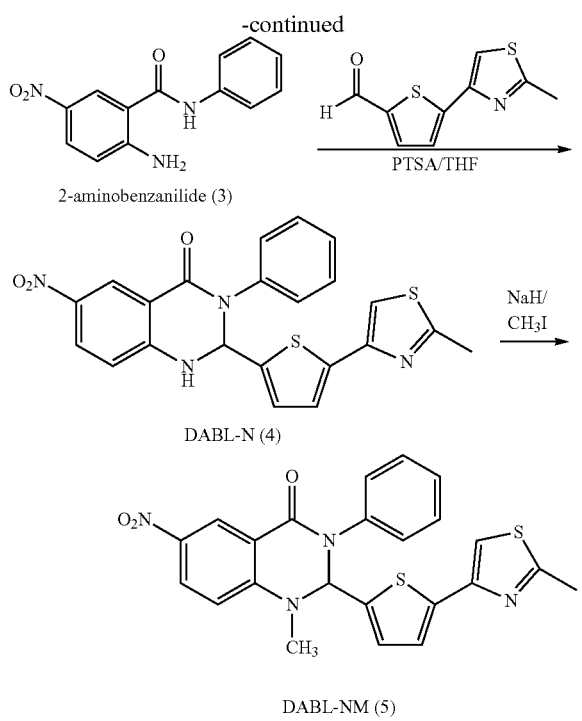

DABL-N (4)

DABL-NM (5)

Synthesis of DABL-N (4) and DABL-NM (5)

5-Nitro-N-phenylbenzamide (3, Scheme 1): 5-Nitro isatoic anhydride (208 mg, 1 mmol) was mixed with aniline (100 mg, 1.1 mmol), DMSO (0.5 mL), and catalytic amount of DMAP (3 mg) in a sealed tube and the resulting mixture was heated at 130° C. overnight. The resulting reaction mixture was cooled to room temperature and ethyl acetate was added to the mixture, sonicated to dissolve the entire residue. Flash chromatography [eluted with hexane:Ethyl acetate (80/20)] afforded 5-Nitro-N-phenylbenzamide (3, Scheme 1) (160 mg, 62%) as pale yellow powder. $^1$H-NMR (500 MHz, D4-MeOH) δ (ppm)=8.65 (d, 1H, J=2.5 Hz), 8.12 and 8.10 (dd, 1H, J=2.5 Hz, J=9.0 Hz), 7.69-7.66 (m, 2H), 7.40-7.36 (m, 2H), 7.19-7.15 (m, 1H), 6.84 (d, 1H, J=9.5 Hz).

6-Nitro-2-(5-(2-methylthiazol-4-yl)thiophen-2-yl)-3-phenyl-2,3-dihydroquinazolin-4(1H)-one (DABL-N, 4, Scheme 1): 5-Nitro-N-phenylbenzamide (120 mg, 0.47 mmol) and 5-(2-methylthiazol-4-yl)thiophene-2-carbaldehyde (107 mg, 0.51 mmol) were dissolved in THF (8 mL) and a catalytic amount of PTSA (9 mg, 0.05 mmol) was added. The reaction mixture was refluxed overnight. After evaporation to dryness the crude mixture was purified by flash chromatography on silica gel using hexane/ethyl acetate (80/20) to yield 6-Nitro-2-(5-(2-methylthiazol-4-yl)thiophen-2-yl)-3-phenyl-2,3-dihydroquinazolin-4(1H)-one (4, Scheme 1) as yellow powder (116 mg, 56%). $^1$H-NMR (500 MHz, CDCl$_3$) δ (ppm)=8.88 (d, 1H, J=3.0 Hz), 8.16 and 8.14 (dd, 1H, J=2.5 Hz and J=9.0 Hz), 7.38-7.34 (m, 2H), 7.29-7.26 (m, 3H), 7.15 (s, 1H), 7.11 (d, 1H, J=3.5 Hz), 6.80 (d, 1H, J=4.0 Hz), 6.65 (d, 1H, J=9.0 Hz), 6.31 (d, 1H, J=2.5 Hz), 2.70 (s, 3H, CH3).

6-Nitro-1-methyl-2-(5-(2-methylthiazol-4-yl)thiophen-2-yl)-3-phenyl-2,3-dihydroquinazolin-4(1H)-one (DABL-NM, 5, Scheme 1): 6-Nitro-2-(5-(2-methylthiazol-4-yl)thiophen-2-yl)-3-phenyl-2,3-dihydroquinazolin-4(1H)-one (4) (50 mg, 0.11 mmol) was carefully added to a suspension of NaH (6 mg, 0.22 mmol, 10 mg of 60% in mineral oil, prewashed with hexanes) in anhydrous THF (10 mL). The resulting mixture was stirred at 0° C. for 1 hr, MeI (31 mg, 0.22 mmol) was added dropwise and the reaction was allowed to proceed overnight at room temperature. The reaction flask was cooled down to 0° C., and the reaction mixture was quenched with saturated NaHCO$_3$. The aqueous layer was extracted with CH$_2$Cl$_2$ (3×30 ml), washed with 1N HCl (2×10 mL), dried over MgSO$_4$, filtered, and evaporated to dryness. The crude product was purified over silica gel column by eluting with EtOAC:hexane (2:8) to give 6-Nitro-1-methyl-2-(5-(2-methylthiazol-4-yl)thiophen-2-yl)-3-phenyl-2,3-dihydroquinazolin-4(1H)-one (5) in 71% yield. $^1$H NMR (500 mHz, CDCl$_3$) δ (ppm): 9.0 (d, 1H, J=2.5 Hz), 8.33 and 8.31 (dd, 1H, J=2.5 Hz and J=9.0 Hz), 7.43-7.39 (m, 2H), 7.35-7.28 (m, 3H), 7.19 (d, 1H, J=3.5 Hz), 7.18 (ds, 1H), 6.85 (d, 1H, J=3.5 Hz), 6.72 (d, 1H, J=9.0 Hz), 6.09 (s, 1H), 3.16 (s, 3H, NCH$_3$), 2.72 (s, 3H, CH$_3$).

Scheme II: General synthesis of DABL-N and DABL-M analogs

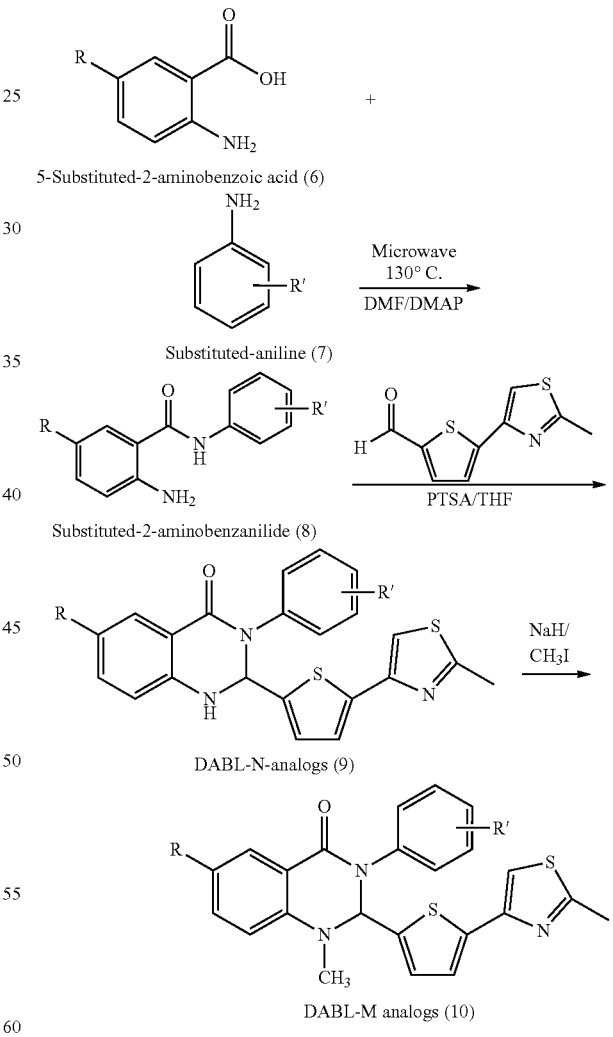

General Synthesis DABL-N and DABLM Analogs

5-Cyano-N-phenylbenzamide: 5-cyano-2-aminobenzoic acid (6 Scheme II) (100 mg, 0.62 mmol) was mixed with aniline (69 mg, 0.74 mmol), DMSO (0.5 mL), and catalytic amount of DMAP (3 mg) in a microwave glass vial that was irradiated in a microwave (LABMAT) at 130° C., 250 W for 30 min. After the reaction mixture was cooled to ambient temperature, the reaction mixture diluted with ethyl acetate and sonicated to dissolve the entire residue. The organic fraction was washed with water (3×10 mL), dried over MgSO$_4$, filtered, and evaporated to give the crude product. Flash chromatography [eluted with hexane:Ethyl acetate (80/20)] afforded 5-cyano-N-phenylbenzamide (8, Scheme II) (123 mg, 84%) as pale yellow powder. $^1$H-NMR (500 MHz, D4-MeOH) δ (ppm)=8.04 (d, 1H, J=1.8 Hz), 7.66 (d, 2H, J=8.4 Hz), 7.50 and 7.48 (dd, 1H, J=1.8 Hz, J=9.0 Hz), 7.37 (t, 2H, J=7.2 Hz and J=7.8 Hz), 7.17 (t, 1H, J=8.4 Hz, J=7.2 Hz), 6.86 (d, 1H, J=9.0 Hz).

6-Cyano-2-(5-(2-methylthiazol-4-yl)thiophen-2-yl)-3-phenyl-2,3-dihydroquinazolin-4(1H)-one (DABL-CN, 9, Scheme II): 5-Cyano-N-phenylbenzamide (8, Scheme II) (205 mg, 0.87 mmol) and 5-(2-methylthiazol-4-yl)thiophene-2-carbaldehyde (200 mg, 0.95 mmol) were dissolved in THF (12 mL) and a catalytic amount of PTSA (16 mg, 0.09 mmol) was added. The reaction mixture was refluxed overnight. After evaporation to dryness the crude mixture was purified by flash chromatography on silica gel using hexane/ethyl acetate (80/20) to yield 6-Cyano-2-(5-(2-methylthiazol-4-yl)thiophen-2-yl)-3-phenyl-2,3-dihydroquinazolin-4(1H)-one (9, Scheme II) as yellow powder (237 mg, 64%). $^1$H-NMR (500 MHz, CDCl$_3$) δ (ppm)=8.37 (d, 1H, J=1.8 Hz), 7.60 and 7.59 (dd, 1H, J=1.8 Hz and J=8.4 Hz), 7.42-7.39 (m, 2H), 7.33-7.29 (m, 3H), 7.19 (s, 1H), 7.17 (d, 1H, J=3.6 Hz), 6.86 (d, 1H, J=3.6 Hz), 6.77 (d, 1H, J=8.4 Hz), 6.37 (d, 1H, J=3.0 Hz), 5.37 (d, 1H, J=2.4 Hz), 2.75 (s, 3H, CH3).

6-Cyano-1-methyl-2-(5-(2-methylthiazol-4-yl)thiophen-2-yl)-3-phenyl-2,3-dihydroquinazolin-4(1H)-one (DABL-CM, 10, Scheme II): 6-Cyano-2-(5-(2-methylthiazol-4-yl)thiophen-2-yl)-3-phenyl-2,3-dihydroquinazolin-4(1H)-one (4) (120 mg, 0.28 mmol) was carefully added to a suspension of NaH (13 mg, 0.56 mmol, 23 mg of 60% in mineral oil, prewashed with hexanes) in anhydrous THF (10 mL). The resulting mixture was stirred at 0° C. for 1 hr, MeI (80 mg, 0.56 mmol) was added dropwise and the reaction was allowed to proceed overnight at room temperature. The reaction flask was cooled down to 0° C., and the reaction mixture was quenched with saturated NaHCO$_3$. The aqueous layer was extracted with CH$_2$Cl$_2$ (3×30 ml), washed with 1N HCl (2×10 mL), dried over MgSO$_4$, filtered, and evaporated to dryness. The crude product was purified over silica gel column by eluting with EtOAC:hexane (2:8) to give 6-Cyano-1-methyl-2-(5-(2-methylthiazol-4-yl)thiophen-2-yl)-3-phenyl-2,3-dihydroquinazolin 4(1H)-one (5) in 92% yield. $^1$H NMR (600 mHz, CDCl$_3$) 8.42 (d, 1H, J=1.8 Hz), 7.69 and 7.67 (dd, 1H, J=2.4 Hz and J=9.0 Hz), 7.43-7.40 (m, 2H), 7.35-7.29 (m, 3H), 7.20 (d, 1H, J=4.2 Hz), 7.19 (s, 1H), 6.84 (d, 1H, J=3.6 Hz), 6.73 (d, 1H, J=9.0 Hz), 6.07 (s, 1H), 3.11 (s, 3H, N—CH3), 2.74 (s, 3H, CH3).

Figure 15A:
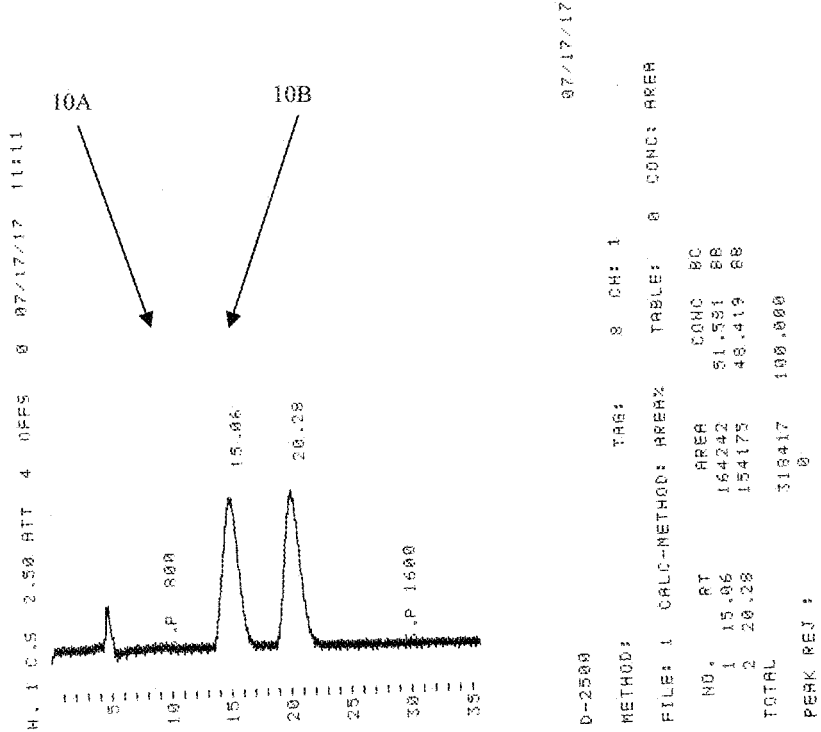
FIGS. 15A-15E illustrate support for the formation of enantiomers.
Figure 15B:
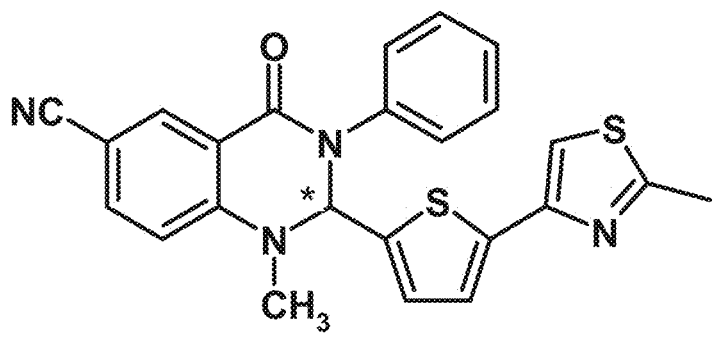
Figure 15C:
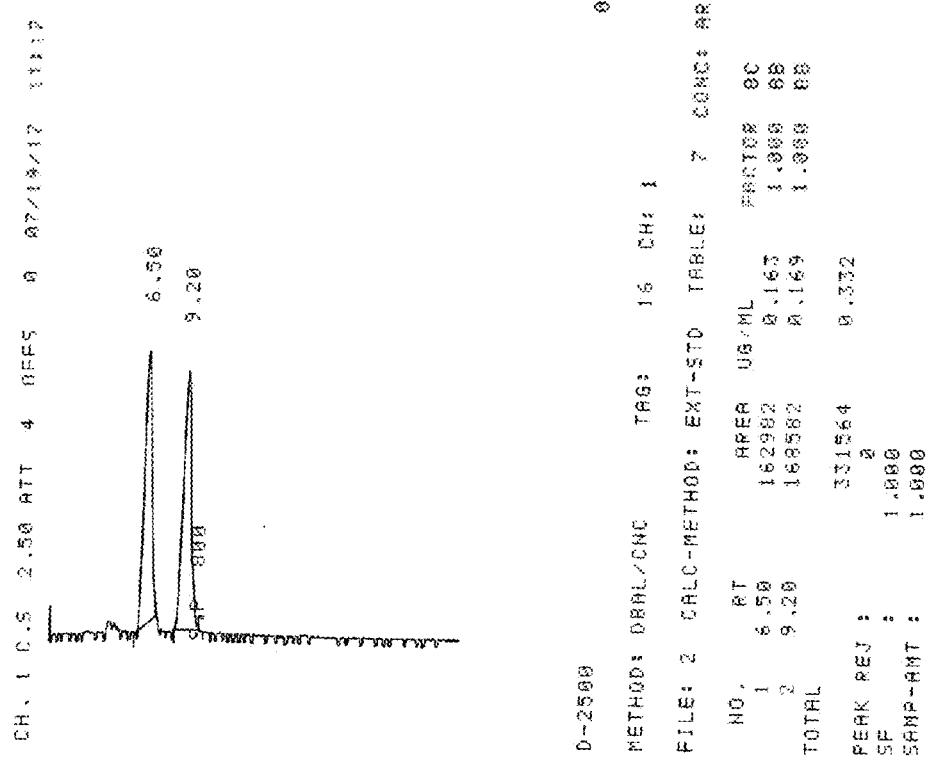
Figure 15D:
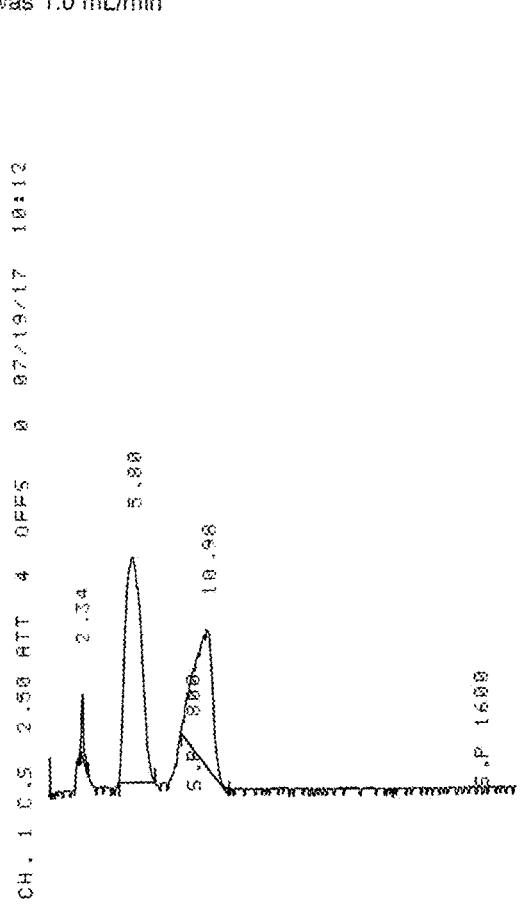
Figure 15E:
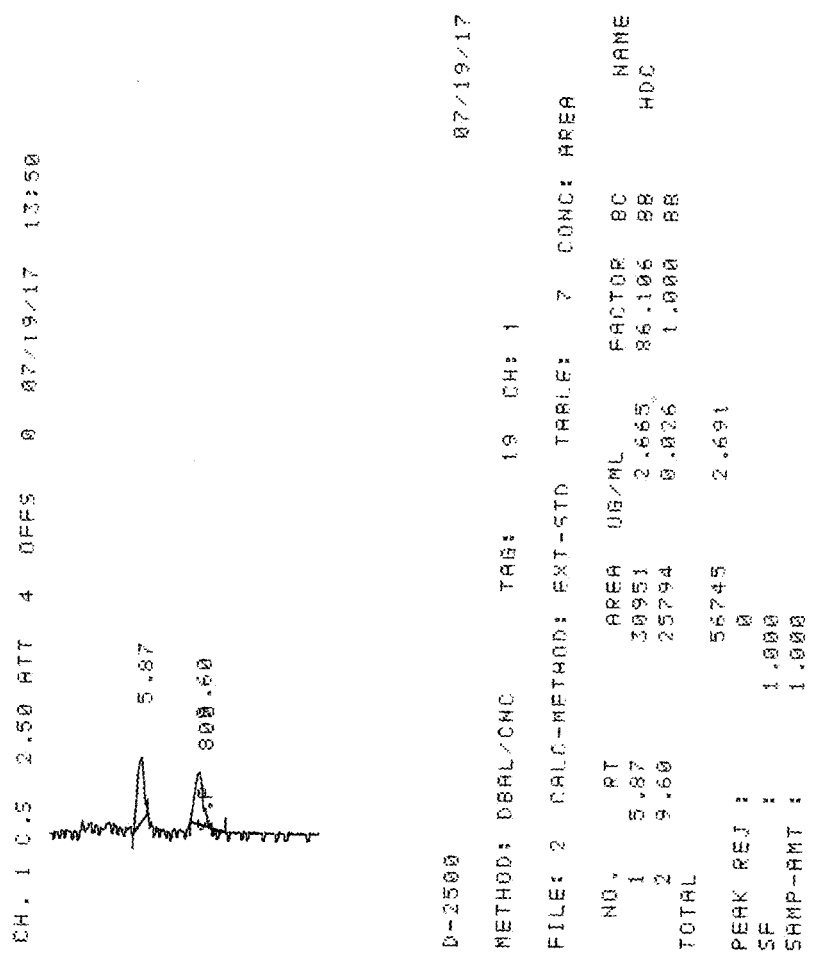

FIG. 15A illustrates the chromatographic separation of DABL-CM enantiomers, (10, Scheme II). A chiral phase HPLC separation of DABL-CM was performed on a Phenomenex LUX 5 μm Cellulose-1 normal phase column. Briefly, an HPLC normal phase system (Waters 510 pump) equipped with UV detector (Waters 2487) was employed. The HPLC traces were recorded on Hitachi D-2500 printer. Phenomenex 150×4.6 mm stainless steel column packed with Cellulose-1 was used for analysis. The mobile phase was a mixture of hexane/ethanol (70/30) with 0.1% diethylamine. Flow rate was 1.0 mL/min. Injection volume was 25 uL. All chromatograms were recorded at 254 nm. The retention times for the first (10a) and second (10b) eluted enantiomers of DABL-CM were 15.06 and 20.28 min, respectively. The configuration of the stereo center in position 2, see * on FIG. 15B, is crucial for activity. Each reaction that produces the cyclic compound (compound 4 and 5 in the scheme) at position 2 will generate the chiral center and two stereoisomers. The reaction will generate the racemic mixtures. DABL-CN, DABL-N and DABL-NM were also evaluated accordingly and found to exist as a racemic mixture having two stereoisomers (enantiomers). FIG. 15C illustrates the chromatographic separation of DABL-NM enantiomers. FIG. 15D illustrates the chromatographic separation of DABL-CN enantiomers. FIG. 15E illustrates the chromatographic separation of DABL-N enantiomers. Accordingly, the compounds of current inventions and methods described throughout include stereoisomers (enantiomers), or racemic or nonracemic mixture of stereoisomers.

Results

HCMV Differentially Regulates SNARE Protein Levels During Infection.

Figures 8A, 8B:
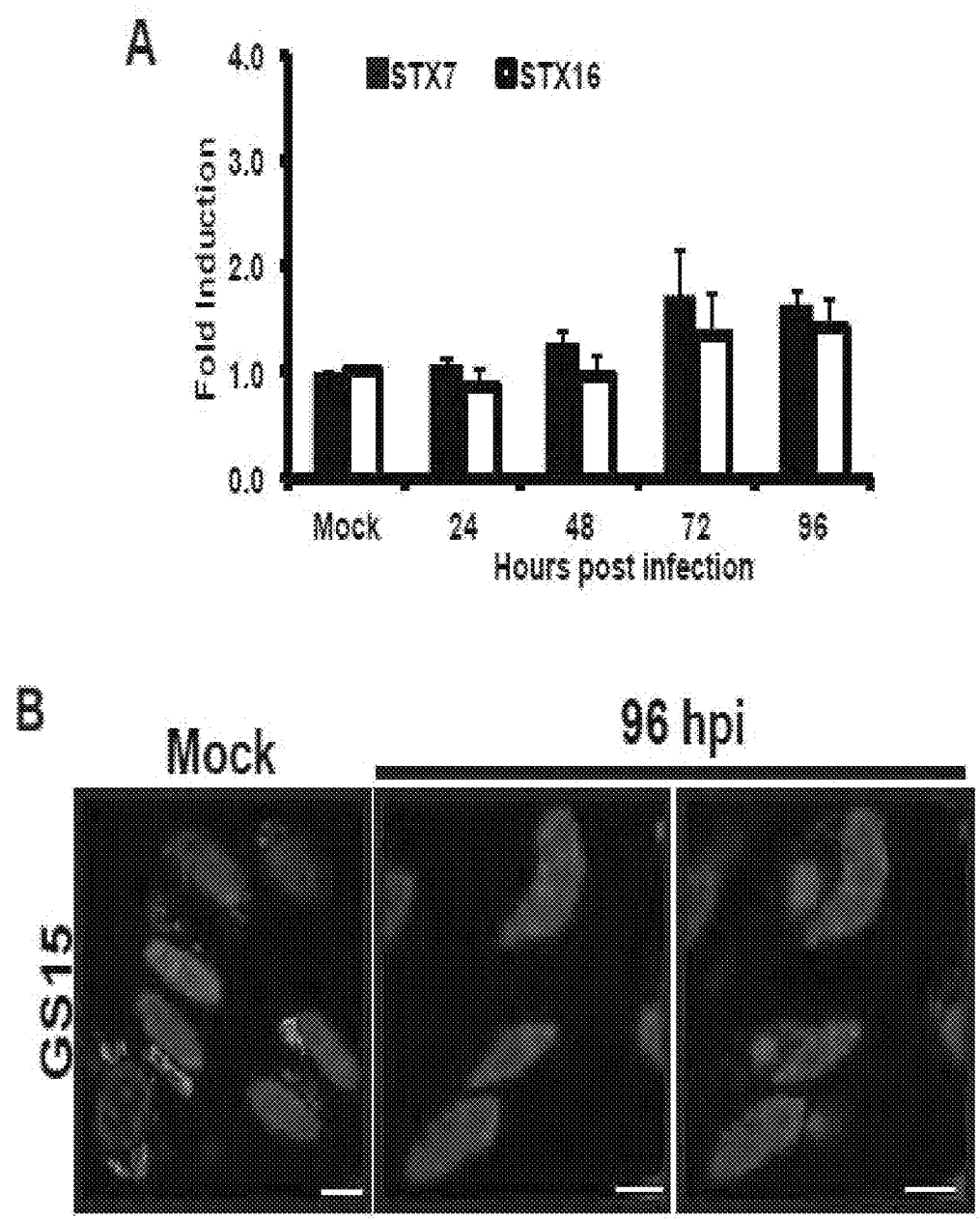
FIGS. 8A and 8B show SNARE regulation by HCMV.

A striking morphological characteristic of the cVAC is reorganization of the Golgi apparatus into a perinuclear ring. It was hypothesized that cellular proteins involved in regulating membrane flow to and from the Golgi, including the membrane fusion promoting SNARE proteins, are important for cVAC formation and that HCMV may regulate these proteins during infection. SNARE proteins are structurally classified into Qa, Qb, Qc and R SNAREs (Fasshauer D, et al. *Proc Natl Acad Sci USA*. 1998; 95(26):15781-6), and the investigation began by focusing on the Qa SNARES of the syntaxin family associated with Golgi-related trafficking (FIG. 1A). Analysis of steady state protein levels during infection revealed several interesting observations. Protein levels of STX7, which regulates trafficking to the late endosome and lysosome, and STX16, which is involved in retrograde transport from endosomes to the TGN, do not change during the course of infection (FIG. 1B). However, STX18, involved in anterograde trafficking from the endoplasmic reticulum (ER) to the ER-Golgi intermediate compartment (ERGIC) was downregulated early in infection and stayed depressed throughout infection. In contrast, STX5 was increased during infection, reaching peak levels late in infection (FIG. 1B). Interestingly, no significant changes were detected in the transcript levels of any of these SNAREs, including STX18 and STX5, suggesting that the observed changes in these protein levels occur at a posttranscriptional level (FIGS. 1C & 8A). Since the increase in STX5 corresponds temporally with the presence of the cVAC, these studies were focused on STX5. STX5 is normally localized to the Golgi apparatus in uninfected cells where it functions in retrograde, anterograde and intra-Golgi trafficking. During infection, STX5 localizes to a ring of the cVAC similar to other Golgi markers, placing STX5 in position to play a functional role in cVAC morphology (FIG. 1D).

STX5 is a component of three different functional SNARE complexes (FIG. 1E). In one complex, STX5 binds to GS27 (membrin, GOSR2) and Sec22b (ERS24) to bind vesicles containing Bet1, mediating ER to Golgi and early intra-Golgi transport (Xu D, et al. *J Biol Chem*. 2000; 275(50):39631-9). STX5 also interacts with GS28 (GOSR1) and Ykt6. This complex can interact with Bet1 containing vesicles to mediate a late stage of ER to Golgi trafficking (Zhang T, et al. *J Biol Chem*. 2001; 276(29):27480-7) and with GS15 for trafficking in the Golgi and from early endosomes to the trans-Golgi network (TGN) (Xu Y, et al.

*Mol Biol Cell.* 2002; 13(10):3493-507; Tai G, et al. *Mol Biol Cell.* 2004; 15(9):4011-22). The protein levels of each of the STX5-containing SNARE complex members were investigated during infection. It was hypothesized that HCMV would increase the protein levels of the other members of one or both complexes, similar to STX5. The differential regulation of one complex compared to the other may provide insight into which of these complexes are functionally important for infection. Interestingly, although unique regulation of the other SNARE proteins was observed, none of the other subunits mirrored the STX5 increase during infection (FIG. 1F). In fact, the most striking result was the drastic downregulation of the v-SNARE GS15 observed by a loss of signal in both Western blot analysis and immunofluorescence (FIGS. 1F & 8B). The loss of GS15 persisted throughout infection and is noteworthy considering GS15 is present in molar excess over STX5 in uninfected cells (Volchuk A, et al. *Mol Biol Cell.* 2004; 15(4):1506-18). Thus, this ratio is completely inverted by HCMV during infection. No other SNAREs were induced during the late stages of infection, indicating that this induction is specific for STX5.

Since the expression data did not provide insight into which of the STX5 complexes were functionally important during infection, the localization of the STX5-interacting SNAREs was investigated. As with STX5, these proteins are normally localized to the Golgi apparatus in mock cells. However, while STX5 is located throughout the Golgi, the other SNAREs preferentially locate to different compartments of the Golgi to form a gradient important for mediating the different types of Golgi trafficking (Volchuk A, et al. *Mol Biol Cell.* 2004; 15(4):1506-18). During infection, the two Qb SNARES that interact with STX5, GS28 and GS27, both localized to a ring of the assembly compartment, which is expected due to their normal association with other Golgi markers (FIG. 1G). More importantly, these proteins localize to a similar ring-like structure as STX5, placing them in a position to function with STX5 during infection.

STX5 is Functionally Important for HCMV Infection.

Figures 2A, 2B, 2C, 2D:
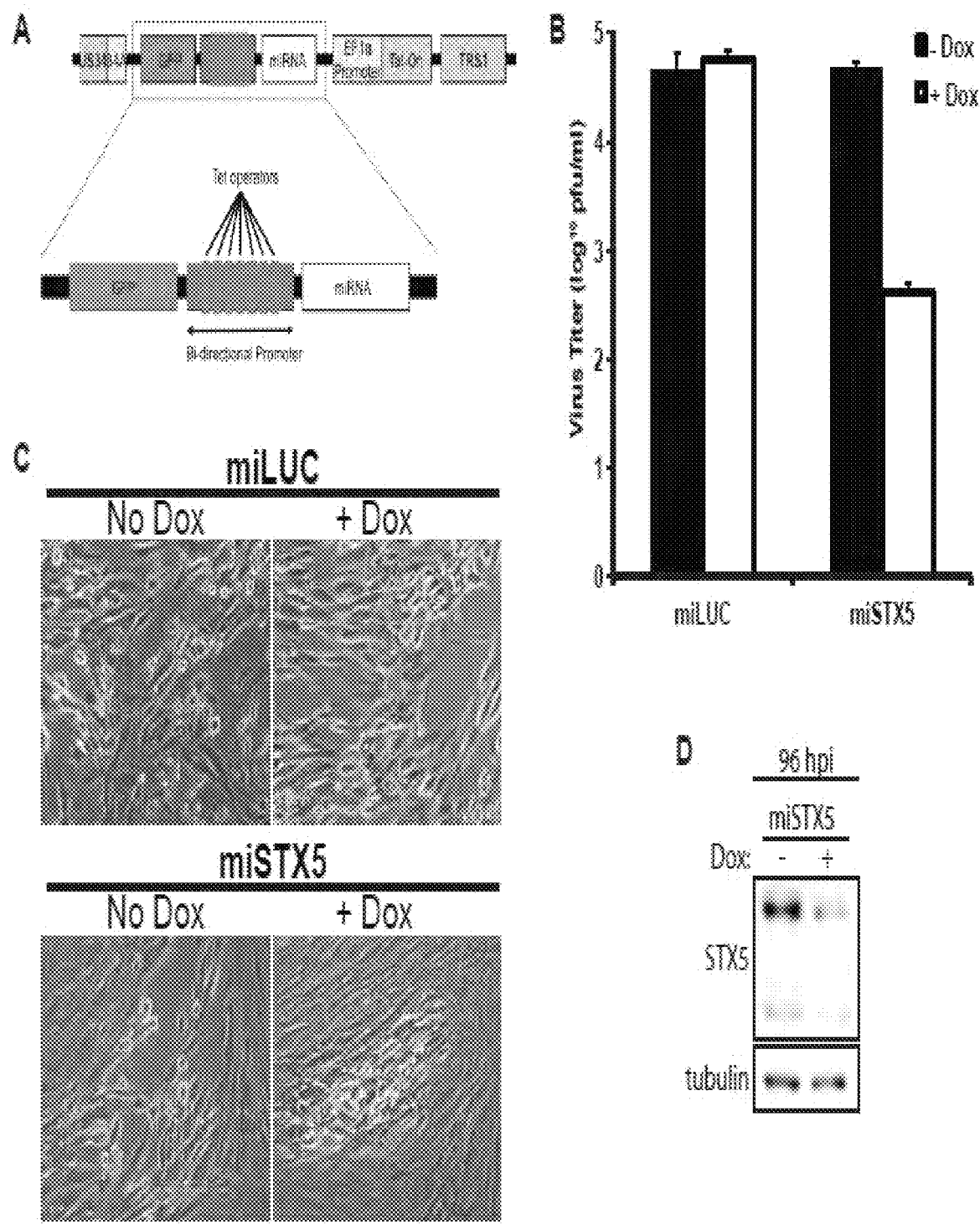
FIGS. 2A-2D show that STX5 is required for infection.

Since STX5 is upregulated late in infection and localizes to a ring of the cVAC, it was hypothesized that it was functionally important for infection. To test this, a miRNA sequence targeting STX5 was designed and engineered into the viral genome between the UL34a and TRS1 loci. Since this hypothesis predicts that expression of this construct would be detrimental to the production of infectious virions, it was sought to utilize an inducible promoter to drive the expression of the miRNA. Since previous attempts at utilizing inducible promoters in the viral genome have reported a large degree of leaky expression, a bidirectional promoter was utilized to express both GFP and the miRNA cassette, providing a way to visually monitor expression of the inducible construct (FIG. 2A). Using this miSTX5 virus and a control virus expressing a microRNA against luciferase (miLUC), cells were infected at a low MOI (0.05 pfu/ml). Doxycyline was added to a subset of both miSTX5 and miLuc samples at 2 hpi and the media was spiked with fresh doxycycline every three days throughout infection. Cells and supernatant were harvested at 9 days post infection (dpi) for growth curve analysis. There was no difference in the titers between the miLUC samples with or without doxycycline. In contrast, viral titers from the miSTX5 doxycycline-treated samples were decreased by about 2 logs compared to the untreated miSTX5 samples, providing evidence that STX5 is functionally important for infection (FIG. 2B). The lower viral titer corresponded with decreased viral spread and less cytopathic effects (CPE) in the monolayer (FIG. 2C). Since the knockdown of STX5 only occurred in viral infected cells, slowed the spread of infection and as a result was present in only a subset of the cells, Western blot analysis of these samples would not adequately depict the level of knockdown. To check the level of STX5 protein knockdown by miSTX, cells were infected with miSTX5 at an MOI of 3 with or without doxycycline added at 2 hpi harvested cell lysates at 96 hpi for Western blot analysis. STX5 protein levels were greatly reduced in the presence of doxycycline (FIG. 2D), thus correlating the lower titers with reduced levels of STX5 protein.

Figures 3A, 3B, 3C, 3D, 3E:
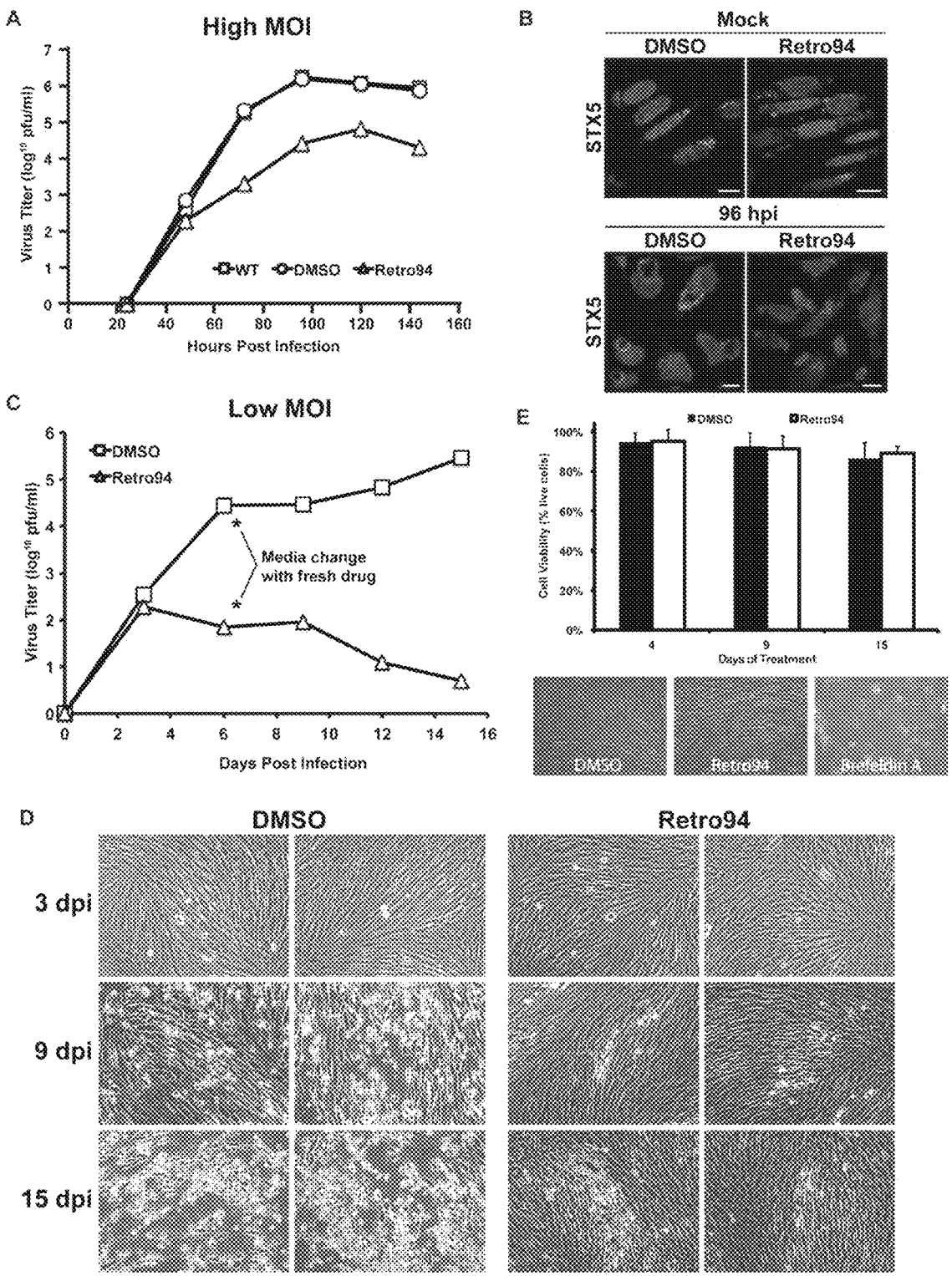
FIGS. 3A-3E show that Retro94 blocks the efficient production of infectious HCMV virions.

For a second functional test of STX5 during infection, a compound that promotes the mislocalization of STX5 was used. Two compounds identified in a recent screen blocked the trafficking and subsequent toxicity of bacterial Shiga-like toxins (Stechmann B, et al. *Cell.* 2010; 141(2):231-42). Further analysis of trafficking factors revealed that STX5 was displaced from the Golgi apparatus after treatment with the compounds. Subsequent optimization of one of the original compounds led to a more potent version named Retro94 (Noel R, et al. *J Med Chem.* 2013; 56(8):3404-13). Since HCMV upregulates STX5 late in infection, which is displaced by Retro94, it was hypothesized that Retro94 would inhibit HCMV replication, presumably at a late stage. Addition of Retro94 two hours after a high MOI infection (3 pfu/cell) reduced production of infectious of virions by greater than two logs (FIG. 3A). The localization of STX5 was checked after treatment to verify that Retro94 could still alter its localization in infected cells. As previously reported (Noel R, et al. *J Med Chem.* 2013; 56(8):3404-13), STX5 lost its Golgi-localization after treatment with Retro94 in uninfected cells and was dispersed throughout the cells (FIG. 3B). In infected cells, STX5 was also dispersed throughout the cell and was not located to the cVAC ring (FIG. 3B). Thus, both knockdown of STX5 by miRNA and displacement of STX5 by Retro94 resulted in reduced production of infectious virions.

The step in which HCMV replication was blocked by Retro94 was then investigated. Since the results with the miSTX5 virus indicated reduced viral spread, growth curve analyses were conducted on low MOI infections (0.05 pfu/cell) of cells treated with Retro94 or the vehicle control (DMSO). Since the stability of Retro94 in media remains to be determined, media was exchanged 6 days post infection (dpi) and fresh drug was added. While the control treated infection continued to progress after the media change, the Retro94 treated samples never recovered. At 15 dpi, there was a five log reduction in the amount of infectious virus produced (FIG. 3C). Visualization of the monolayer at 3 dpi showed little difference between the Retro94 and control treated samples with small foci of infection detectable in both treatments (FIG. 3D). However, by 9 dpi the control treated infection had spread with areas of visible clearing present. In contrast, the spread of the infection was limited in Retro94 treated cells. By 15 dpi, the entire control-treated monolayer exhibited CPE, while much of the Retro-94 treated monolayer remained intact with only a few distinct foci of infection that were slightly larger than those present at 9 dpi (FIG. 3D).

Taken together, these results evidence a direct role for STX5 in HCMV replication. However, the extended treatment of cells with drug for the duration of infection may result in unhealthy cells that are unable to support infection. It was found that treatment of cells with Retro94 for 4, 9 or 15 days had no effect on cell viability or cell morphology (FIG. 3E). This is in contrast to another trafficking inhibitor that is known to be toxic after extended treatment, Brefeldin A, in which very few cells in the monolayer remained after 96 hours of treatment. Thus, the effect of Retro94 on HCMV replication is unlikely to be a result of toxicity to the cells.

Retro-94 Alters Formation of the Cytoplasmic Viral Assembly Compartment.

Figures 4A, 4B, 4C, 4D, 4E, 4F:
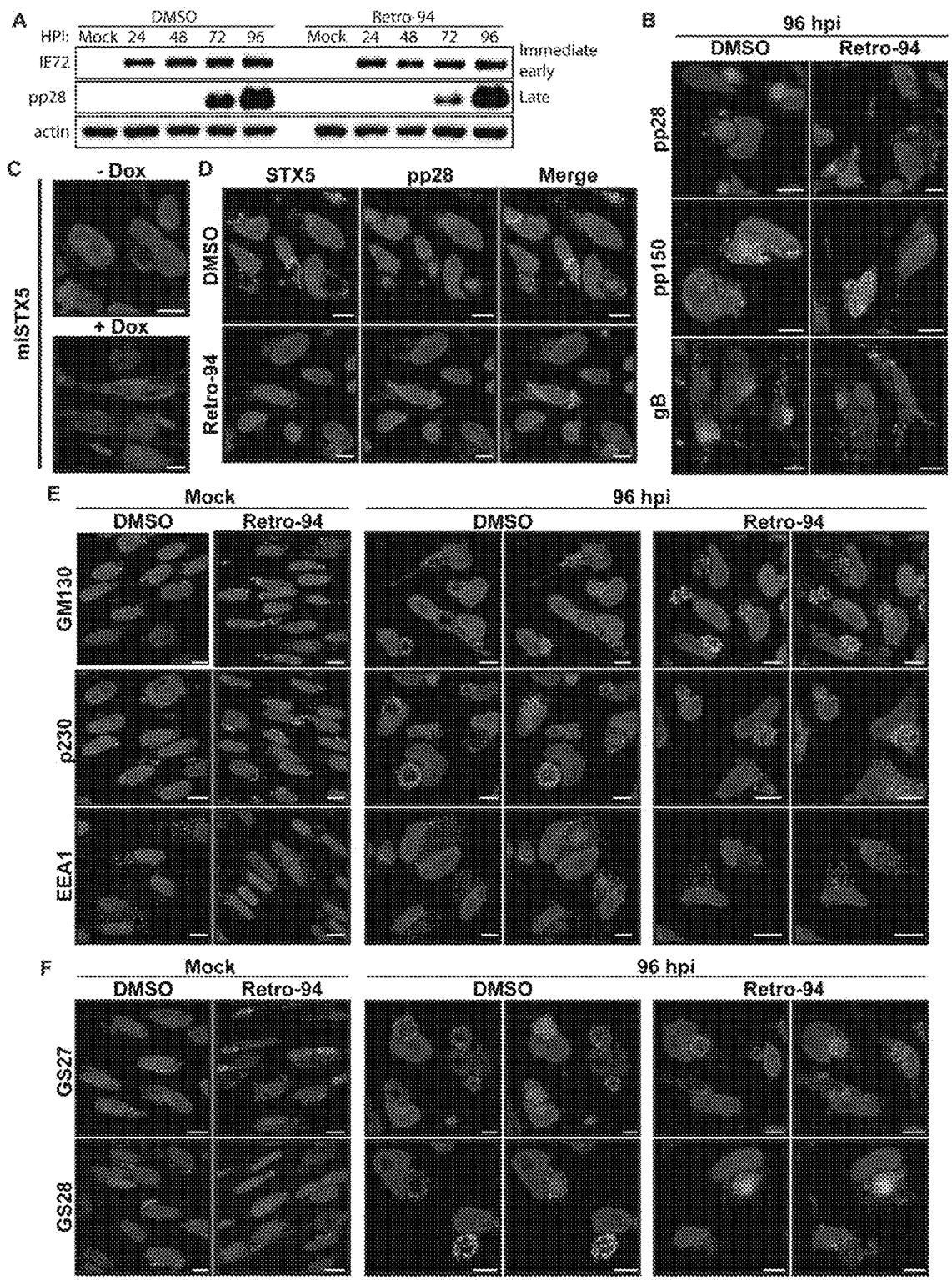
FIGS. 4A-4F show that Retro94 alters morphology of the HCMV assembly compartment.

The reduced viral spread can be a result of a block at a number of different stages in virus replication, including a block in entry or assembly. Retro94 has previously been shown to block the entry of several viruses, including polyomavirus and papillomavirus (Carney D W, et al. *Bioorg Med Chem.* 2014; 22(17):4836-47). Since HCMV does not share the entry pathway of these viruses, it was not anticipated that Retro94 would affect virus entry. In fact, analysis of the infected monolayers revealed that treated cells exhibited initial characteristics of CPE, suggesting that infection was established in the presence of Retro94. It was reasoned that the Retro94-mediated relocalization of STX5 was affecting a later stage in replication, such as assembly, consistent with the cVAC localization of STX5. To further investigate this, a steady state analysis of viral proteins was conducted. Western blot analysis of lysates from control and Retro94 treated samples showed that steady state levels of immediate-early and late proteins were not affected, confirming that infection was established and had progressed to production of late proteins (FIG. 4A). The presence of late proteins also indicated that DNA replication had occurred. These results support a late block in either assembly or spread, as was also suggested by the CPE. Although Retro94 did not affect the synthesis of viral proteins, it was observed that STX5 protein did not reach the same level as observed in control-treated samples. Thus, Retro94 either prevents this HCMV-mediated increase from occurring or promotes the degradation of STX5, obscuring the increase normally observed during infection.

Since STX5 localized to the Golgi-ring of the cVAC and appeared to affect a late stage in infection, it was investigated whether disruption of STX5 with Retro94 alters cVAC morphology. We investigated the localization of three viral proteins known to localize to the perinuclear cVAC, pp28, pp150 and glycoprotein B. In the presence of Retro94, all three viral proteins were dispersed throughout the cytoplasm and were no longer present in the cVAC (FIG. 4B). Similarly, pp28 was also dispersed in cells infected with miSTX5 and treated with doxycycline (FIG. 4C). Since both STX5 and the viral proteins were dispersed throughout the cytoplasm in the presence of Retro94, it was investigated whether STX5 and pp28 colocalized. There was not a high degree of colocalization and for the most part they were dispersed to distinct regions (FIG. 4D). It was next reasoned that similar to STX5 and the viral proteins, that cellular markers of the cVAC would also be dispersed throughout the cytoplasm. Interestingly, it was found that markers of the Golgi Apparatus (GM130), TGN (p230) and endosomes (EEA1) retained their perinuclear localization (FIG. 4E). However, the Golgi and TGN rings characteristic of normal cVAC morphology were collapsed. Thus, normal cVAC morphology did not form in the presence of Retro94.

Since Retro94 altered STX5 localization in a manner that was clearly distinct from other Golgi markers, it was queried whether other STX5-complex members were also dispersed. The localization of the two Qb SNARES that form a complex with STX5, GS27 and GS28 was investigated. It was found that GS27 and GS28 mostly remained in a perinuclear localization after Retro94 treatment, similar to other Golgi markers (FIG. 4F). Thus, the cytoplasmic dispersion of STX5 in infected cells was specific for STX5 and not for other complex members. This result was consistent with that published for the parent compound Retro-2 (Stechmann B, et al. *Cell.* 2010; 141(2):231-42).

Figures 5A, 5B, 5C, 5D, 5E, 5F, 5G, 5H, 5I:
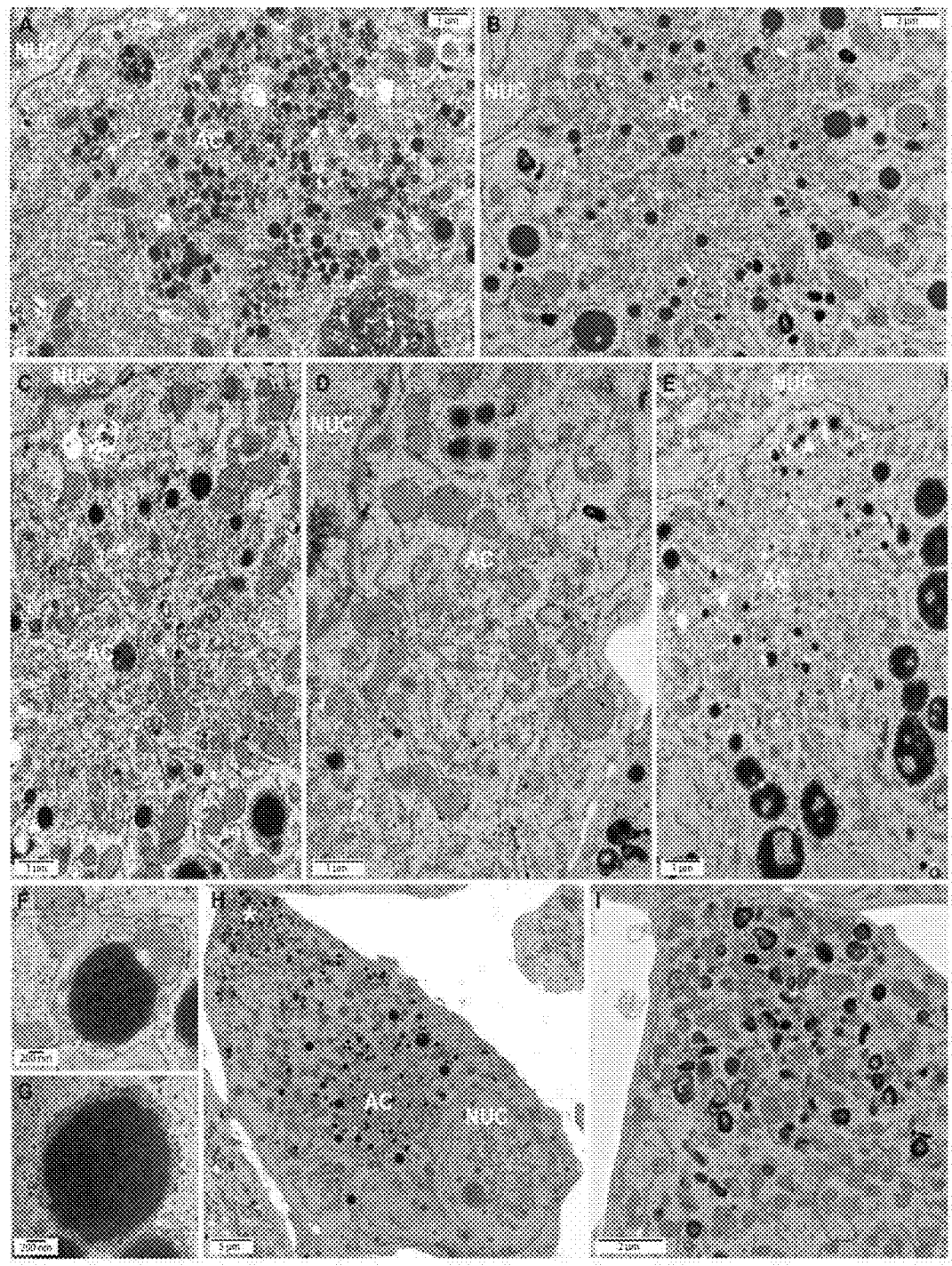
FIGS. 5A-5I show that Retro94 results in reduced cytoplasmic viral activity. Electron micrographs of HCMV-infected cells (MOI=3) at 96 hpi treated with (FIG. 5A) DMSO or (FIGS. 5B-5I) Retro94 at 2 hpi. Asterisk in (FIG. 5H) indicates peripheral accumulation of viral activity. AC, assembly compartment. Nuc, nucleus

To further examine the effect of Retro94 on cVAC formation and viral assembly, EM electron microscopy was performed on infected cells treated with drug or vehicle. In vehicle-treated cells, a perinuclear region of intense viral activity was observed. There were a number of capsids at varying stages of tegumentation and envelopment present in this region, as well as dense bodies (FIG. 5A). A perinuclear accumulation of membranes and dense bodies was present in Retro94 treated cells, features implicating it as an area representing a potential cVAC (FIGS. 5B-5E). This accumulation of membranes visualized by EM likely coincides with the IF depicting cellular cVAC markers persisting in a perinuclear localization after Retro94 treatment (FIG. 4E). Despite the presence of membrane and dense bodies, this perinuclear region was largely devoid of capsids at all stages of maturation, although they were occasionally present in some cells (FIG. 5C). An increase in large, sometimes greater than one micron long, dense bodies likely representing a form of degradative organelle were found associated with these areas, particularly at the periphery of this membranous area (FIGS. 5F & 5G). In a subset of cells, in addition to this perinuclear accumulation, a region at the periphery of the cell was enriched for degradative organelles, mitochondria and the occasional viral capsid (FIGS. 5H & 5I). In many ways this peripheral area resembled the perinuclear cVAC-like region. Taken together, these results agree well with the IF data and confirm that Retro94 treatment disrupts the normal morphology and viral activity associated with the cVAC.

The Efficiency of Retro94-Mediated Inhibition of HCMV is Dependent on Time of Addition and Concentration.

Figures 6A, 6B, 6C:
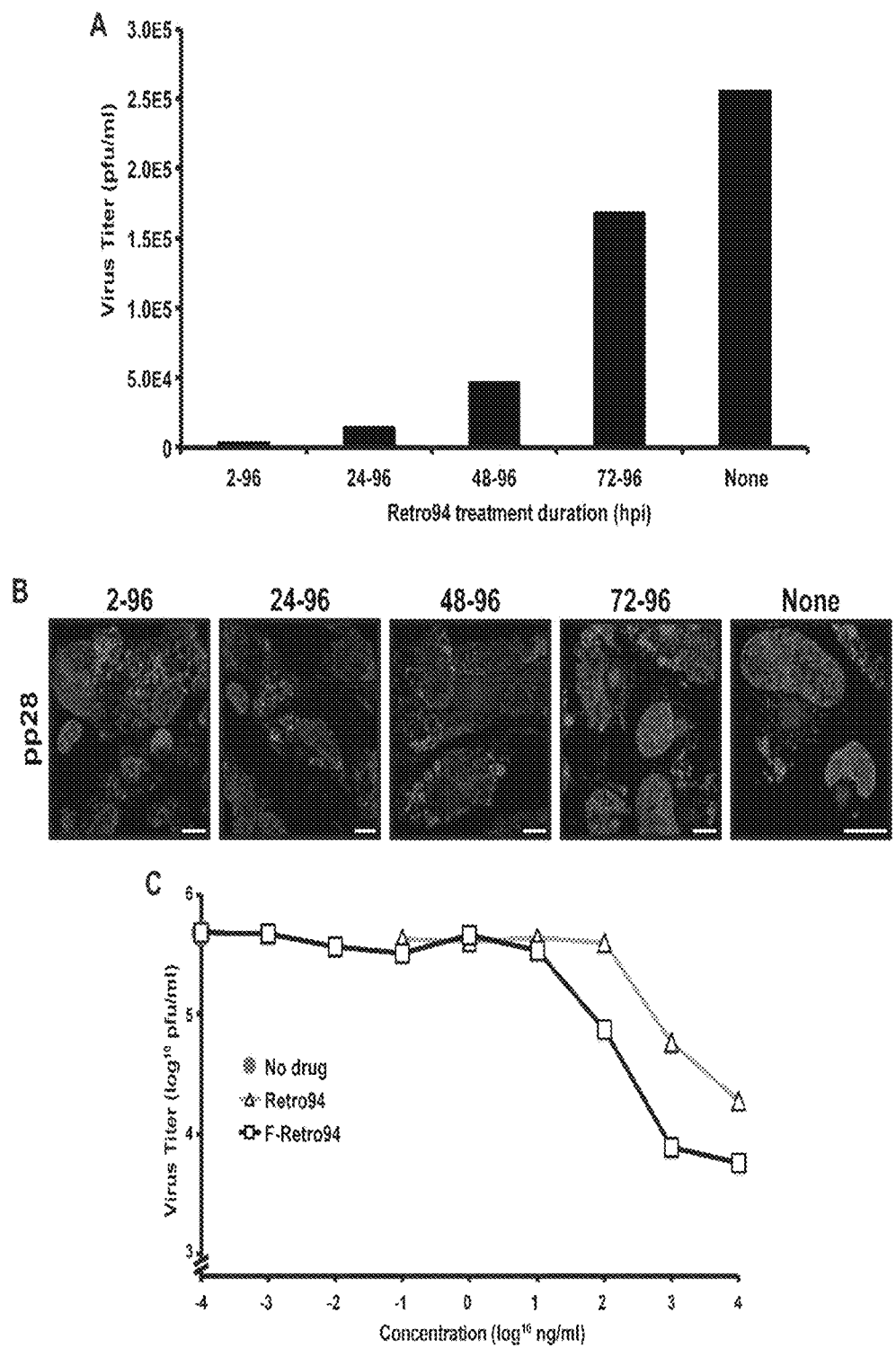
FIGS. 6A-6C show the temporal and concentration-dependent effects on Retro94 inhibition of HCMV.

Thus far, the data supported a late block in HCMV replication, likely due to the morphologically altered cVAC. For these experiments, Retro94 was either added simultaneously with virus or after the absorption phase at 2 hpi. Since Retro94 acts late in infection, it was hypothesized that it could block replication even if added at later times throughout infection. To test this, Retro94 was added to infected cells (MOI=3) at 2, 24, 48 and 72 hours post infection and cells and supernatant were harvested for growth curves. Addition at 2 hpi resulted in a two log reduction in infectious virion production. Although the greatest inhibition was observed when Retro94 was added at 2 hpi, a significant reduction in infectious virion production was also observed at 24 hpi (20 fold) and less so at 48 hpi (5 fold) (FIG. 6A). Addition of drug at 72 hpi, when the assembly compartment is fully formed and virion production is well underway, still resulted in about a twofold reduction in infectious virion production.

This inhibition was then correlated in infectious virion production with the morphology of the assembly compartment. Cells were infected with HCMV that expresses pp28-mCherry with an MOI of 3. Retro94 was added at 2, 24, 48 and 72 hours post infection and the assembly compartment was imaged at 96 hpi by visualizing pp28-mCherry. In cells treated at 2 or 24 hpi, pp28 was dispersed throughout the cell and no area representing a cVAC was detected (FIG. 6B). Addition of drug at 48 hpi was associated with pp28 being largely dispersed throughout the cell as well; however light regions of pp28 in a perinuclear location reminisicent of the cVAC were detectable. In contrast, these areas were more prominent when Retro94 was added at 72 hpi, although in some cells it appeared that pp28 was beginning to be dispersed from these regions (FIG. 6B). Thus, it appears that although Retro94 may affect the morphology of established assembly compartments, it's most pronounced effect was observed when added before or at the early stages of cVAC formation.

The concentration of Retro94 required to inhibit production of infectious HCMV virions was next determined. Ten-fold dilutions of Retro94 were added at 2 hpi to cells infected at an MOI of 3 and growth curve analyses were performed at 96 hpi. The dilution at which a significant inhibition in viral titers was first present was 1 µM (FIG. 6C). The $IC_{50}$ was calculated to be around 130 nM. Recent studies on Retro94 have identified derivatives that exhibit more potency, including addition of a fluorine (Gupta N, et al. *ACS Med Chem Lett.* 2014; 5(1):94-7). It was tested next whether this derivative of Retro94 would have increased potency against HCMV. It was found that F-Retro94 was in fact more effective in reducing HCMV titers, decreasing the $IC_{50}$ by about a log to ~15 nM. Thus, a potent inhibitor of HCMV that is well tolerated by cells was identified.

Figures 7A, 7B, 7C:
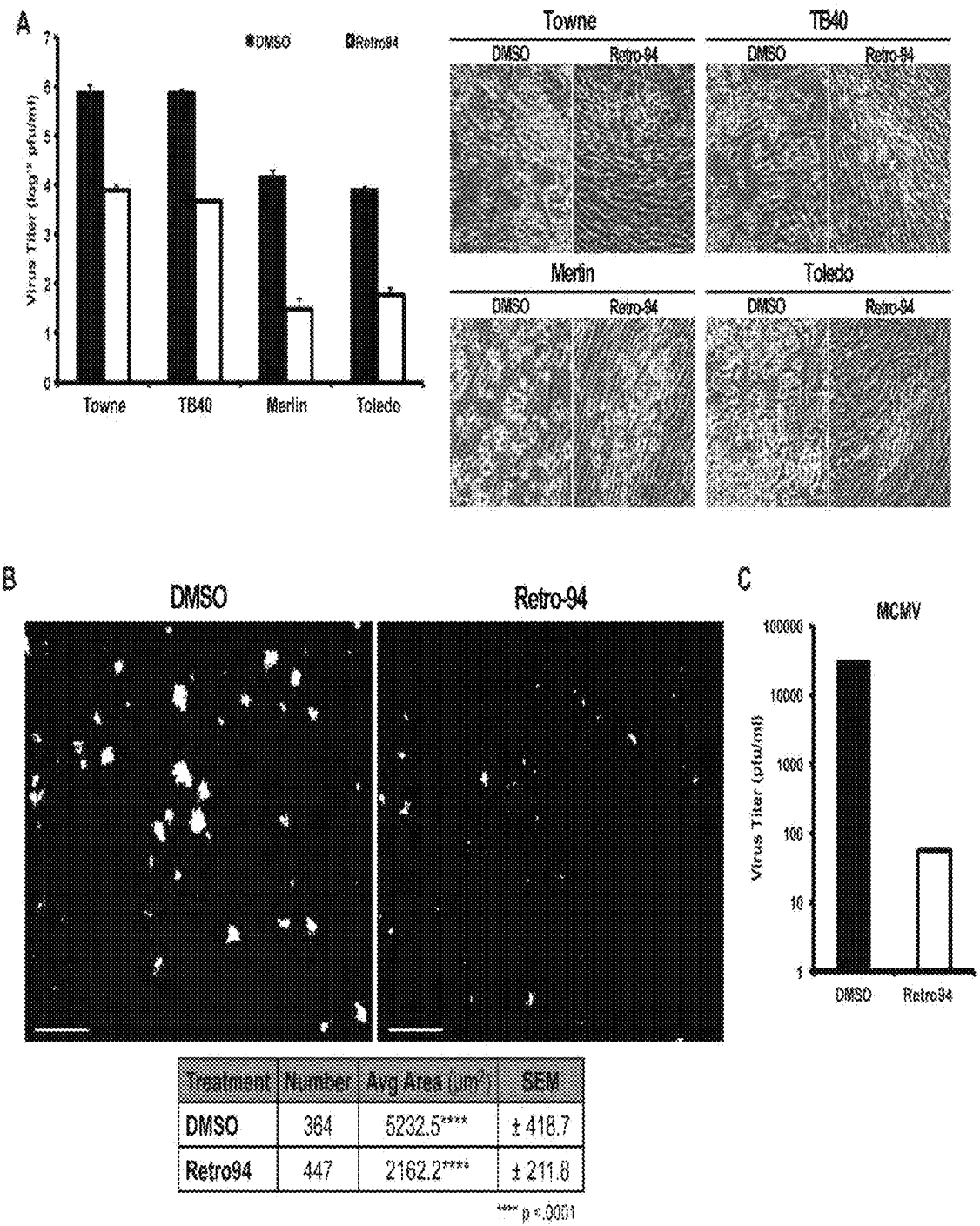
FIGS. 7A-7C show that Retro94-dependent inhibition of HCMV is not strain, cell type or species specific.

Retro94 is a potent inhibitor of cytomegalovirus production. The data herein, convincingly show that Retro94 inhibits production of infectious virions in the context of the laboratory strain AD169. It was queried whether this inhibition was conserved among other HCMV strains. To test this, fibroblasts were infected with the Towne, TB40, Merlin and Toledo strains of HCMV and treated with Retro94 or DMSO at 2 hpi. Growth curve analysis on cells and cell supernatants showed that viral titers of all four strains were about two to three logs lower in the presence of Retro94 (FIG. 7A). This corresponded to less CPE with monolayers being largely intact in Retro94-treated samples with distinct areas of viral activity surrounded by uninfected cells (FIG. 7A). Thus, Retro94 inhibits the replication of multiple strains of HCMV.

It was next investigated if Retro94 inhibited infection of an alternative cell type, particularly since the effect of Retro94 on HCMV replication acts through altering localization of the cellular protein STX5. To test this, ARPE-19 cells were infected with a viral strain of TB40 that expresses mCherry to enable monitoring of the spread of infection. Three weeks after infection, the area of viral centers in both the DMSO and Retro94 treated cells was calculated. The area of the DMSO treated cells was more than twice the area of the Retro94 treated cells (FIG. 7B). Thus, Retro94 inhibits the spread of HCMV in both fibroblasts and epithelial cells.

Since Retro94 has the ability to block various strains of HCMV in multiple cell types, it was tested if this block was species specific. It was found that Retro94 inhibited production of infectious MCMV, decreasing the titer by nearly 3 logs (FIG. 7C). Taken together, these data demonstrate that Retro94 is a general inhibitor of cytomegaloviruses.

Figure 9:
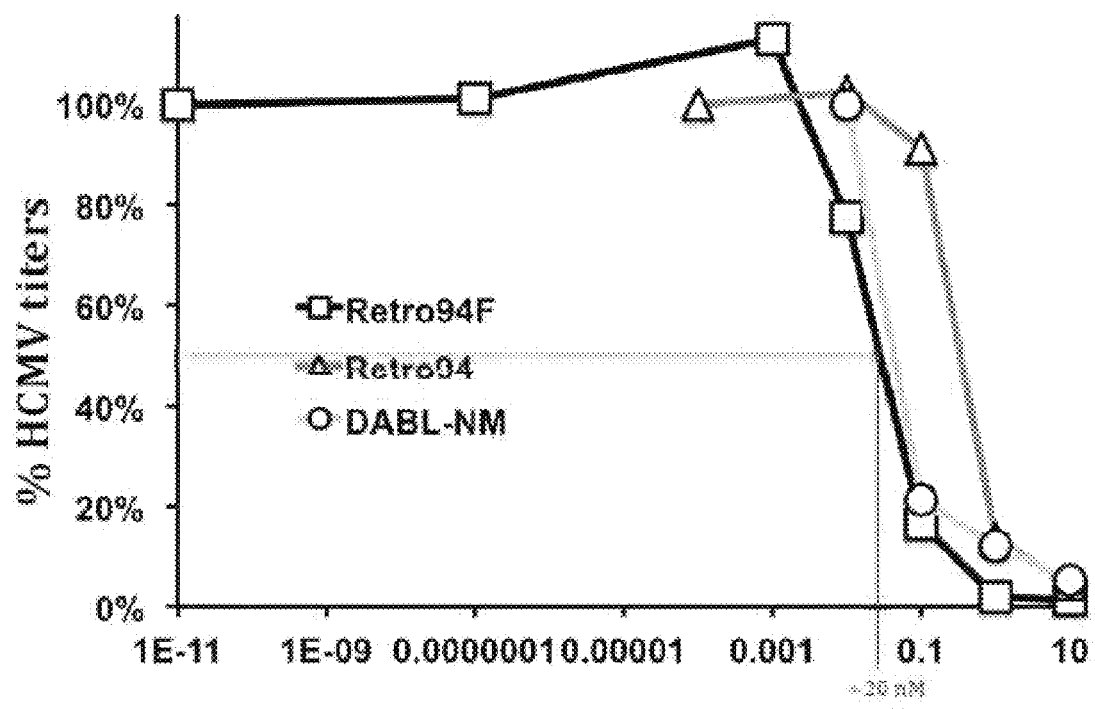
FIG. 9 shows the EC50 of Retro94F and DABL-NM are in the low nanomolar range. Virus titer analysis of HCMV (MOI=3) in DMSO control (No drug) or cells treated with Retro94, Retro94F and DABL-NM at increasing concentrations is provided. Samples were harvested at 96 hpi. Representative data shown are from independent replicates. The dashed line indicates EC50 value (~20 nM).
Figures 10A, 10B:
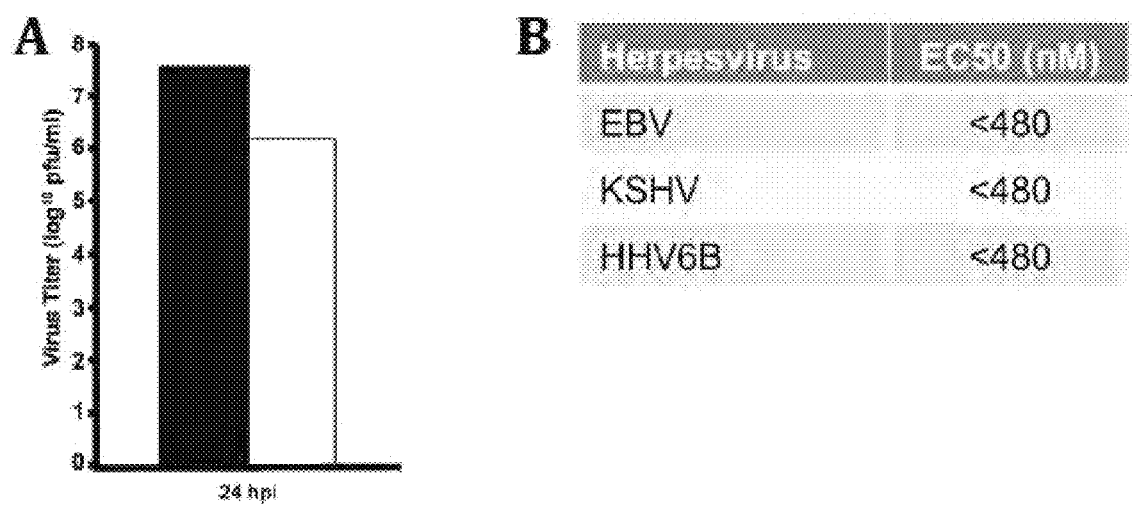
FIGS. 10A-10B show data to provide support for Retro94 and derivatives being effective against other herpesviruses.
Figures 11A, 11B:
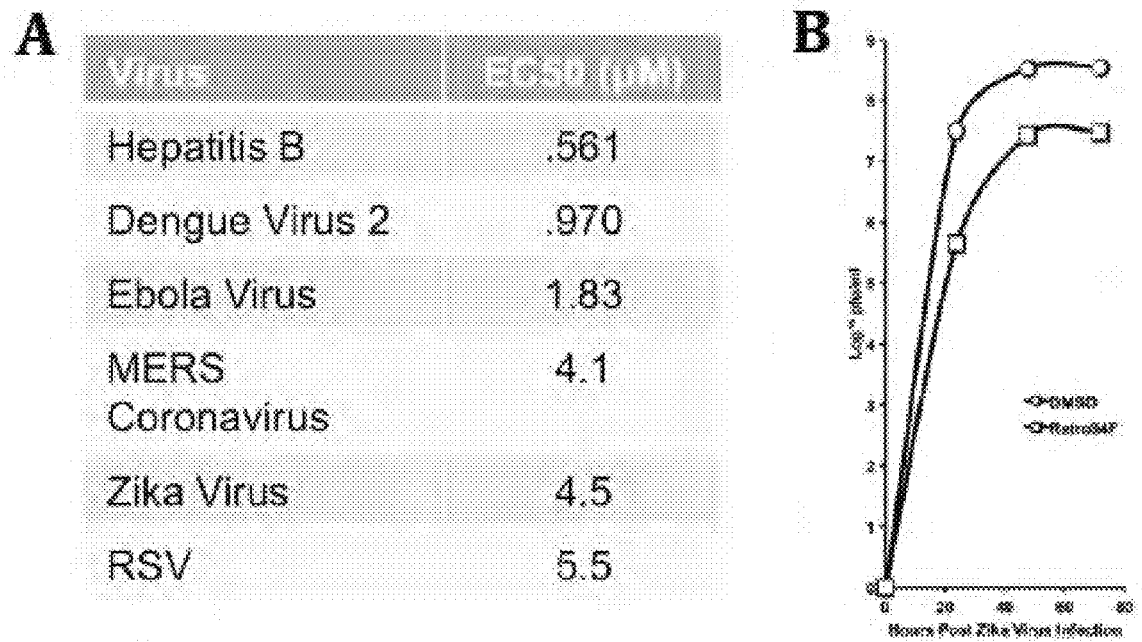
FIGS. 11A-11B shows Retro94F efficacy against non-herpesviruses.

Once Retro94 was identified as an inhibitor of HCMV replication, a library of derivatives was developed. Novel and improved methods for synthesizing some of these compounds was also developed. Two of the developed agents, Retro94F and DABL-NM, have shown increased potency over Retro94. As shown in FIG. 9, the EC50 of Retro94F and DABL-NM were about 20 nM. It as also demonstrated that the Retro94 decreased levels of HSV-1 by ~90% (FIG. 10A), indicating that compound may have efficacy against other herpesviruses. An EC50 value in the low naonmolar range, below the lowest concentration tested, was calculated for other herpesviruses including two cancer causing viruses EBV and KSHV (FIG. 10B). Accordingly, a set of highly potent inhibitors against multiple herpesviruses in culture was identified The potential of our novel compounds to inhibit other viruses was then tested. It was found that Retro94F inhibited other viruses with an EC50 in the high nanomolar to low micromolar range, see FIG. 11A). This includes the ability to inhibit Zika virus infection by approximately 90%, see FIG. 11B). Thus, although our compounds appear to have the highest activity against herpesviruses, they show efficacy against a wide range of virus families and can be developed as pan-viral inhibitors.

Figures 12A, 12B:
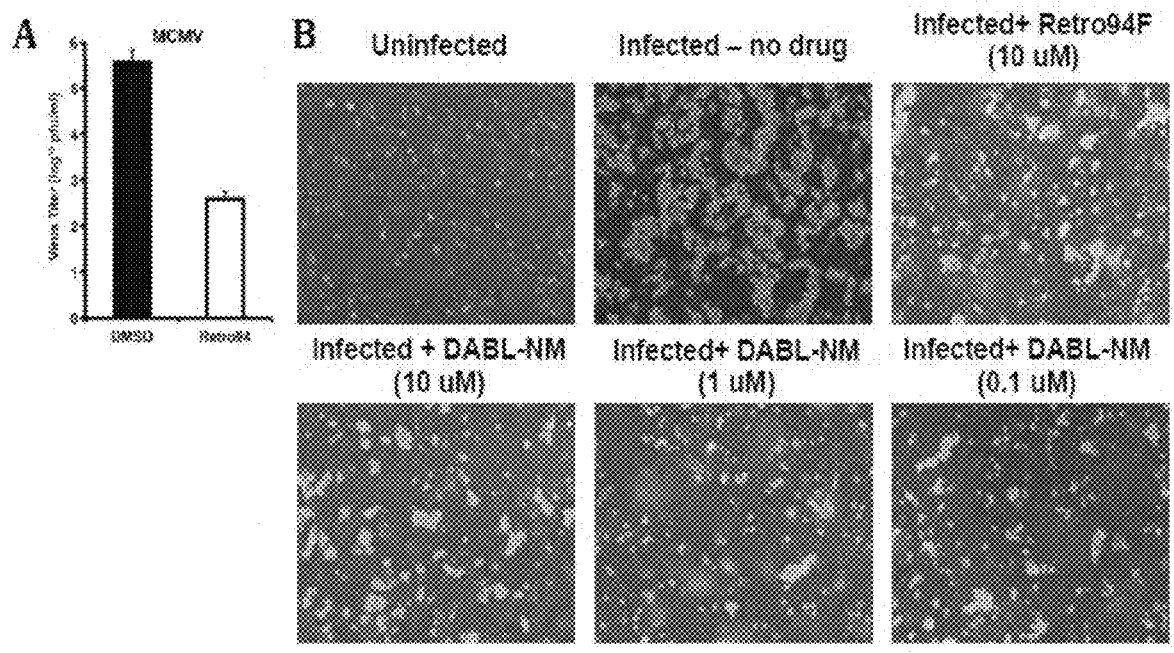
FIGS. 12A-12B provides data in support of Retro94F showing efficacy against diverse mouse viruses in cell culture.
Figures 13A, 13B:
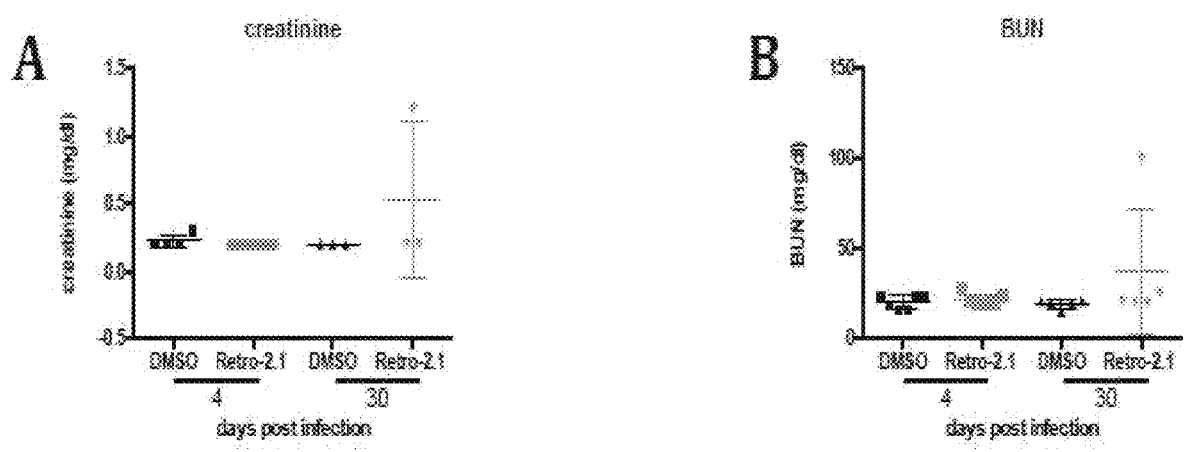
FIGS. 13A-13B provides data to support Retro94F showing no overt toxicity in mice.

While we obtained good results in tissue culture, developing animal models to test the inhibitors was undertaken to allow for studies to test both the properties of the compounds in a host as well as their efficacy against viruses. We first showed that Retro94F was able to inhibit the replication of the mouse equivalent of CMV in culture by greater than two logs, 99%, see FIG. 12A). Efficacy against another mouse virus, murine polyomavirus was shown, and found that the novel derivatives were approximately 100 times more potent than the original Retro94 compound, see FIG. 12B). Thus, at least two mouse infection models in which to show efficacy of the compounds against infection in a host organism is provided. Administration of Retro94F to mice to monitor for potential adverse effects of the compound was undertaken. These initial studies have shown that Retro94F is well tolerated by the mice. For these studies, C57BL/6 mice were injected intraperitoneally once daily with 250 µg of Retro94F or vehicle control in 250 µl of 0.9% saline. These daily injections were continued for 14 straight days with no apparent adverse effects. Analysis of creatinine and BUN levels of treated mice showed that Retro94F did not adversely affect kidney function, see FIGS. 13A & 13B). Thus, the inhibitors appear to be well tolerated by mice.

Figures 14A, 14B, 14C, 14D, 14E:
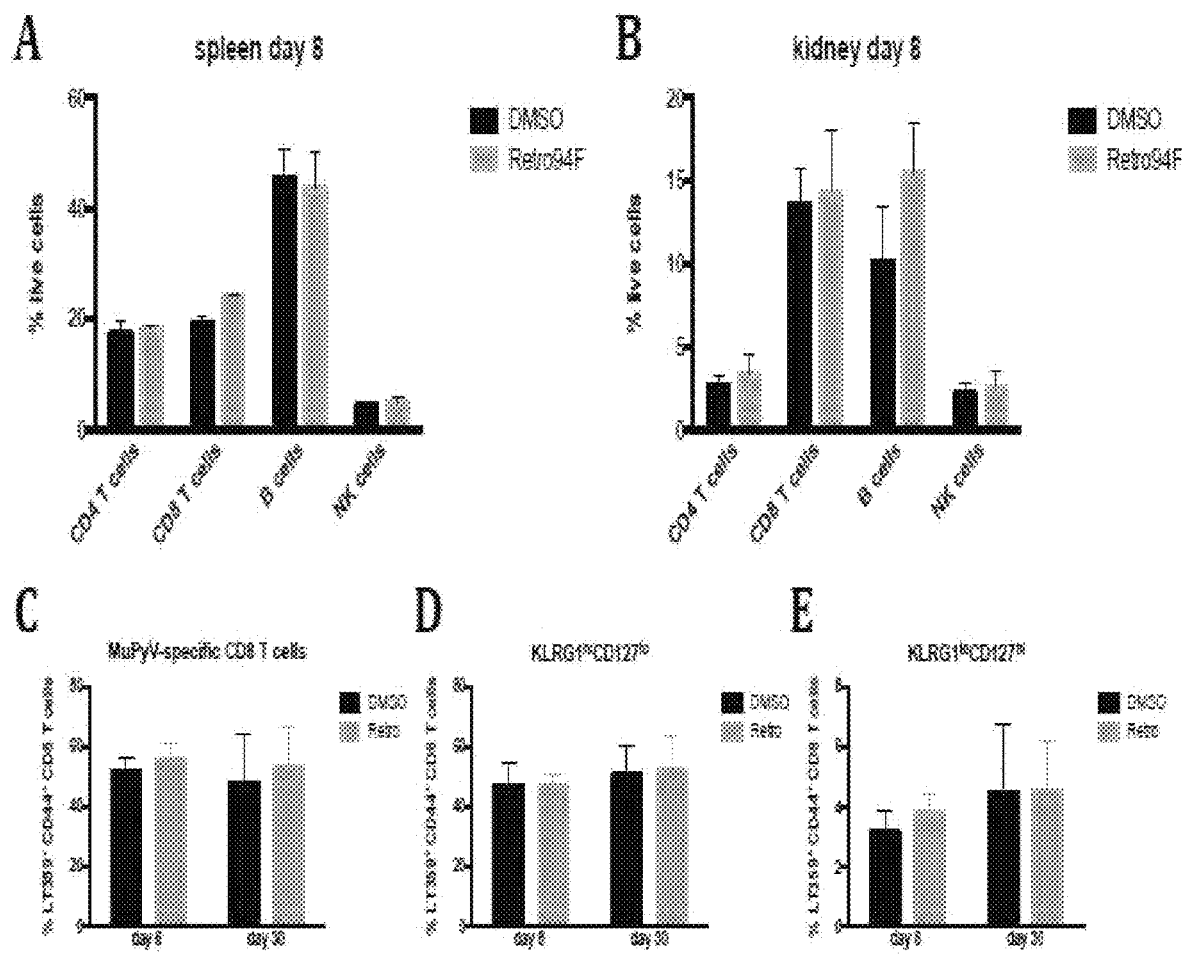
FIGS. 14A-14E shows Retro94F does not adversely affect the immune response. (A-E) B6 mice were infected via hind footpads with 2×10^5 PFU of MuPyV.

With the goal of administering the compounds to immunocompromised individuals with already challenged immune responses, it is important to show that the inhibitors would not adversely affect an immune response. Challenge with an unrelated murine virus (mouse polyomavirus) after Retro94F treatment showed no signs of distress, with equivalent levels of immune cells as control treatment, see FIGS. 14A & 14B) and did not alter the CD8 T cell response to this virus, see FIGS. 15C&D). Thus, the inhibitors appear to be well tolerated by mice.

Discussion

An important role was identified here for STX5, a cellular SNARE, in HCMV replication. STX5 protein was upregulated late in infection concurrent with cVAC formation and was required for the proper morphology of the cVAC. In contrast, the protein levels of two other SNAREs, STX18 and GS15, rapidly decreased during HCMV infection. This differential regulation of SNAREs provides evidence that HCMV generates a distinct SNARE repertoire that optimizes trafficking conditions for efficient replication. This is consistent with a recent study identifying several HCMV miRNAs that target cellular trafficking factors, including members of the SNARE family (Hook L M, et al. *Cell Host Microbe.* 2014; 15(3):363-73). These miRNAs also affected cVAC morphology. Thus, an important step for HCMV replication is the preparation of cellular trafficking factors to generate the cVAC and deliver factors required for supporting the efficient assembly and transport of virions.

SNARE complexes require a tight interaction between four SNARE motifs from four, or sometimes three, different SNARE proteins. STX5 is normally localized to the Golgi where it participates in different t-SNARE complexes. It was expected that other complex members would also be regulated during infection, but it was surprising to find that only STX5 protein was increased. Future experiments are needed to investigate the mechanistic contribution of STX5 to infection, including its interacting partners. The identification of other SNARE partners that interact with STX5 during infection is complicated by complexes that spontaneously form after detergent lysis and that are in fact non-functional. For example, although STX5 has been identified that it binds to other SNARE proteins, these complexes are not fusogenic when reconstituted into liposomes (Parlati F, et al. *Proc Natl Acad Sci USA*. 2002; 99(8):5424-9). In fact, this study showed that only 2 out of a potential 147 yeast SNARE combinations containing the STX5 homologue, Sed5, promoted fusion. Caution must be used when identifying the STX5 interacting partners relevant to its role during infection, particularly when identifying any potential novel SNARE complexes. These proteomic studies, however, may be useful in identifying important regulatory proteins of STX5, such as tethering factors and SM (Sec1/Munc18-like) proteins.

The requirement for STX5 in cVAC morphology is not unexpected since it has been implicated in maintaining organelle morphology. For example, a single amino acid substitution of a phosphorylated residue on the yeast homologue, Sed5, resulted in the normally disperse yeast Golgi to form an ordered structure similar to the mammalian Golgi apparatus (Weinberger A, et al. *Mol Biol Cell*. 2005; 16(10): 4918-30). Interestingly, another study showed that decreasing STX5 levels promoted Golgi order in the presence of a drug that fragments the Golgi apparatus (Rendón W O, et al. *Histochem Cell Biol*. 2013; 139(5):671-84). Since the formation of the Golgi ring associated with the cVAC would first require disordering the canonical Golgi apparatus, one benefit of the HCMV-induced upregulation of STX5 may be to promote Golgi disorder. However, STX5 is involved in reconstructing the Golgi Apparatus from fragments following mitosis (Rabouille C, et al. *Cell*. 1998; 92(5):603-10), suggesting that STX5 promotes Golgi order. STX5 also participates in both the p97/VCP and NSF-mediated pathways of Golgi reassembly. Since cVAC formation requires the disassembly of the canonical Golgi structure and reassembly into a ring, the increase in STX5 protein may be to promote construction of the Golgi ring in a similar manner as it does to reassemble the Golgi stacks after mitosis. It is known that the multifunctional p97 does play an important role during HCMV infection, particularly in the degradation of proteins such as MHC class I, and perturbing its function during infection may have multiple effects on replication. The STX5-mediated Golgi reassembly, however, requires the p97 cofactor p47 (Rabouille C, et al. *Cell*. 1998; 92(5): 603-10). Future studies can investigate the relationship between p47, STX5 and cVAC formation. It has also been reported that the long chain of STX5 affects ER morphology and that this is accomplished independently of the normal SNARE function of STX5 (Miyazaki K, et al. *J Cell Sci*. 2012; 125(Pt 23):5658-66). Thus, a SNARE-independent contribution of STX5 to HCMV infection may play a role, which may explain why STX5 is upregulated independently of other SNARE proteins.

Identifying an important role for STX5 in infection allowed this study to take advantage of a compound that promotes the mislocalization of STX5 to block the efficient production of HCMV virions. The parent compound of this derivative was originally identified for its ability to block the entry of bacterial toxins, which require retrograde transport for entry (Stechmann B, et al. *Cell*. 2010; 141(2):231-42. Viruses such as polyomavirus and papillomaviruses require the same retrograde transport for entry into cells, and consequently these compounds effectively blocked the establishment of these viral infections [Carney D W, et al. *Bioorg Med Chem*. 2014; 22(17):4836-47; Nelson C D, et al. *MBio*. 2013; 4(6):e00729-13; Lipovsky A, et al. *Proc Natl Acad Sci USA*. 2013; 110(18):7452-7). Efficacy against viruses such as HCMV that do not share this entry pathway has not been previously reported. The discovery herein, that HCMV requires STX5 for assembly allowed the identification of Retro94 as a potent inhibitor of HCMV infection, providing a prime example of how identifying cellular factors important for infection can in fact lead to novel therapeutic targets.

What is claimed:

1. A compound of Formula IV:

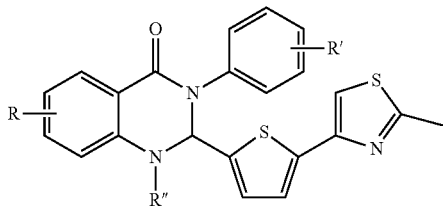

or a pharmaceutically acceptable salt thereof;
wherein
R is selected from CN, C=CH$_2$, C≡CH, NO$_2$, COOH, esters, or heterocycle (5 membered ring, or 6 membered ring with N, O, S);
R' is H; and
R" is selected from H or alkyl.

2. The compound of claim 1, wherein the compound is:

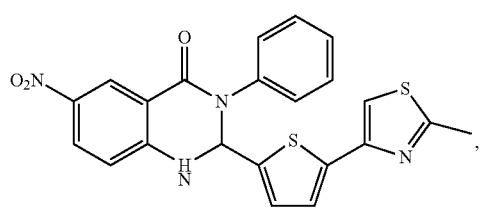 [SMILES: Cc1nc(-c2ccc(C3Nc4ccc([N+](=O)[O-])cc4C(=O)N3c3ccccc3)s2)cs1]

or a pharmaceutically acceptable salt thereof.

3. The compound of claim 1, wherein the compound is:

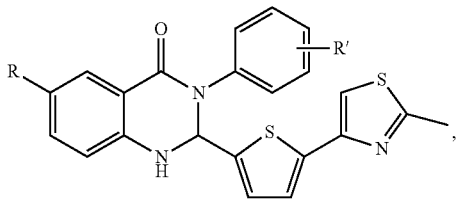

or a pharmaceutically acceptable salt thereof.

4. The compound of claim 1, wherein the compound is:

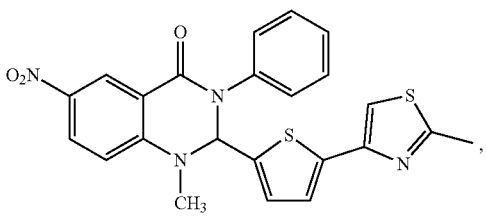 [SMILES: Cc1nc(-c2ccc(C3N(C)c4ccc([N+](=O)[O-])cc4C(=O)N3c3ccccc3)s2)cs1]

or a pharmaceutically acceptable salt thereof.

5. The compound of claim 1, wherein the compound is:

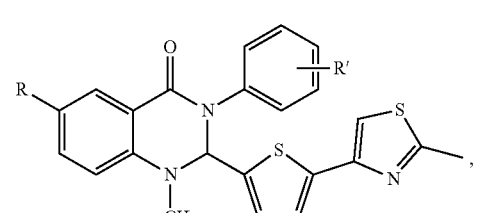

or a pharmaceutically acceptable salt thereof.

6. The compound of claim 1, wherein the compound is:
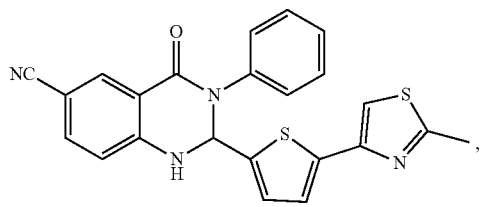 [SMILES: Cc1nc(-c2ccc(C3Nc4ccc(C#N)cc4C(=O)N3c3ccccc3)s2)cs1]
or a pharmaceutically acceptable salt thereof.
7. The compound of claim 1, wherein the compound is:
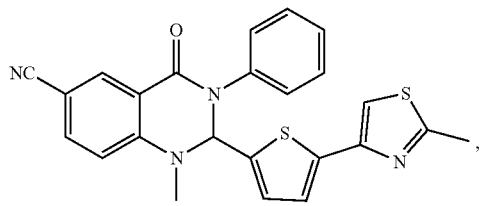 [SMILES: Cc1nc(-c2ccc(C3N(C)c4ccc(C#N)cc4C(=O)N3c3ccccc3)s2)cs1]
or a pharmaceutically acceptable salt thereof.
* * * * *